United States Patent [19]

Fischer

[11] Patent Number: 5,593,860
[45] Date of Patent: Jan. 14, 1997

[54] EXPRESSION PLASMIDS CONTAINING THE DEO PROMOTER, AND BACTERIAL HOSTS CONTAINING THE PLASMIDS

[75] Inventor: Meir Fischer, Rehovot, Israel

[73] Assignee: Bio-Technology General Corp., Iselin, N.J.

[21] Appl. No.: 261,750

[22] Filed: Jun. 17, 1994

Related U.S. Application Data

[63] Continuation of Ser. No. 92,279, Jul. 15, 1993, abandoned, which is a continuation of Ser. No. 962,033, Oct. 15, 1992, abandoned, and a continuation of Ser. No. 225,095, Jul. 27, 1988, abandoned, which is a continuation-in-part of Ser. No. 86,159, Aug. 14, 1987.

[51] Int. Cl.$^6$ .............................. C12P 21/00; C12N 15/00
[52] U.S. Cl. ..................... 435/69.1; 435/252.33; 435/320.1; 935/29
[58] Field of Search .................. 435/69.1, 69.2, 435/69.3, 69.4, 69.5, 69.51, 69.6, 71.2, 91.1, 172.1, 172.3, 320.1; 536/24.1, 23.2–23.53; 935/29, 38–41, 43, 72–75

[56] References Cited

U.S. PATENT DOCUMENTS

4,806,471  2/1989  Molin et al. .......................... 435/69.1

FOREIGN PATENT DOCUMENTS

8401171  3/1984  WIPO .............................. 435/172.3

OTHER PUBLICATIONS

Hammer–Jesperson et al., Molec. Gen. Genet. 137: 327–335 (1975).
R. S. Buxton et al., J. Mol. Biol. 114: 287–300 (1977).
R. S. Buxton et al., Journal of Bacteriology 136(2): 668–681 (1978).
P. Valentin–Hansen et al., Molec. Gen. Genetics 159: 191–202 (1978).
P. Valentin–Hansen et al., J. Mol. Biol. 133: 1–17 (1979).
P. Valentin–Hansen et al., The EMBO Journal 1(3):317–322 (1982).
Meir Fischer et al., Gene 17: 291–298 (1982).
G. Dandanell et al., The EMBO Journal 4(12): 3333–3338 (1985).
P. H. Pouwels et al., "Cloning Vectors", pp. I–1 to I–8, Elsevier Science Publishers (1985).
M. Mieschendahl et al., Biotechnology 4: 802–808 (1986).
M. Zabeau et al., EMBO J. 1: 1217–1224 (1982).
A. S. Waldman et al., J. Biol. Chem. 258: 11571–11575 (1983).
P. Valentine–Hansen et al., EMBO J. 1(9): 1049–1054 (1982) (Exhibit 1).

*Primary Examiner*—James Martinell
*Attorney, Agent, or Firm*—John P. White

[57] ABSTRACT

Plasmids are provided which upon introduction into a suitable *Escherichia coli* host render the host capable of effecting expression of DNA encoding a desired naturally-occurring polypeptide or polypeptide analog thereof under the control of the deo P1-P2 promoter. Further plasmids are also provided which thermoinducibly direct expression of eucaryotic genes under the control of a λ $P_L$ promoter and a thermolabile repressor protein present on the same plasmid under the control of a deo P1 promoter. These plasmids have been inserted into various hosts, some of which contain DNA encoding the repressor protein.

Such plasmids may be used to produce polypeptides such as human copper/zinc superoxide dismutase, hMnSOD-hGPX fusion polypeptides, human manganese superoxide dismutase, human growth hormone, bovine growth, porcine growth, human growth hormone-apolipoprotein E fused polypeptides, apolipoprotein E and various fibronectin domains.

39 Claims, 52 Drawing Sheets

A: Deletion in ampicillin - resistance gene
B: Deletion of deo $P_1P_2$ region
C: Wild - type pJBF 5401
D: Mutant pJBF 5401, designated pMF 5416

1. Cut NdeI
2. Fill in T₄ Polymerase

T₄ DNA Ligase

| | |
|---|---|
| 1. Cut PstI | 1. Cut BamHI |
| 2. Digest 3' with T₄ Polymerase | 2. Fill in T₄ Polymerase |
| 3. Isolate Large Fragment | 3. Isolate Small Fragment |

T₄ DNA Ligase

1. NsiI
2. T4 DNA polymerase – Remove 3' end
3. SspI
4. Isolate large (4 kb) fragment 1. NdeI
2. Klenow fill in
3. SspI
4. Isolate <u>deo</u> (1.3 kb) fragment T4 DNA Ligase 1. Cleave with ClaI
2. Fill in "Klenow"

1. Cleave with SspI
2. Cleave XmnI
3. Isolate SspI-XmnI small fragment $T_4$ DNA Ligase 1. Cleave with ClaI
2. Fill in "Klenow"

1. Cleave with SspI
2. Cleave XmnI
3. Isolate SspI-XmnI small fragment

T4 DNA Ligase

| 1. Cut AatII + PstI | 1. Cut EcoRI + AvaI |
| 2. Klenow digest 3' ends | 2. Fill in Klenow |
| 3. Isolate Large Fragment | 3. Isolate Small Fragment |

T4 DNA Ligase

1. Cut SspI + PvuII + EcoRI
2. Isolate Large Fragment
3. Cut Isolated Fragment HincII
4. Isolate 350 bp SspI-HincII 1. Cut EcoRV T4 DNA Ligase 1. Cleave BglII+StyI
2. Isolate Large fragment 1. Cleave BglII+StyI
2. Isolate small fragment T4 DNA Ligase

EXPRESSION PLASMIDS CONTAINING THE DEO PROMOTER, AND BACTERIAL HOSTS CONTAINING THE PLASMIDS

This application is a continuation of U.S. Ser. No. 08/092,279, filed Jul. 15, 1993, abandoned; which is a continuation of U.S. Ser. No. 07/962,033, filed Oct. 15, 1992, abandoned; which is a continuation of U.S. Ser. No. 07/225,095, filed Jul. 27, 1988, abandoned; which is a continuation-in-part of U.S. Ser. No. 07/086,159, filed Aug. 14, 1987.

BACKGROUND OF THE INVENTION

Expression vectors, including expression plasmids are used commercially to produce gene products more efficiently than previously available methods such as extraction from natural sources and organic synthesis. *Escherichia coli* is widely used as a host in which such gene products may be produced using expression plasmids. A comprehensive discussion of expression vectors appears in P. H. Pouwels, B. E. Enger-Valk and W. J. Brammer, *Cloning Vectors*, Elsevier, publs (1985).

A number of control mechanisms which regulate the level of gene expression in prokaryotic vectors have been described. The regulatory process may operate at the transcriptional or translational level. At the transcriptional level control of gene expression is associated with inhibition or stimulation of mRNA synthesis.

One method of increasing the level of expression of a desired gene product is to use a vector in which the gene to be expressed is under the control of a strong promoter, and this is the predominant approach used in the biotechnology industry to express gene products at high levels.

The transcriptional control system consists of a DNA sequence contained in or adjacent to, a promoter which is capable of binding a repressor molecule. When the repressor molecule binds to a specific strain of DNA, transcription of DNA to mRNA is prevented. To initiate transcription of DNA to mRNA the repressor molecule has to be removed or dissociated from its binding site, and this is achieved by a specific chemical or physical stimulus. In many cases of transcriptional control an additional component is needed to drive transcription to its highest capacity. One example of such a component is cyclic AMP-receptor protein (CRP) which is involved in the regulation of many genes in catabolic pathways.

Expression plasmids containing the regulatable promoters $\lambda P_L$, trp or lac, have been extensively used in the art. Other promoters which have been used include the regulatable rec A and $\lambda P_R$ promoters, the constitutive amp and lpp promoters, and artificial promoters created by fusion of two different DNA sequences or by chemical synthesis of DNA sequences.

The *Escherichia coli* deo operon has been studied by Hammer-Jesperson and co-workers. [K. Hammer-Jesperson and A. Munch-Peterson, Molec. gen. Genet. 137: 327–335 (1975); R. S. Buxton, H. Albrechtsen and K. Hammer-Jesperson, J. Mol. Biol. 114: 287–300 (1977); R. S. Buxton, K. Hammer-Jesperson and T. D. Hansen, J. Bacteriol. 136: 668–681 (1978); P. Valentin-Hansen and K. Hammer-Jesperson, J. Mol. Biol. 133: 1–17 (1979); and P. Valentin-Hansen, H. Aiba and D. Schumperli, The EMBO Journal 1: 317–322 (1982)].

As illustrated in FIG. 20, the deo operon consists of four closely-related genes encoding enzymes involved in nucleotide and deoxynucleotide catabolism, namely, deoxyriboaldolase (deo C), thymidine phosphorylase (deo A), phosphodeoxyribomutase (deo B) and purine nucleotide phosphorylase (deo D). Transcription of all four closely-related deo genes is regulated at two promoter/operator regions, deo P1 and deo P2 (or P1 and P2). When the transcription of a gene is controlled by the deo P1 and deo P2 promoters functioning in tandem, the term deo P1-P2 promoter or deo promoter/operator region is used.

Initiation of transcription from P1 is negatively controlled by the deo R repressor and is activated by the inducer deoxyribose-5-phosphate. Initiation of transcription from P2 is negatively controlled by the cyt R repressor, the inducer being cytidine. Activation of P2 depends on the cyclic AMP/cyclic AMP receptor protein complex, cAMP/CRP, although P2 may also be controlled by the deo R repressor. The two distal genes B and C in the deo operon are subject to an additional transcriptional control: an internal promoter/operator region P3, regulated by unknown control proteins and responding to induction by inosine and guanosine. The sequence of the deo P1-P2 promoter/operator region is known, and the entire deo P1-P2 promoter/operator region is approximately 760 bp long, with the two promoters being separated by a distance of about 600 bp. (P. Valentin-Hansen et al., The EMBO Journal 1: 317–322 (1982)).

Expression of a gene product under deo P2-driven transcription is very low in the presence of glucose and very high in the presence of other energy producing sources. Transcription driven by deo P1 is not subject to the glucose effect (catabolite repression), and also deo P1 is a much weaker promoter than deo P2. Therefore, one may manipulate expression of a gene product driven by the deo P1 promoter both by external means and by choosing *Escherichia coli* cells which possess no functional deo R repressor.

The entire deo operon has been cloned from $\lambda$ bacteriophage harboring the deo operon and the deo enzymes have been expressed in *Escherichia coli* host cells [M. Fischer and A. Short, Gene 17: 291–298 (1982)]. It was found that the enzyme activities of bacteria containing the cloned deo operon were amplified 500–50,000 fold over the level found in wild-type cells. The degree of amplification depends on host genotype. In host cells possessing both the deo R and cyt R repressors amplification of the enzyme thymidine phosphorylase is about 500 fold; in host cells containing no functional deo R and cyt R repressors, amplification of thymidine phosphorylase is about 50,000 fold.

G. Dandanell and I. K. Hammer, The EMBO Journal 1: 3333–3338 (1985), disclose transcriptional fusion of deo P1 and deo P2 promoter fragments to the *Escherichia coli* galactokinase gene. Dandanell et al. examined the expression of galactokinase, i.e., a prokaryotic gene product, under the control of the deo P1-P2 promoters integrated into the bacterial chromosome. By contrast, the present invention teaches the use of the deo P1-P2 promoter on multicopy plasmids to drive the expression of eucaryotic gene products.

Dandanell et al. state that the $\lambda P_L$ promoter is 2–3 times as strong as the deo P2 promoter (p. 3326, column 2). By contrast, the levels of expression obtained by utilization of the specific polypeptides and particular regulatory elements of the subject invention approach or exceed those obtained by using a $\lambda P_L$ promoter.

By suggesting that the $\lambda P_L$ promoter is 2 to 3 times stronger than the deo P2 promoter, which in turn is stronger than the deo P1 promoter, Dandanell et al. teach away from the use of deo P1-P2 promoter as a strong promoter. As noted above, applicants have found that when using the plasmids of the subject invention which contain the deo P1-P2 promoter together with the other regulatory components, polypeptides are produced in unexpectedly large amounts.

PCT International Publication No. WO 84 01171, published Mar. 29, 1984, describes, but does not enable, the use of a deo promoter to express very low amounts of the controlling protein of *Escherhichia coli* replication, i.e., a noneucaryotic protein.

Plasmids expressing gene products under the control of λ $P_L$ promoter, yet independent of λ genes on the host chromosome, have been designated by us as "independent" plasmid expression vectors. M. Mieschendahl, T. Petri and Urs Hanggi, Biotechnology 4: 802–808 (1986), for example, disclose an independent plasmid in which the λ cI repressor gene is controlled by the tryptophan operator/promoter. However, this is not a temperature controlled system.

M. Zabeau and K. K. Stanley, the EMBO Journal 1: 1217–1224 (1982) placed the gene for a temperature-sensitive cI repressor on a low copy plasmid which is compatible with pBR322 vectors. This approach, however, requires that two plasmids be used and that the cI plasmid be kept in the cells by selection.

A. S. Waldman, E. Haeusslein and G. Milman, J. Biol. Chem. 258: 11571–11575 (1983) cloned the gene and authentic promoter for the temperature sensitive cI 857 repressor directly onto a plasmid. However, good expression of cloned genes was not achieved in such constructs due to the amplification of the cI gene and the concomitant increase in the number of cI molecules. In these experiments, the cloned gene product was only about 4% of total, soluble, cellular protein.

Nowhere in the art is there described an efficient temperature-sensitive, expression system where the heat-inducible expression of genes carried on expression vectors is independent of expression of genes on the host chromosome. Thus, there is no disclosure of efficient, temperature-sensitive "independent" plasmid expression vectors.

In one embodiment of the present invention the weak deo P1 promoter obtained from the deo operon is inserted into a λ $P_L$ expression plasmid where it controls the expression of λ cI 857 repressor gene, thus allowing thermoinducible expression of gene products controlled by the λ $P_L$ promoter on the same plasmid. This expression plasmid is thus independent of λ genes on the host chromosome and may be transformed into a wide variety of hosts. It is thus an "independent" expression plasmid. Unexpectedly, expression of desired gene products using this plasmid can be achieved at levels of up to 25% of total cellular protein.

SUMMARY OF THE INVENTION

This invention provides a double-stranded DNA plasmid which upon introduction into a suitable *Escherichia coli* host cell renders the host cell capable of effecting expression of DNA encoding a desired, naturally-occurring, eucaryotic polypeptide or a polypeptide analog thereof having the biological activity of, and an amino acid sequence which is substantially the same as, yet different from, that of the naturally-occurring polypeptide, and thereby effecting production of the polypeptide or polypeptide analog comprising in 5' to 3' order the following:

a) DNA which includes in 5' to 3' order the tandem promoters deo P1 and deo P2;

b) DNA which includes a ribosomal binding site for rendering the mRNA transcribed from the DNA encoding the polypeptide or polypeptide analog capable of binding to ribosomes within the host cell;

c) an ATG initiation codon; and d) DNA encoding the polypeptide or polypeptide analog in phase with the initiation codon;

and which additionally includes a DNA sequence comprising an origin of replication from a bacterial plasmid capable of autonomous replication in the host cell and a DNA sequence which contains a gene associated with a selectable or identifiable phenotypic trait which is manifested when the vector is present in the host cell.

Suitable naturally-occurring polypeptides produced by the plasmids of the invention include human copper/zinc superoxide dismutase, human manganese superoxide dismutase, human glutathione peroxidase, human growth hormone, bovine growth hormone, porcine growth hormone, human apolipoprotein E or various domains of fibronectin. It will of course be understood by those skilled in the art that the plasmids of the invention may contain DNA encoding other desired naturally-occurring polypeptides and polypeptide analogs thereof.

The invention further provides host plasmid systems for producing a naturally-occurring, eucaryotic polypeptide or a polypeptide analog thereof, comprising the various plasmids of the invention in a suitable *Escherichia coli* host.

The invention also provides a method of producing a naturally-occurring polypeptide, or a polypeptide analog thereof, which comprises growing the host plasmid system of the invention under conditions permitting production of the polypeptide or analog and recovering the resulting polypeptide or analog. Preferred conditions for producing the desired naturally-occurring polypeptides and polypeptides of this invention are also provided.

The invention also provides a double-stranded DNA, a so-called "independent" plasmid, comprising in 5' to 3' order DNA which includes the promoter and operator $P_LO_L$ from λ bacteriophage and DNA encoding a desired polypeptide and which additionally comprises in 5' to 3' order a DNA sequence which contains the deo P1 promoter and DNA which encodes a cI thermolabile repressor of the λ $P_L$ promoter, expression of the repressor being under the control of the deo P1 promoter. Because production of the λ repressor protein does not depend on the presence of λ genes on the host chromosomes, the plasmid has been designated an independent plasmid.

Such independent plasmids may be used to produce human copper/zinc superoxide dismutase, human growth hormone, bovine growth hormone, porcine growth hormone or apolipoprotein E. It will of course be understood by those skilled in the art that such independent plasmids may contain DNA encoding other desired naturally-occurring polypeptides and polypeptide analogs thereof.

This invention also provides a host plasmid system and methods for producing desired polypeptides, or analogs thereof, comprising growing the host plasmid system under conditions permitting production of the polypeptide or polypeptide analog, and recovering the polypeptide or analog so producted.

Finally, the invention provides double-stranded DNA plasmids comprising tandem promoters deo P1 and deo P2 and an AT rich sequence translation enhancer. The translation enhancer sequence increases production level of polypeptides produced by the plasmids of the invention.

DESCRIPTION OF THE FIGURES

The restriction maps for each of the plasmids shown in FIGS. 1–52 do not identify all the restriction sites present on each plasmid. In some cases restriction sites are shown in one figure, but not in another. However, in all cases those restriction sites necessary to enable one skilled in the art to practice the invention are shown. The relative sizes of the various plasmids are not drawn to scale and no conclusions may be drawn concerning the size of the plasmids from the figures. The deo promoters have been labeled deo P1-P2, deo P1 or deo P2.

All of the plasmids deposited in connection with this application, except those for which it is specifically stated otherwise, have been deposited with the American Type Culture Collection (ATCC) in Rockville, Md. 20852, U.S.A., pursuant to the Budapest Treaty on the International Recognition of the Deposit of Microorganisms for the Purpose of Patent Procedure ("Budapest Treaty").

λ cI 857: DNA containing the entire deo operon (prepared as described in Example 1) was cleaved with AvaII and filled-in (Klenow reaction). BamHI linkers were added and the AvaII fragment with BamHI linkers was ligated with $T_4$ ligase to BamHI—cleaved pBR322 (ATCC Accession No. 37017—non-Budapest Treaty Deposit). The resulting plasmid, pJBF-5401A, was digested with BamHI, and the 900 bp fragment containing the deo P1-P2 promoters was religated to pBR322 (also cleaved with BamHI). The resulting plasmid, designated pJBF-5401, consists of pBR322 DNA and the deo P1-P2 promoter region DNA. Plasmid pJBF-5401 has been deposited pursuant to the Budapest Treaty with the American Type Culture Collection (ATCC) in Rockville, Md. under ATCC Accession No. 67359.

Figure 2:
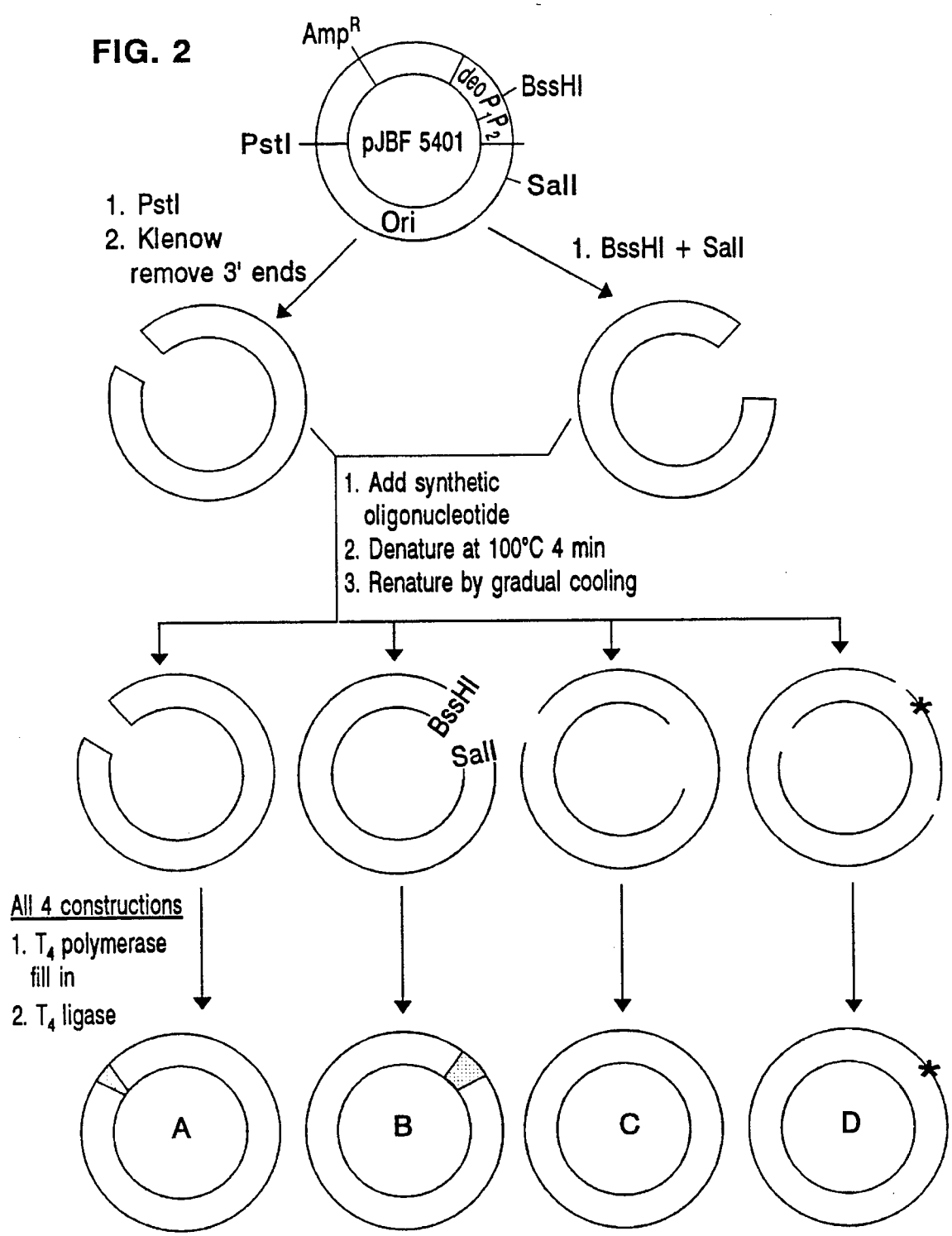

FIG. 2: Site-directed mutagenesis of pJBF-5401

The vector pJBF-5401 containing the deo P1-P2 promoter was modified to introduce an NdeI restriction site between the Shine-Dalgarno sequence of the ribosomal binding site (RBS) and the first ATG of the coding DNA. This was accomplished by site-directed mutagenesis, using the method of Y. Morinaga et al., Biotechnology 2: 636–639 (1984). pJBF-5401 was digested with PstI to form a linear DNA fragment and allowed to anneal with the large fragment produced by BssHI/SalI digestion of pJBF-5401.

A 20 bp synthetic DNA fragment which spans nucleotides 750–770 of the deo P1-P2 promoter sequence was chemically synthesized such that an NdeI site is generated at the proper distance from the RBS; this 20 bp sequence was designated BTG sequence #2015. The original sequence and the newly constructed site are shown below, where the underlined bases show the two nucleotides which were substituted.

Original Sequence—GAGAATGAAATGACTGATCT—

BTG Sequence #2015—GAGAATCATATGACTGATCT—NdeI site

The synthetic DNA fragment was annealed to the single stranded region on the parent strand, and the remaining gap filled in with $T_4$ DNA polymerase to yield plasmid pMF-5416 (plasmid D), which contains deo P1-P2 (operator/promoter sequence) and the new NdeI restriction site; however, sequence analysis revealed a 48 bp deletion in the deo P2 region (see Example 1).

Figure 3:
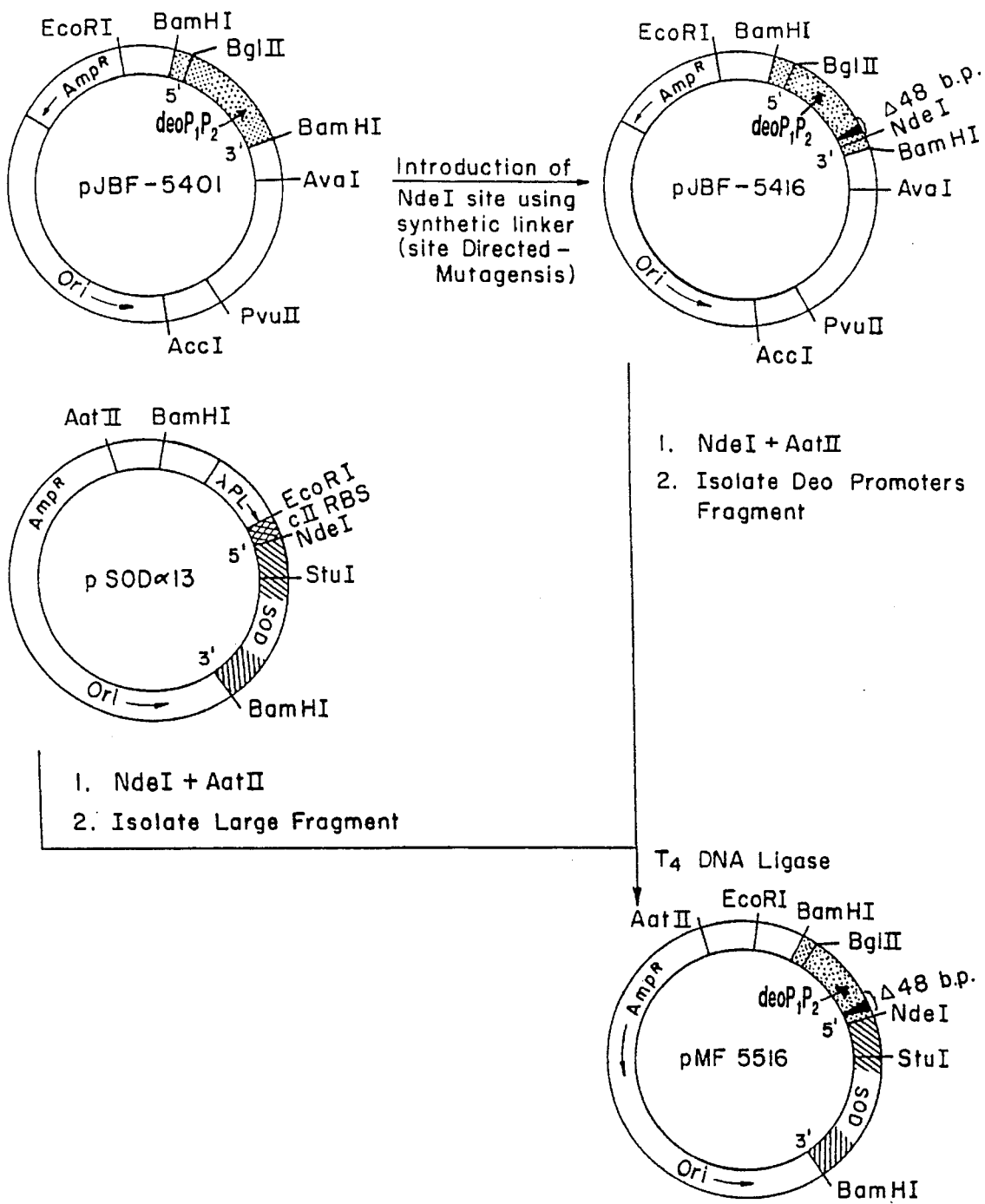

FIG. 3: Construction of pMF-5516

Figure 30:
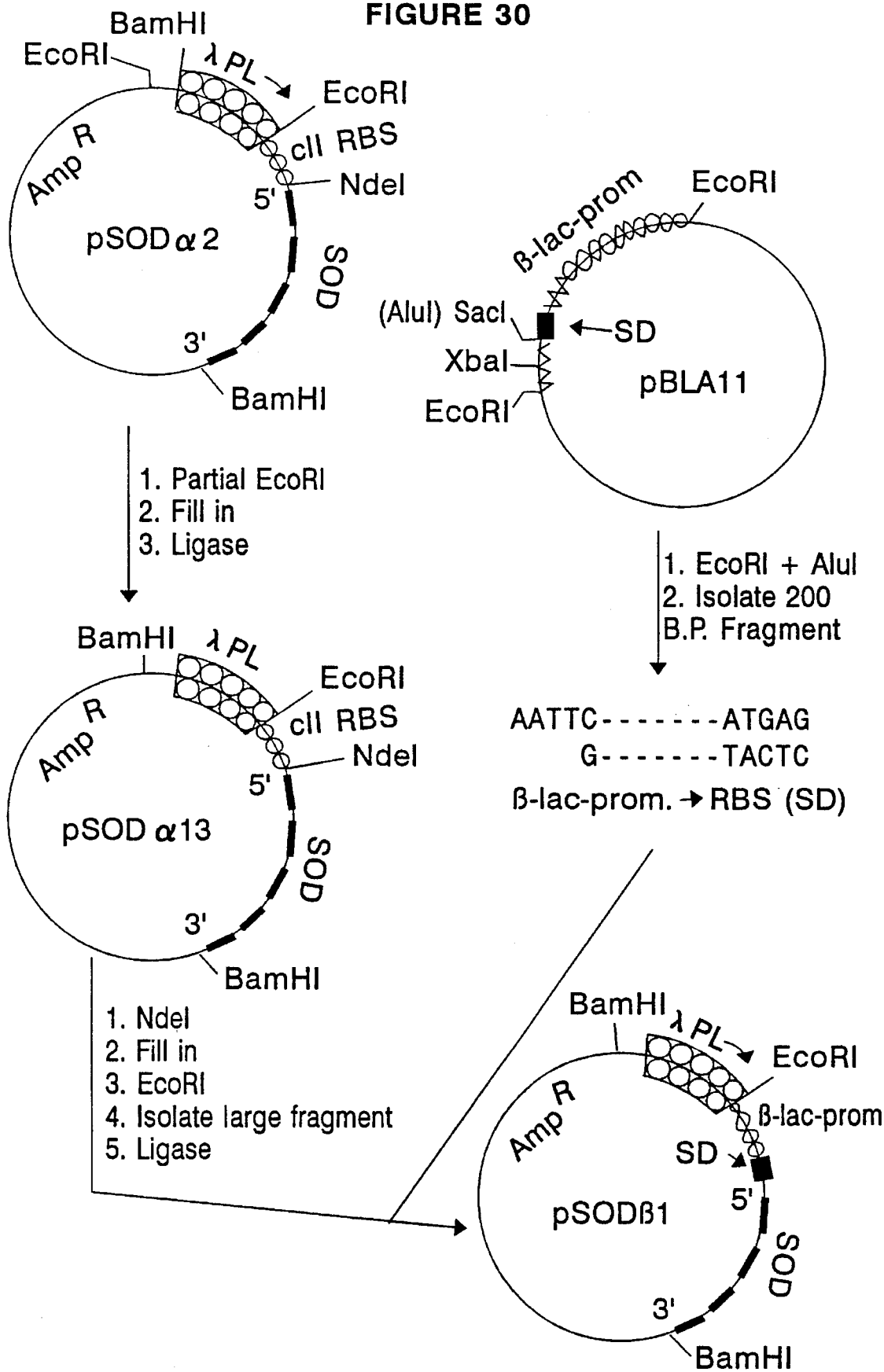

Plasmid pSODα13 (constructed as shown in FIG. 30 from pSODα2 (ATCC Accession No. 39786)) contains the gene for human copper/zinc superoxide dismutase (hSOD) which is expressed under the control of the λ $P_L$ promoter and the cII ribosomal binding site. AatII-NdeI digestion of pSODα13 yields a large fragment which contains the SOD gene but not the λ $P_L$ promoter and RBS. AatII-NdeI digestion of pMF-5416 produced a 900 bp double stranded segment containing the deo P1-P2 promoter (with the 48 bp deletion in the P2 region). Ligation of these two fragments produced a plasmid designated pMF-5516, which contains a modified deo P1-P2 promoter (with the 48 bp deletion) and the hSOD gene preceded by the Nde restriction site.

Figure 4:
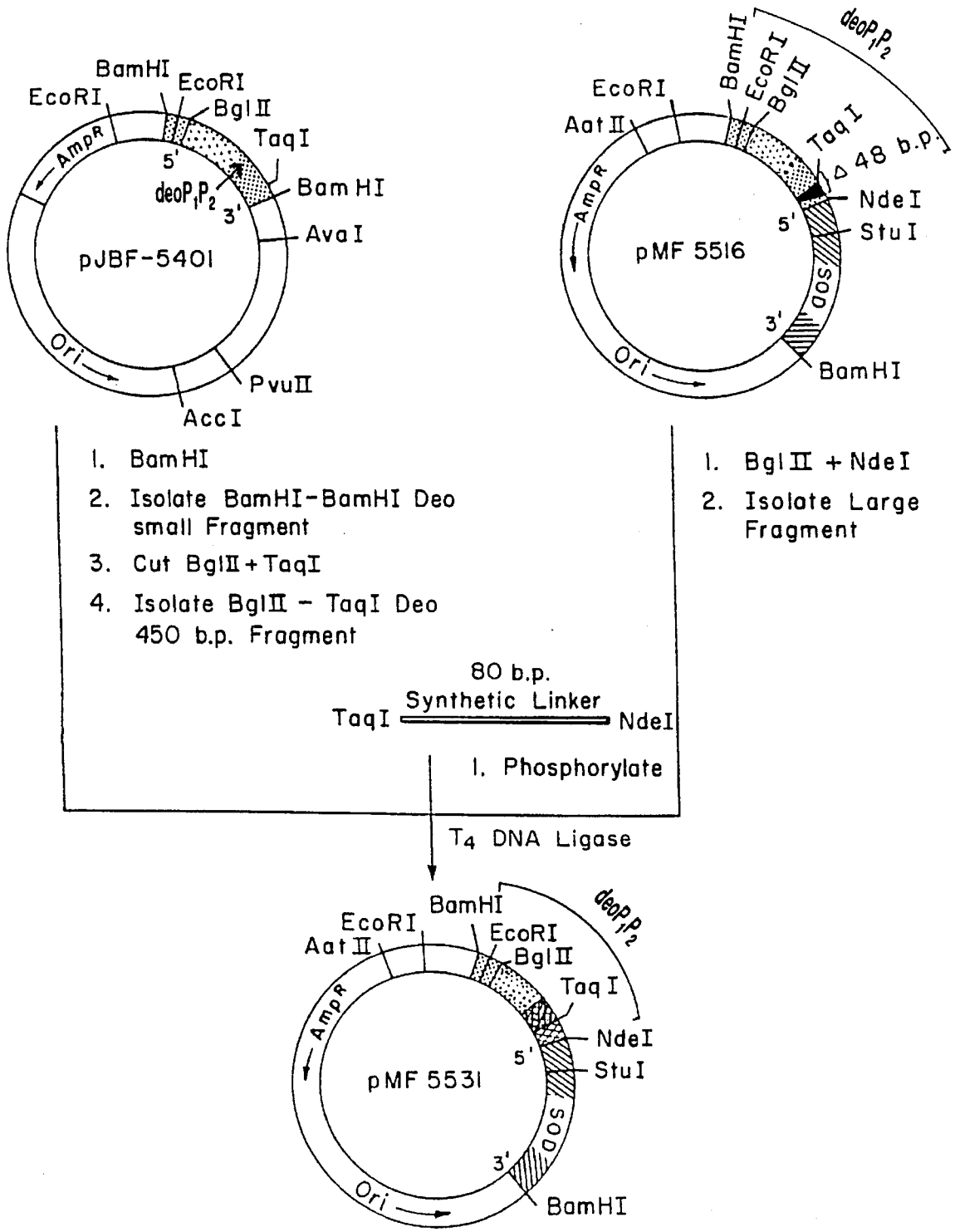

FIG. 4: Construction of pMF-5531 pMF-5516 was modified to reinsert the deleted segment of 48 bp. To achieve this end, the following six single stranded synthetic DNA sequences were annealed to yield three double stranded sequences extending from bp 678 to bp 760 of the P2 region, i.e., the region extending from the TaqI site to the newly constructed NdeI site. (The complete sequence of the deo P1-P2 promoter/operator region is given by P. Valentin-Hansen, H. Aiba and D. Schumperli, the EMBO Journal 1: 317–322 (1982)).

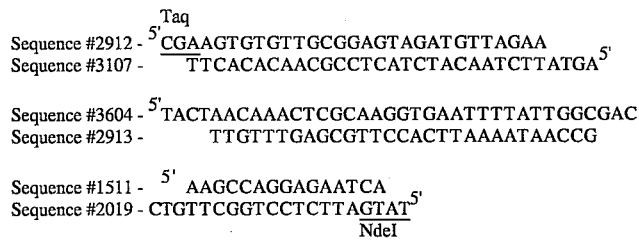

Strand numbers 3107, 3604, 2913 and 1511 were phosphorylated by polynucleotide kinase and then each strand was annealed to its complementary strand viz, strand #2912 to #3107, #3604 to #2913 and #1511 to #2019. The three double-stranded sequences were joined by ligation to generate an 80 bp long sequence that contains the cohesive ends of TaqI and NdeI.

The BglII-NdeI large fragment of pMF-5516 and the BglII-Taq fragment of pJBF-5401 were isolated. The 80 bp synthetic fragment was ligated to the BglII-Taq fragment from pJBF-5401 which was then ligated to the BglII-NdeI large fragment from pMF-5516. The resulting expression vector, pMF-5531, contains the complete deo P1-P2 system (including the authentic RBS), the NdeI restriction site and the hSOD gene. It directs low level expression of an hSOD analog protein.

Figure 5:
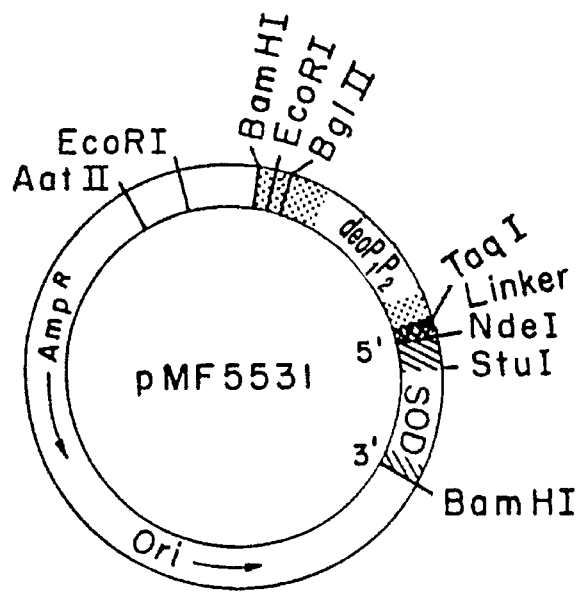
Figure 5:
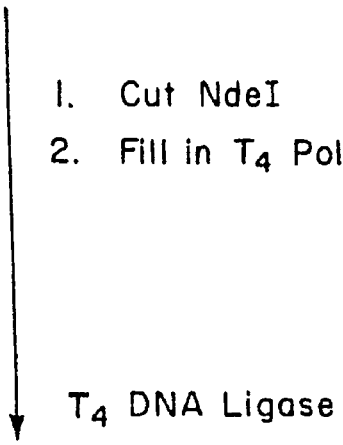
Figure 5:
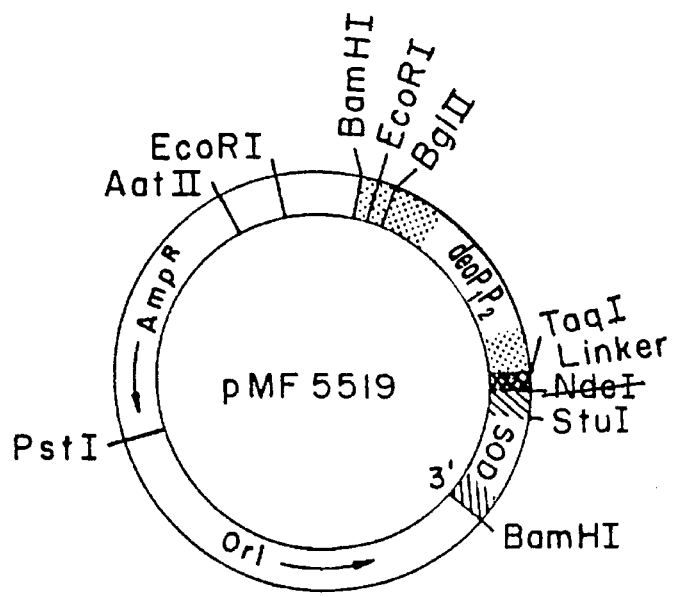

FIG. 5: Construction of pMF-5519—Extension of the Ribosomal Binding Site

Plasmid pMF-5531 was treated with NdeI, filled-in with $T_4$ DNA polymerase and self-ligated. This has the effect of increasing the distance between the ribosomal binding site and the first ATG by 2 base pairs. This new plasmid, designated pMF-5519, contains in 5' to 3' order the deo P1-P2 promoter, the extended RBS-ATG distance, and the hSOD gene. It directs high level expression of an hSOD analog protein.

Figure 6:
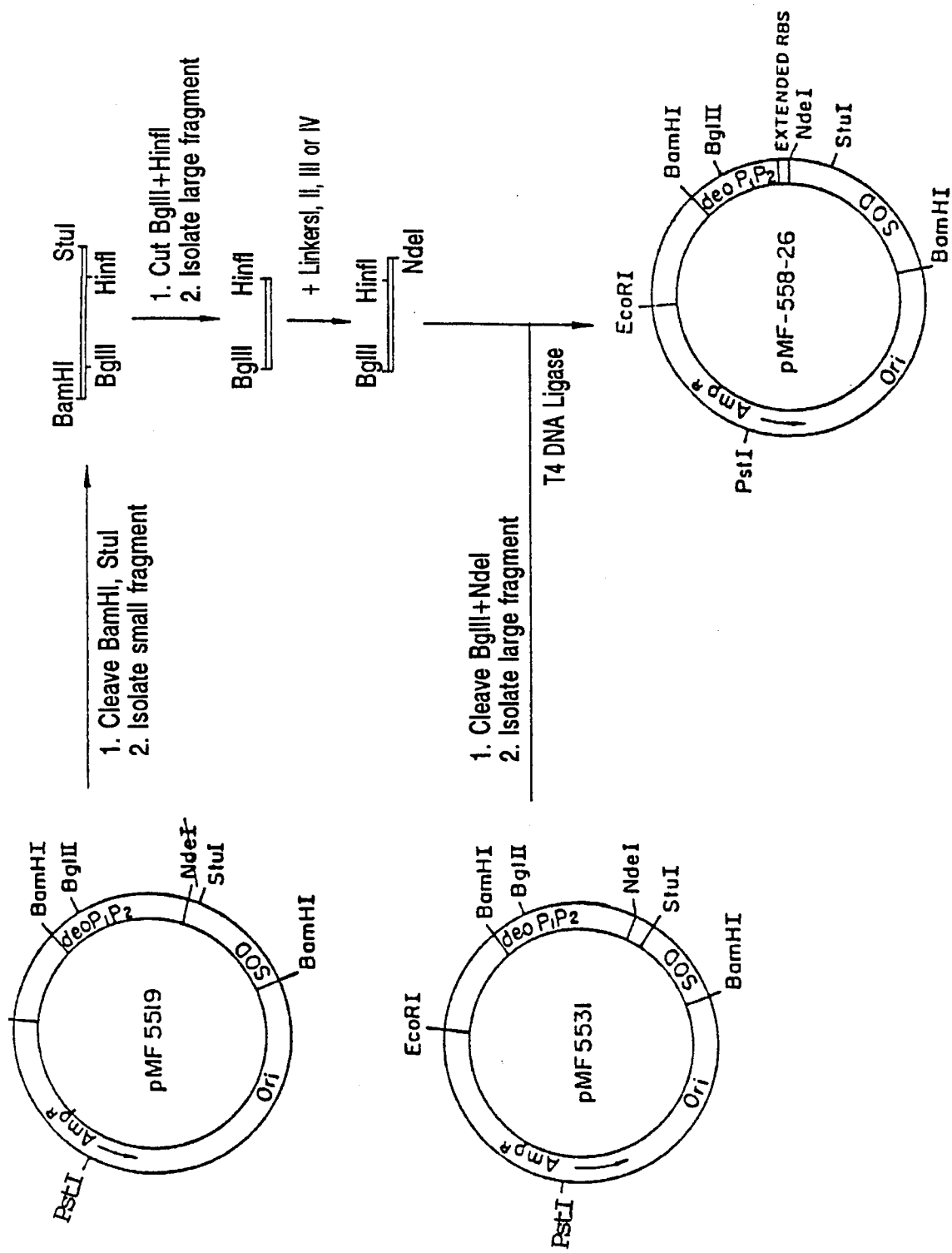

FIG. 6: Further extensions of deo P1-P2 ribosomal binding site

Plasmid pMF-5519 was cleaved with StuI and BamHI and a 1000 bp fragment containing the deo P1-P2 operator promoter region was isolated and incubated with BglII and HinfI to produce a 540 bp BglII-HinfI fragment. Four different synthetic linkers were prepared for attachment to this BglII-HinfI fragment to produce a series of four plasmids which differ from one another in the distance between the ribosomal binding site and the first ATG.

To achieve this end, the following eight single stranded synthetic DNA sequences were synthesized. Complementary strands were annealed producing four synthetic double stranded DNA linkers designated I, II, III and IV.

```
Hi n f I
    AATATACA        Synthetic linker I
       TATGTAT      (7–8 bp extension)
          NdeI Hin f I
    AATATATCA       Synthetic linker II
        TATAGTAT    (8–9 bp extension)
            NdeI Hin f I
    AATATCA         Synthetic linker III
        TAGTAT      (6–7 bp extension)
           NdeI Hin f I
    AATCTAGACA      Synthetic linker IV
        GATCTGTAT   (9–10 bp extension)
              NdeI
```

The four synthetic linkers, I, II, III and IV, all have "sticky ends" consisting of a HinfI site and an NdeI site.

Each linker was allowed to anneal separately to the BglII-HinfI fragment from pMF-5519 and then ligated, producing in each case a novel BglII-NdeI fragment. Then each fragment was annealed separately to the large BglII-NdeI fragment from pMF-5531 and ligated. The resulting plasmids contain an extended RBS. At present only 2 of these 4 constructions, using linkers I and IV, have been sequenced and the sequence verified. The corresponding plasmids, designated pMF-558-26 (linker I) and pMF-5536 (linker IV) respectively, have been transformed in Sϕ732 where they both direct low level expression of an hSOD analog protein.

Figure 7:
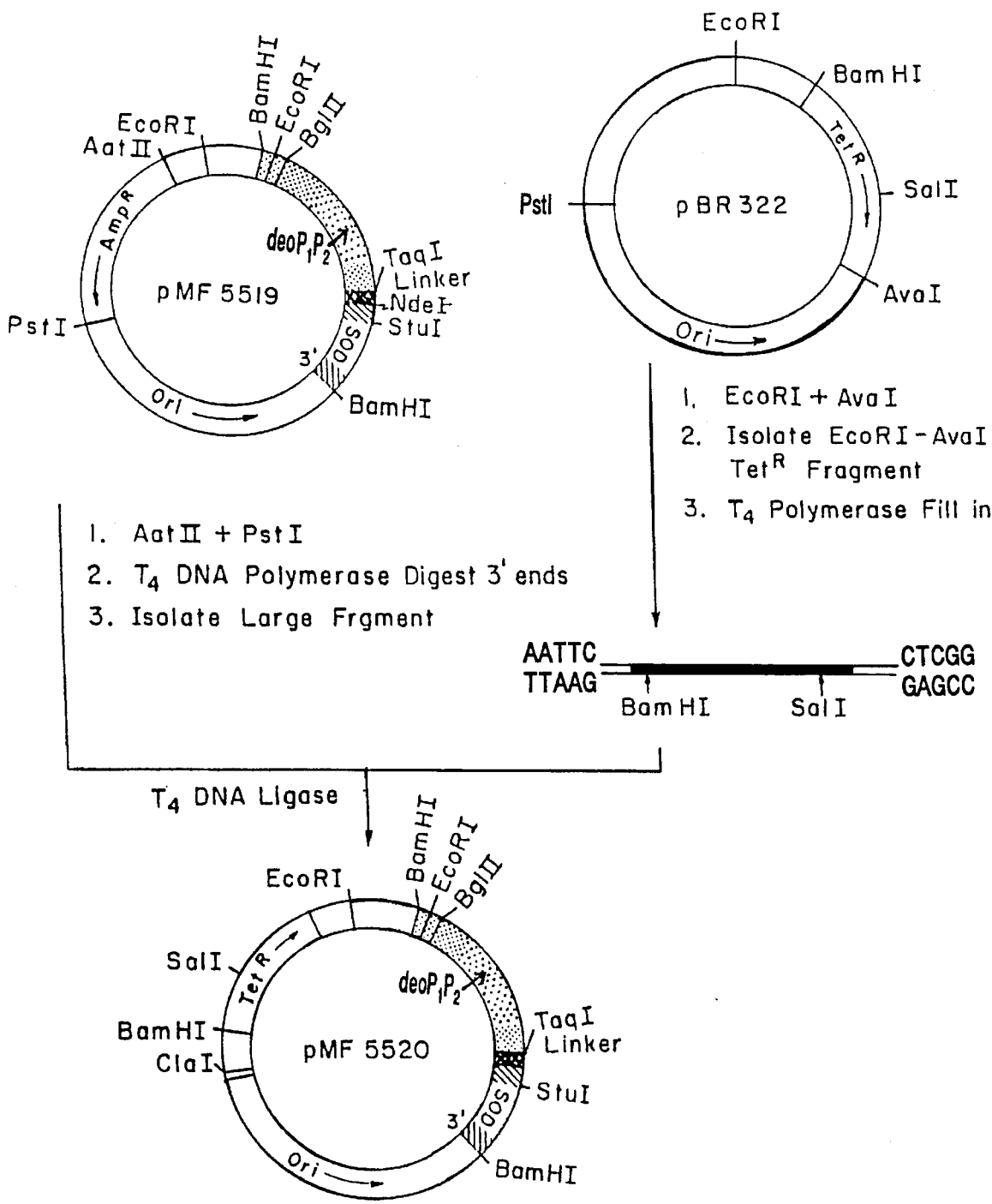

FIG. 7: Construction of pMF-5520 pMF-5519 (which bears the ampicillin resistance gene) was cleaved with AatII and PstI and the 3' ends made flush by digestion with $T_4$ DNA polymerase. This cleavage removes the ampicillin resistance gene. A 1450 bp fragment containing the tetracycline resistance gene from pBR322 was isolated by cleavage with EcoRI and AvaI restriction endonucleases and the 5' ends filled in by $T_4$ DNA polymerase to generate flush ends. The 1450 bp fragment was ligated to the purified pMF-5519 fragment, producing a novel tetracycline-resistant plasmid designated pMF-5520 which contains, in 5' to 3' order, the deo promoter and the hSOD gene. This plasmid directs high level expression of an hSOD analog protein.

Figure 8:
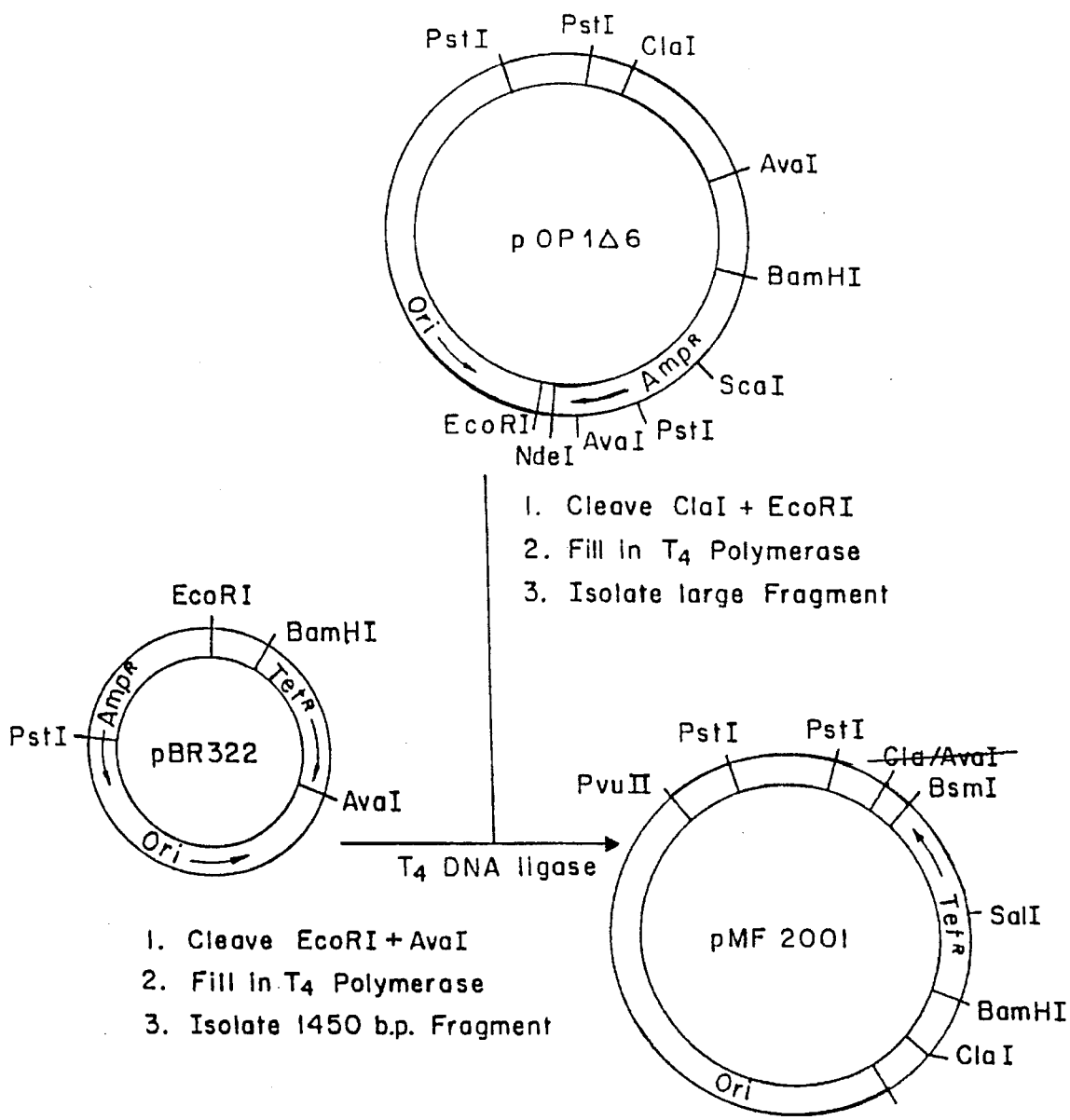

FIG. 8: Construction of pMF-2001

Plasmid pOP1Δ6 is a high copy number plasmid constructed as described by D. H. Gelfand et al., PNAS 15: 5869–5873 (1978) and by M. Muesing et al., Cell 24: 235 (1981). It was cleaved with ClaI and EcoRI, filled-in with $T_4$ DNA polymerase and the resulting large fragment was ligated to the 1450 bp fragment (containing the tetracycline-resistance gene) from pBR322 by cleaving with EcoRI and AvaI and filling-in with $T_4$ polymerase.

This effectively replaces the ampicillin-resistance gene of pOP1Δ6 with the tetracycline-resistance gene. The new high copy number tetracycline-resistant plasmid produced was designated pMF-2001.

Figure 9:
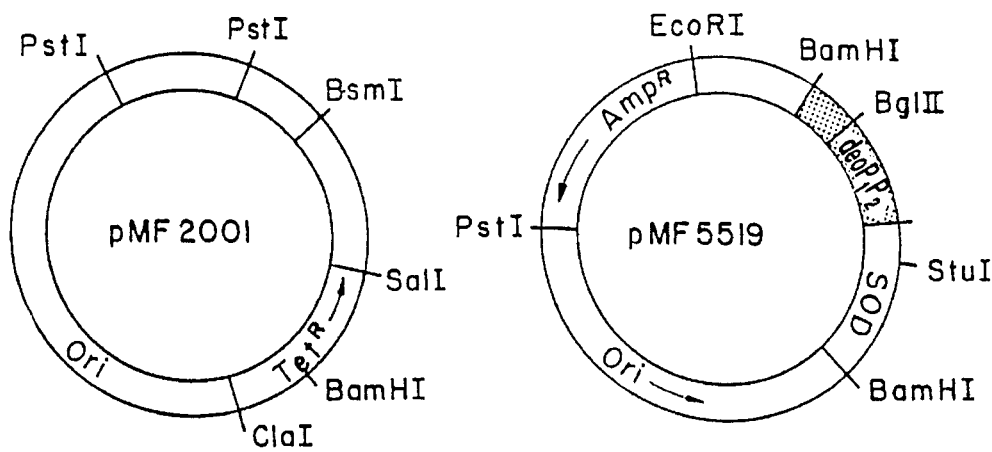
Figure 9:
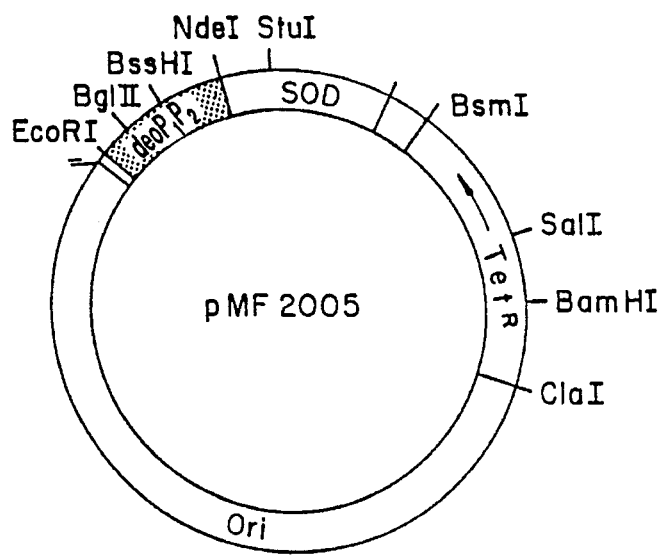

FIG. 9: Construction of pMF-2005

Plasmid 5519 was digested with BamHI, filled-in with $T_4$ DNA polymerase and the resulting small fragment (containing the deo P1-P2 operator/promoter region and the hSOD gene) was ligated to the large fragment obtained from plasmid pMF-2001 after PstI digestion and $T_4$ DNA polymerase removal of 3' ends. This transferred the whole hSOD gene under the control of the deo P1-P2 operator/promoter region into the high copy number plasmid. The resulting plasmid, designated pMF-2005 is a high copy number plasmid which directs an extremely high level of expression of an hSOD protein analog under the control of the deo P1-P2 operator/promoter. Plasmid pMF-2005 has been deposited with the ATCC in Rockville, Md. 20852 U.S.A. under ATCC Accession No. 67362 pursuant to the provisions of the Budapest Treaty.

Figure 10:
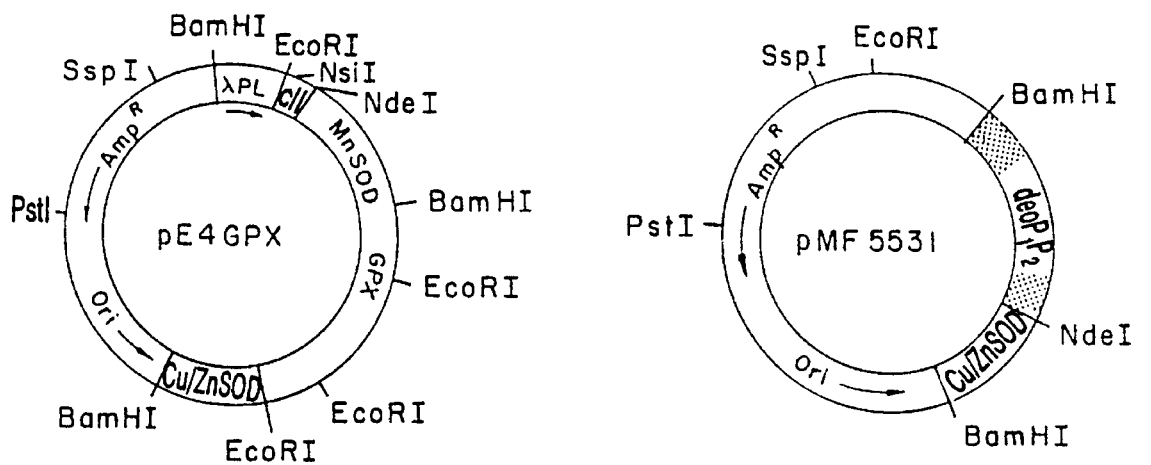
Figure 10:
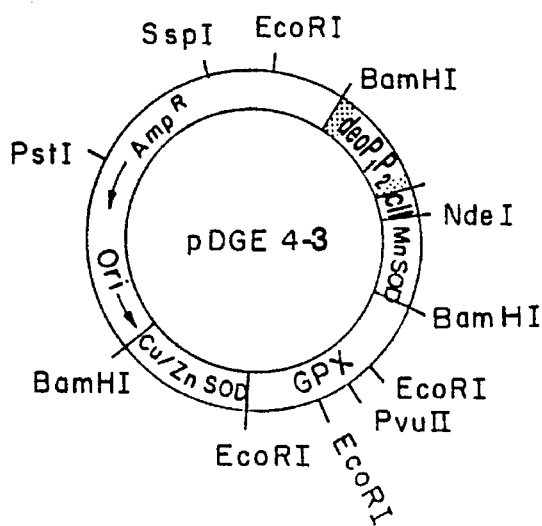

FIG. 10: Construction of pDGE4-3

Figure 28:
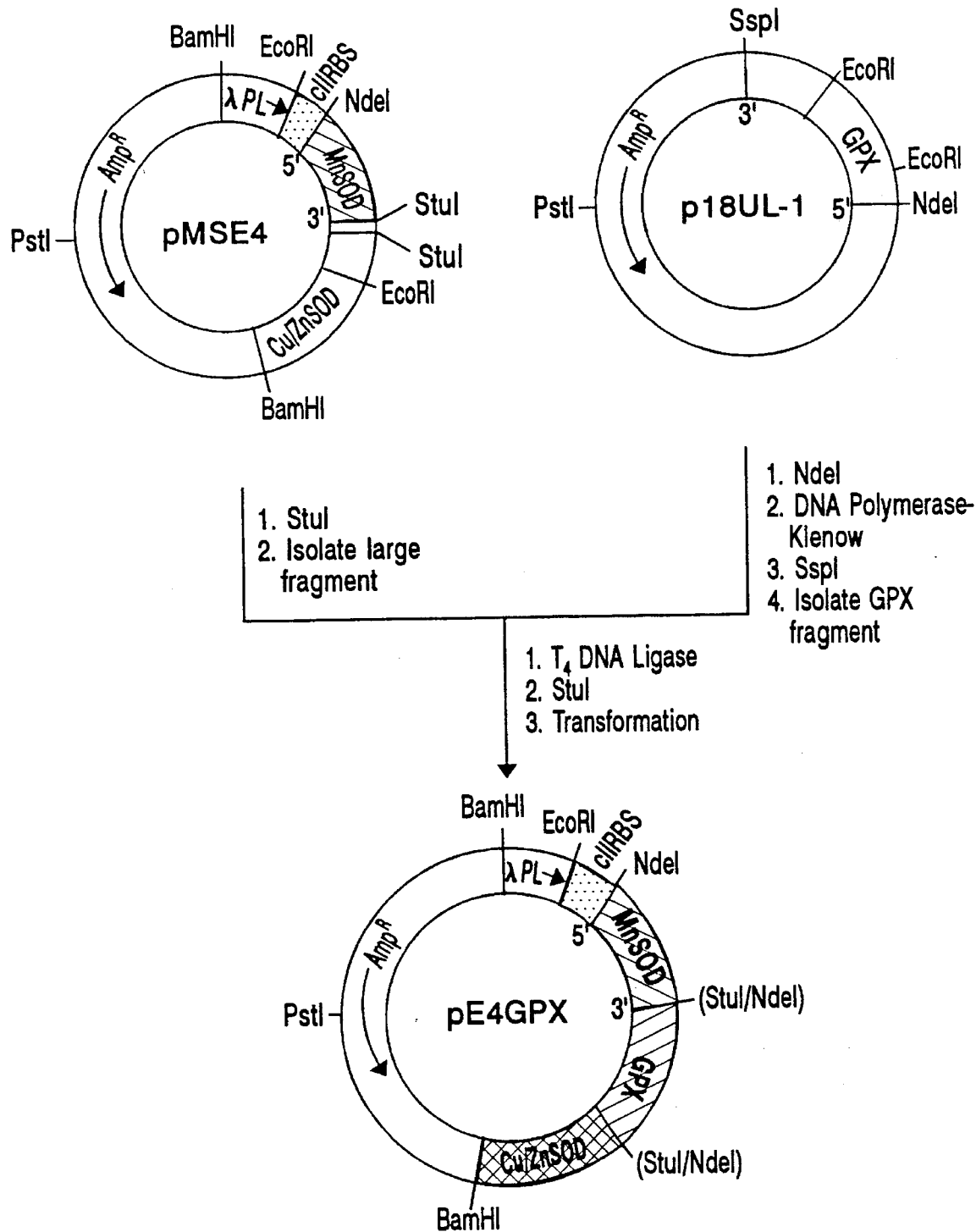

Plasmid pE4GPX was produced from plasmid pMSE4 (ATCC Accession No. 53250) as shown in FIG. 28. This plasmid expresses an MnSOD-GPX fused protein under the control of the λ $P_L$ promoter and cII ribosomal binding site. It was digested with NsiI, the 3' ends were removed with $T_4$ DNA polymerase, and then digested with SspI to remove the λ $P_L$ promoter. The large fragment (4000 bp) was isolated, and was ligated to the 1300 bp deo promoter obtained from pMF-5531 (FIG. 4) by NdeI digestion, Klenow fill-in and SspI digestion). The new plasmid, designated pDGE4-3, contains in 5' to 3' order the deo P1-P2 operator/promoter sequence, approximately 50 bp of the cII ribosomal binding site, approximately 450 bp of the MnSOD sequence and the GPX sequence.

pDGE4-3 directs the synthesis of a large amount of MnSOD-GPX fused protein under the control of the deo P1-P2 promoter and the cII RBS.

Figure 11:
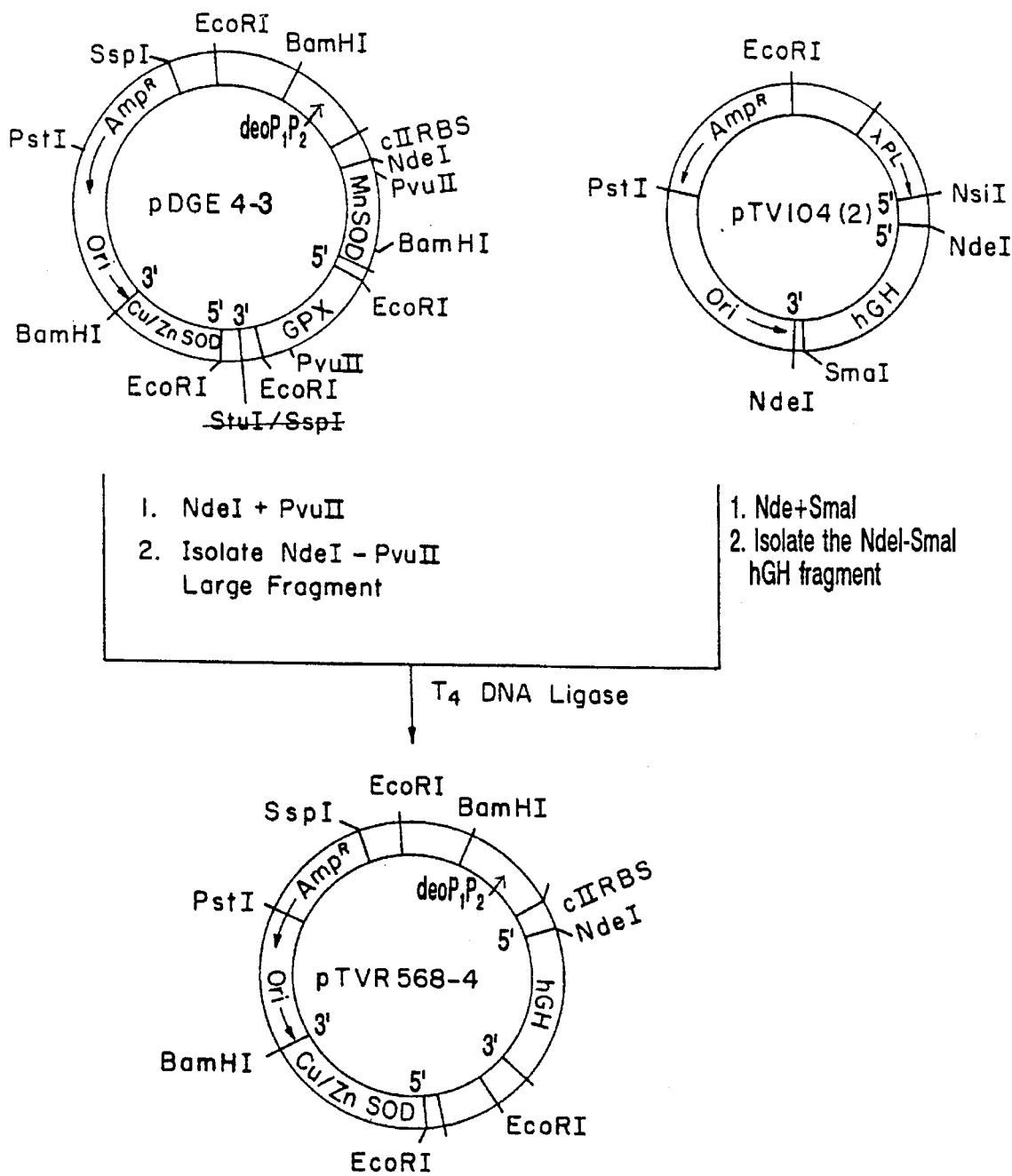

FIG. 11: Construction of pTVR 568-4

Plasmid pTV104(2) (ATCC Accession No. 39384) was digested with NdeI and SmaI to obtain the small NdeI-SmaI fragment which contains the entire hGH sequence. This was ligated to the large NdeI-PvuII fragment obtained from pDGE4-3. The new plasmid, designated pTVR 568-4, contains in 5' to 3' order the deo P1-P2 promoter, approximately 50 bp of the cII ribosomal binding site and the hGH coding sequence. pTVR 568-4 directs the synthesis of large amounts of an hGH analog under the control of the deo P1-P2 promoter and the cII RBS.

Figure 12:
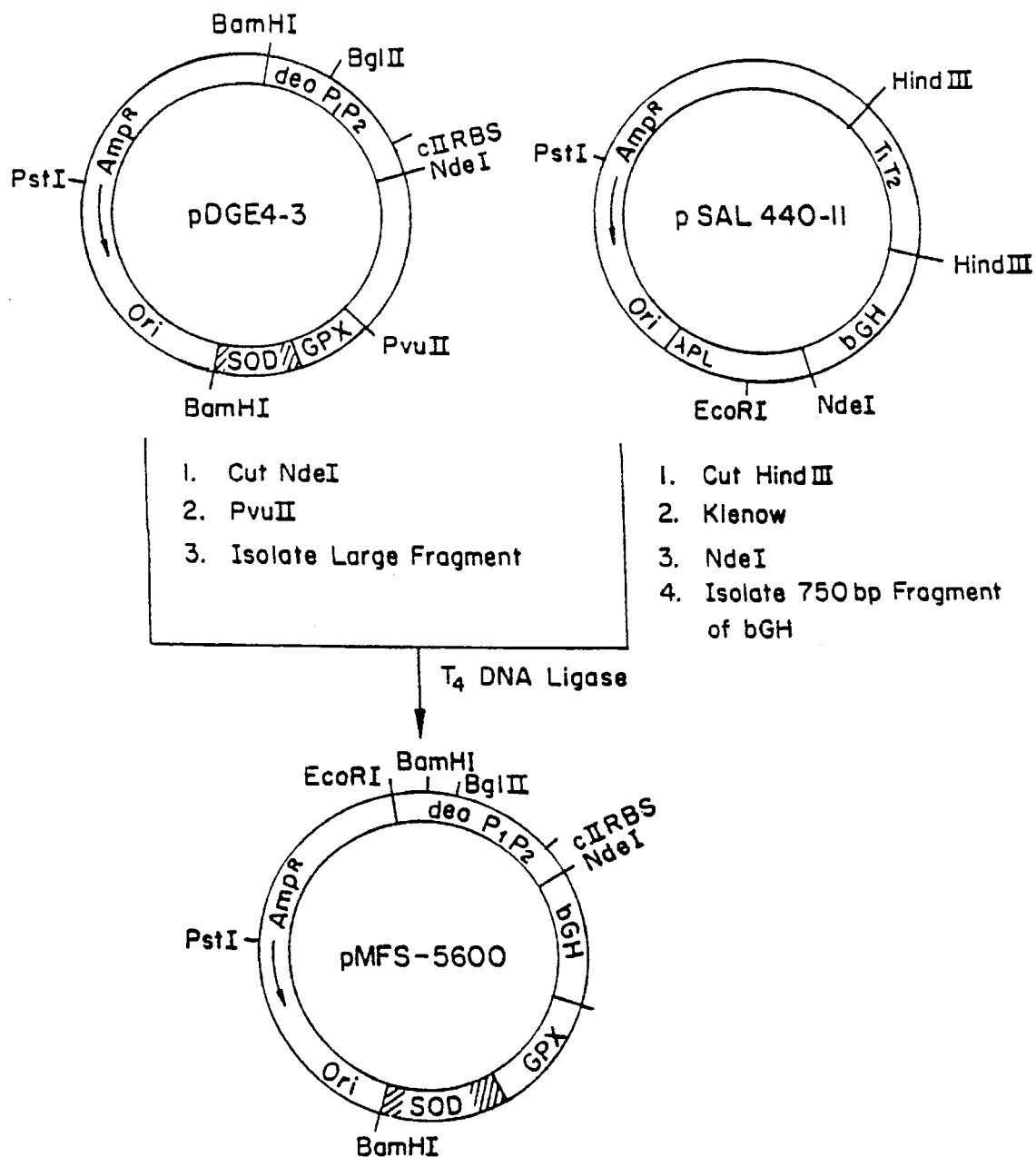

FIG. 12: Construction of pMFS-5600—a plasmid producing bGH under the control of deo P1-P2 operator/promoter region Plasmid pDGE4-3 (FIG. 10) was cleaved with NdeI and PvuII and the large NdeI-PvuII fragment was isolated and ligated with $T_4$ ligase to a 750 bp bGH sequence obtained as follows. Plasmid pSAL 440-11 is identical to plasmid pSAL 440-22 (FIG. 24), namely a different isolate from the same transformation. The bGH sequence was obtained from pSAL 440-11 by treatment with HindIII, fill-in with Klenow DNA polymerase large fragment followed by digestion with NdeI.

The resulting plasmid designated pMFS-5600 contains in 5' to 3' order the deo P1-P2 promoter, the authentic deo RBS, approximately 50 bp of the cII RBS, the bGH gene, part of the GPX gene and the Cu—Zn hSOD gene. Plasmid pMFS-5600 directs the synthesis of a bGH analog protein under the control of the deo P1-P2 and the modified cII RBS.

Figure 13:
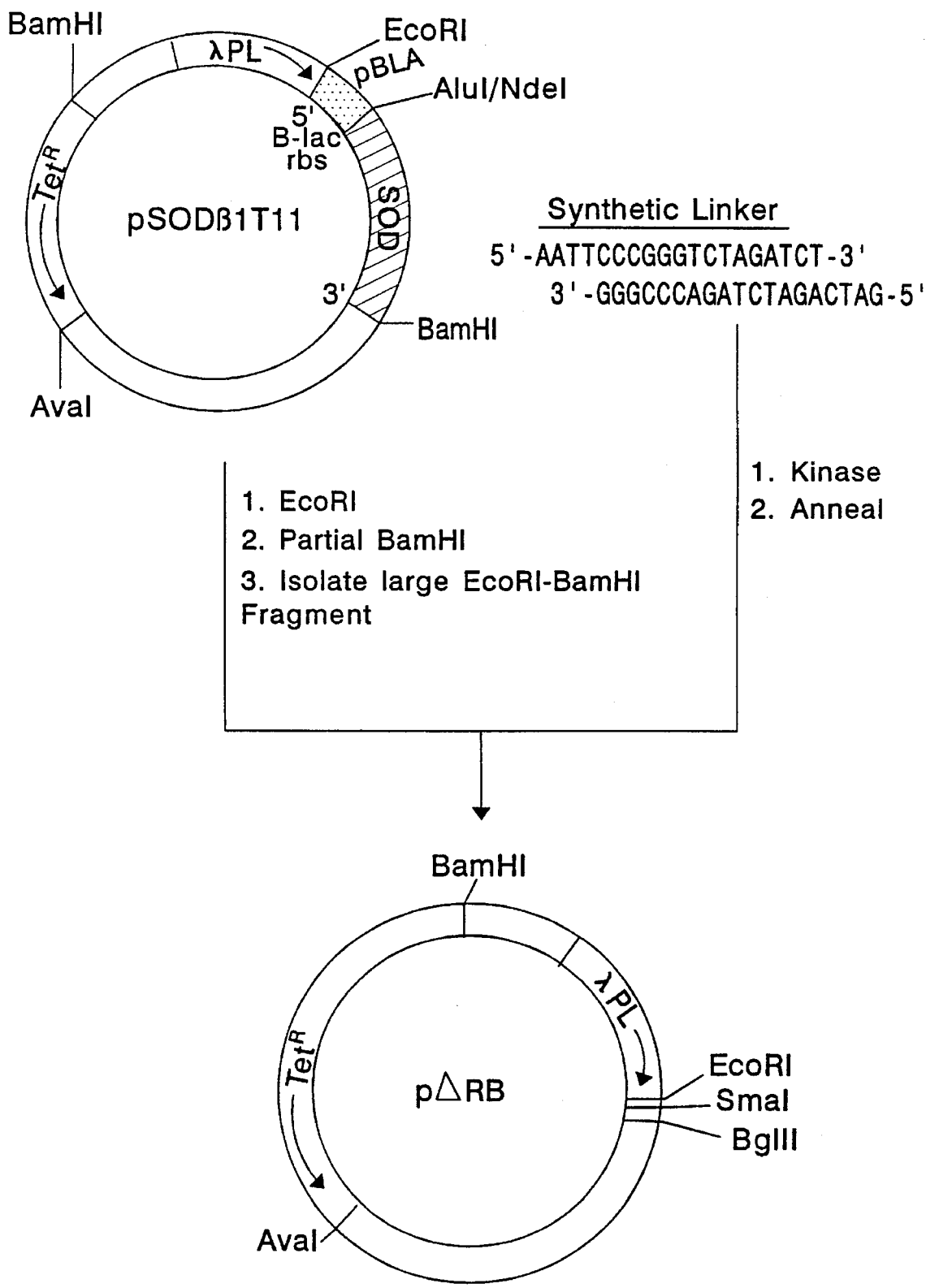

FIG. 13: Construction of pΔRB

Plasmid pSODβ$_1$T11 (ATCC Accession No. 53468) directs expression of an analog of human Cu—Zn SOD. (The construction of this plasmid was described in coassigned U.S. Pat. No. 4,742,004 and in European Patent Office publication No. 173,280 both of which references are hereby incorporated by reference.) It contains, in 5' to 3' order, the λ $P_L$ promoter, the β-lactamase promoter, the β-lactamase ribosomal binding site and the Cu—Zn hSOD gene. The large fragment produced after EcoRI and partial BamHI digestion is deleted both for the β-lactamase promoter-ribosomal binding site and the SOD gene. A synthetic linker was constructed to introduce new restriction sites, and ligated to the above fragment. This produced pΔRB, which contains the λ PL promoter immediately upstream from the EcoRI, SmaI, XbaI and BglII sites, in 5' to 3' order.

Figure 14:
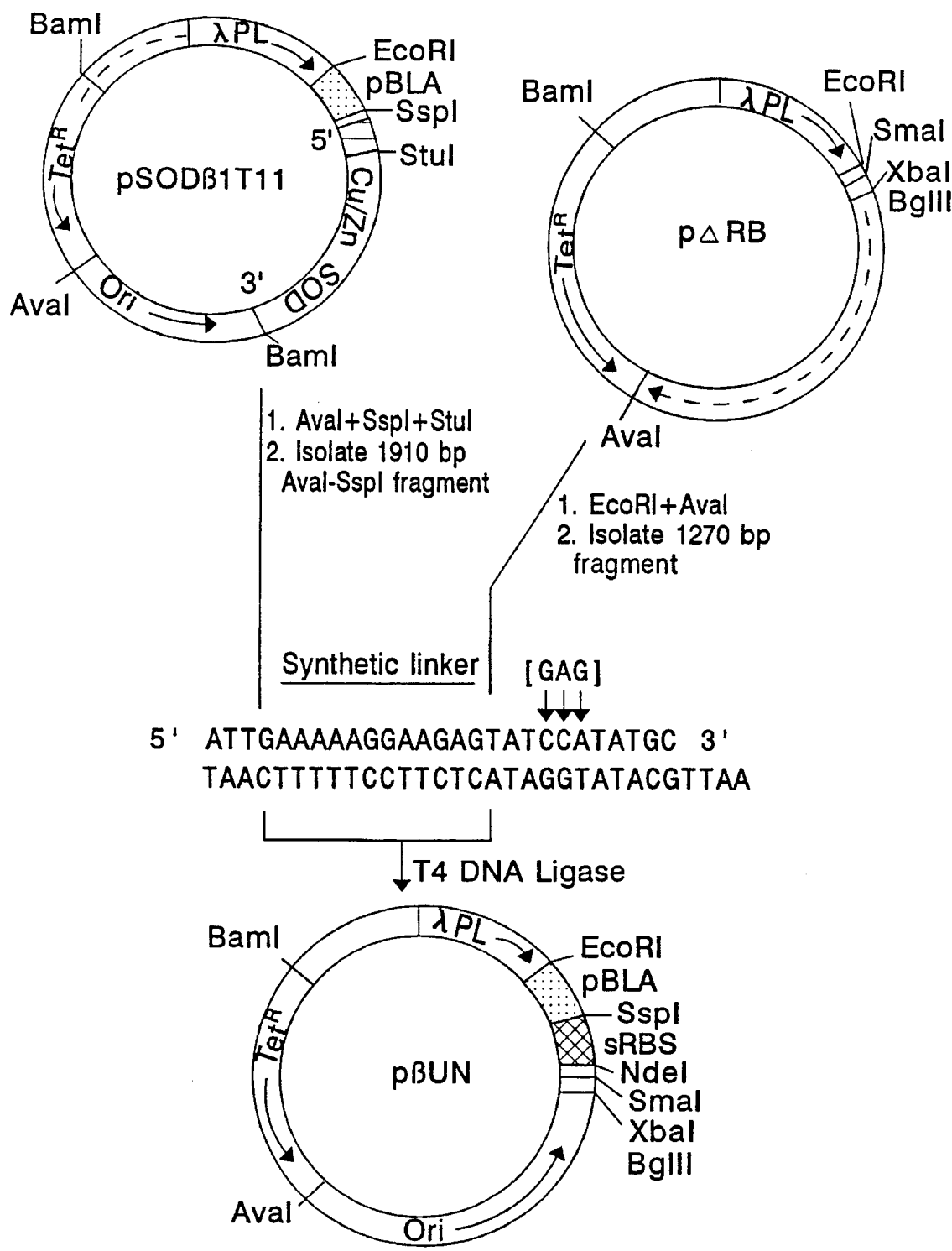

FIG. 14: Construction of pβUN—a general purpose expression vector

Plasmid pSODβ$_1$T11 was digested with AvaI, SspI and StuI and the 1910 bp AvaI-SspI fragment was isolated. This fragment was ligated to the synthetic SspI-EcoRI fragment shown and to the 1270 bp EcoRI-AvaI fragment from pΔRB. The sequence of the synthetic linker differs from the sequence of the "natural" β-lactamase RBS at three nucleotide sites. The three nucleotides indicated in the synthetic linker show the base pair changes at the 3' end of the β-lactamase RBS (CCA replaces GAG). This eliminates the first possible ATG (C replaces G) and the two other base pair changes form an NdeI site (CA replaces AG). Otherwise the synthetic RBS is identical to the β-lactamase RBS. This construction produced the new plasmid pβUN which contains, in 5' to 3' order, the λ $P_L$ promoter, the β-lactamase promoter, the synthetic β-lactamase RBS with the unique NdeI site followed by the SmaI, XbaI and BglII sites.

Figure 15:
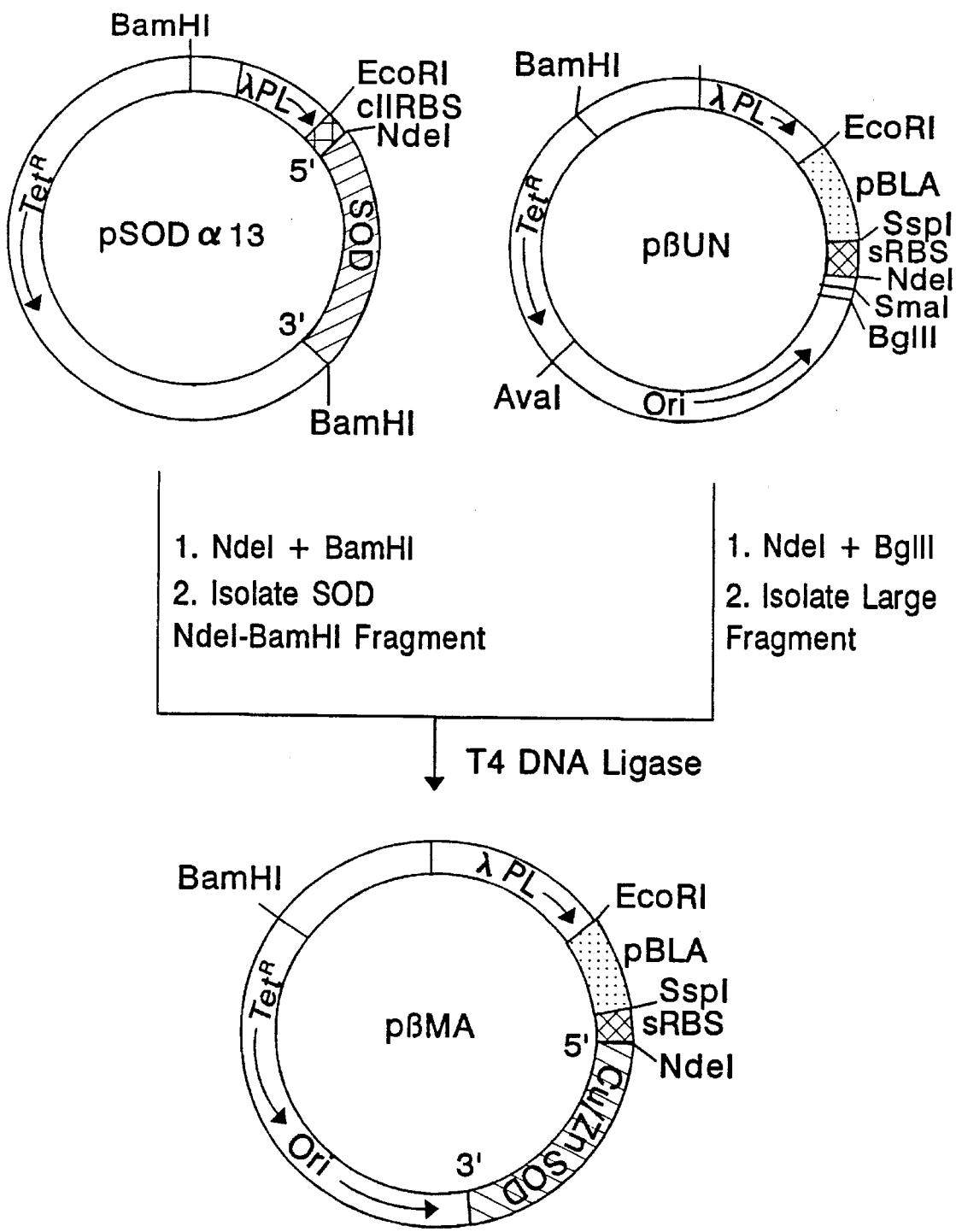

FIG. 15: Construction of pβMA

The NdeI-BamHI fragment from pSODα13 (see FIG. 3—description) containing an hSOD cDNA was inserted into the NdeI-BglII large fragment of pβUN as shown. The plasmid produced, designated pβMA, expressed the hSOD analog at low levels. The only difference in DNA sequence between pSODβ$_1$T11 and the newly obtained plasmid pβMA is in 3 base pairs at the 3' end of the ribosomal binding site (see descriptions to FIGS. 14 and 16).

Figure 16:
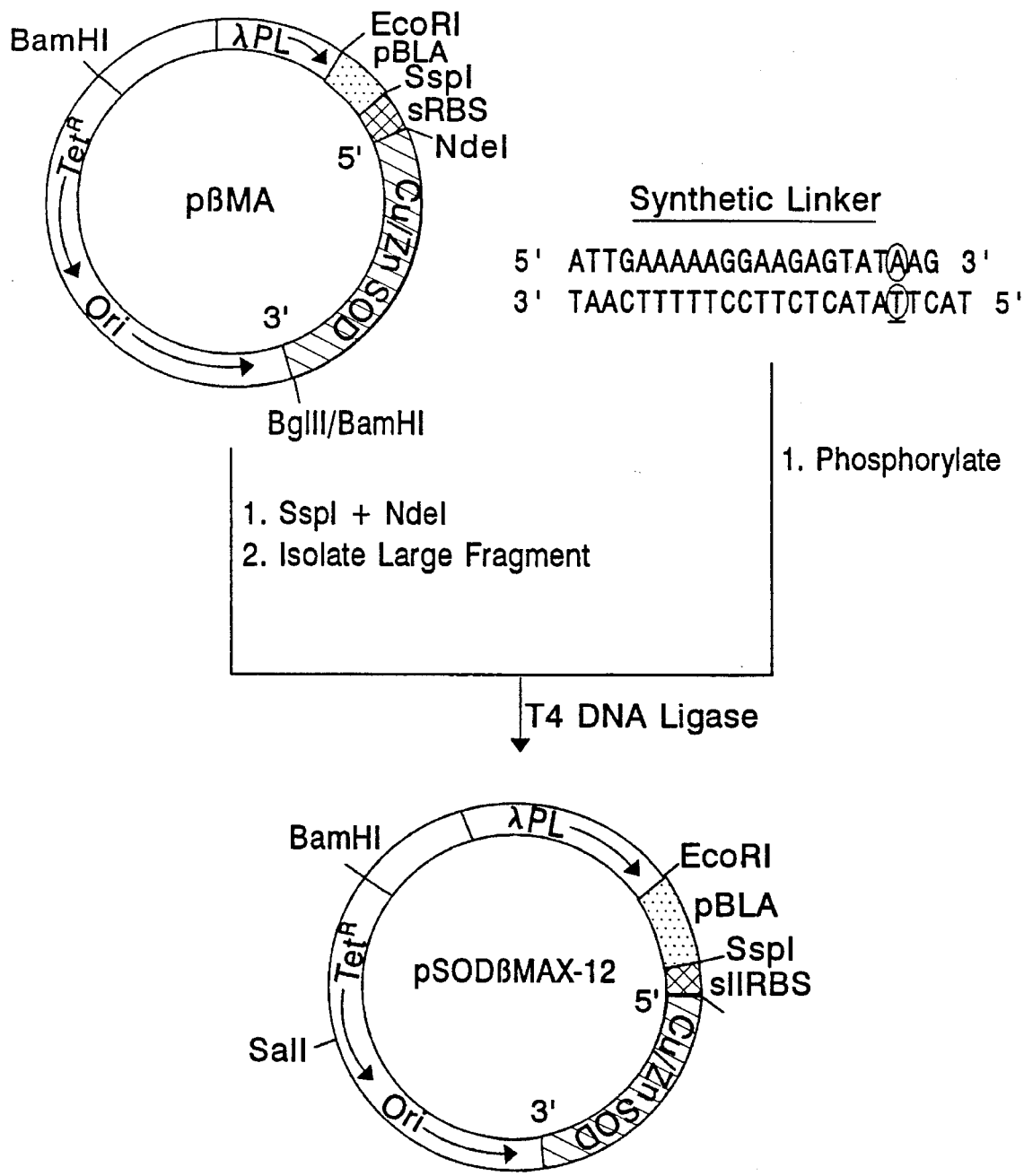

FIG. 16: Construction of pSODβMAX-12

Plasmid pβMA was cleaved with SspI and NdeI to remove the synthetic β-lactamase RBS, and the large SspI-NdeI fragment was ligated to the synthetic linker shown, forming the novel plasmid pSODβMAX-12. The synthetic linker consists of the β-lactamase RBS with one base pair modification at the 3' end. This modification creates a synthetic (sII) β-lactamase RBS with one base changed (A replaces G) from the authentic β-lactamase RBS, thus eliminating the first possible ATG initiation codon. The base pair changes can be summarized as follows:

Authentic sequence in pSODβ$_1$T11    AAGGAAGAGTATGAGTATG
Synthetic sequence in pβMA           AAGGAAGAGTATCCATATG
                                              ---------
                                              NdeI site
Synthetic (sII) sequence             AAGGAAGAGTATAAGTATG
 in pSODβMAX-12

Plasmid pSODβMAX-12 thus differs from plasmid pSODβT11 in one base pair only and directs high level expression of an SOD analog protein. Plasmid pSODβMAX-12 has been deposited in *Escherichia coli* strain A4255 under ATCC Accession No. 67177.

Figure 17:
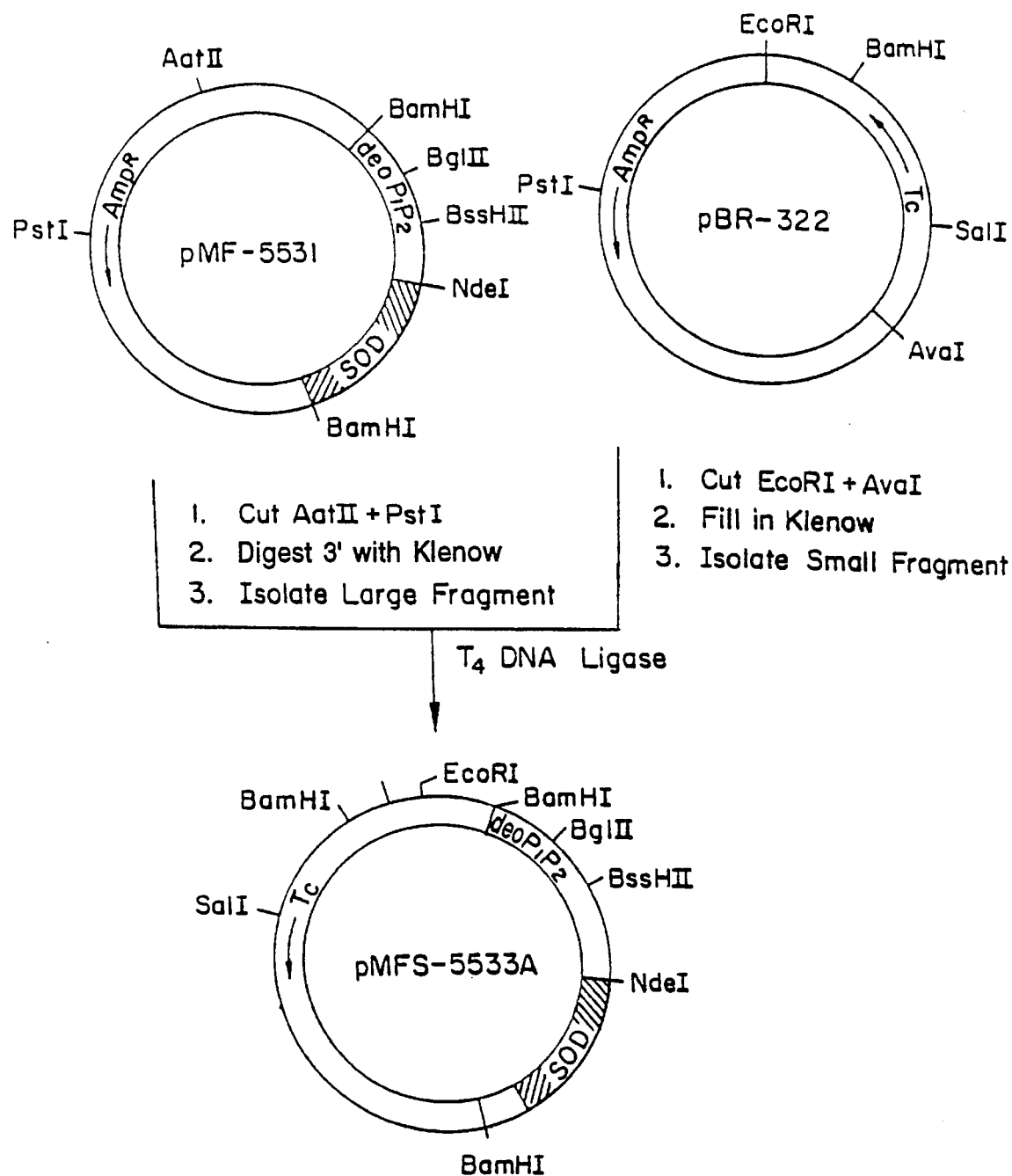

FIG. 17: Construction of pMFS-5533A

Plasmid pMF-5531 (shown in FIG. 4) was cleaved with AatII and PstI and then treated by Klenow to remove the 3' ends. This cleavage removes the ampicillin resistance gene. The large fragment produced was ligated to the small pBR322 fragment, bearing the tetracycline resistance gene, produced by cleaving pBR322 with EcoRI and AvaI, and filling in with Klenow enzyme.

The resulting plasmid designated pMFS-5533A is identical to pMF-5531 except that the ampicillin resistance gene has been replaced with the tetracycline resistance gene; it contains in 5' to 3' order the deo P1-P2 promoter, the NdeI site and the hSOD gene.

Figure 18:
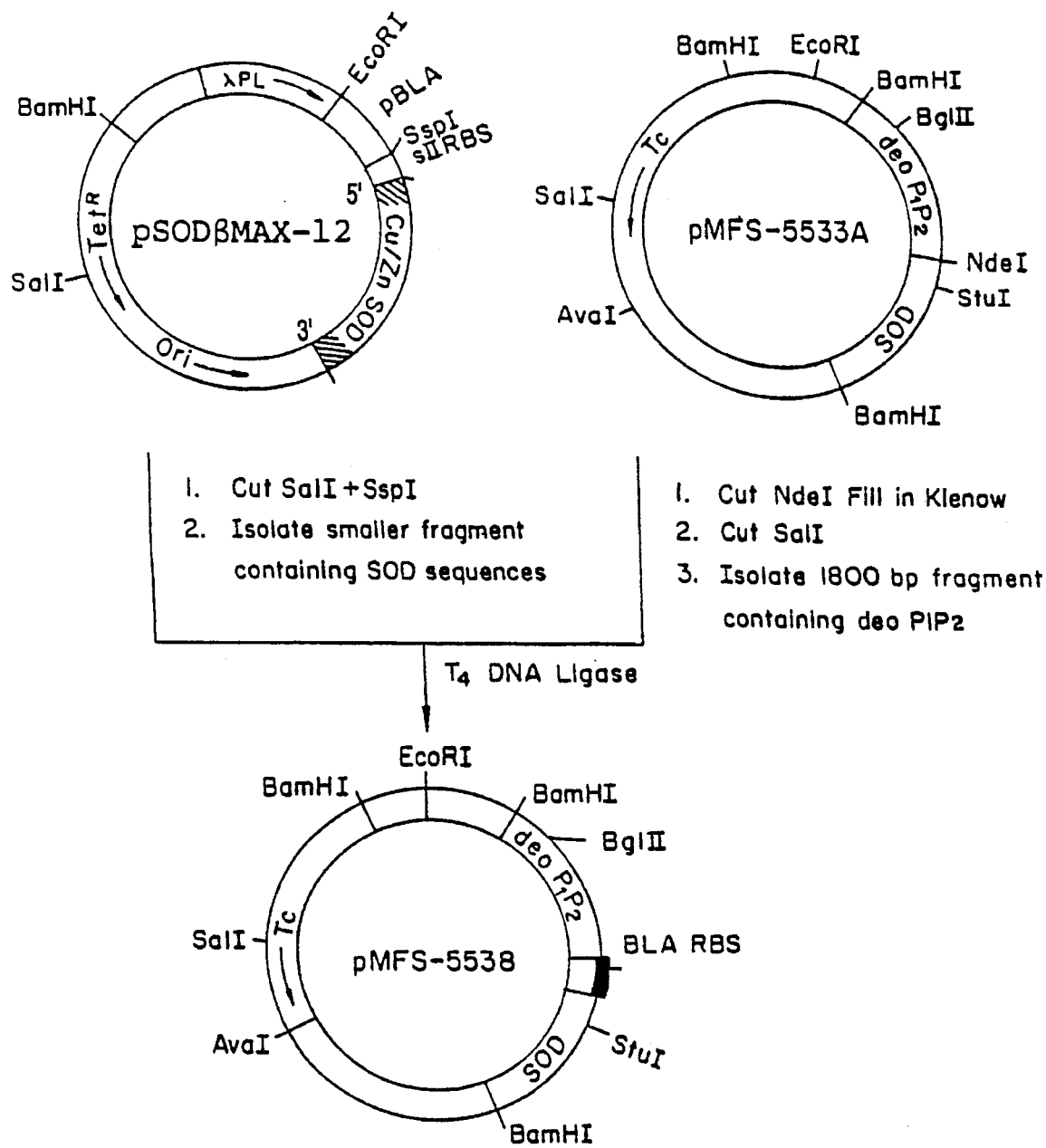

FIG. 18: Construction of pMFS-5538

Plasmid pSODβMAX-12 (obtained as shown in FIGS. 13–16) was cleaved with SalI and SspI and the 2625 bp fragment containing the synthetic β-lactamase RBS and the Cu—Zn SOD gene was obtained. It was ligated to a fragment containing the deo P1-P2, obtained by restriction of pMFS-5533A with NdeI, followed by Klenow fill-in and further digestion with SalI.

The resulting plasmid designated pMFS-5538 contains in 5' to 3' order the deo P1-P2 promoter, the authentic deo RBS, the synthetic β-lactamase ribosomal binding site and the hSOD gene. It expresses an hSOD analog protein at a moderate level.

Figure 19:
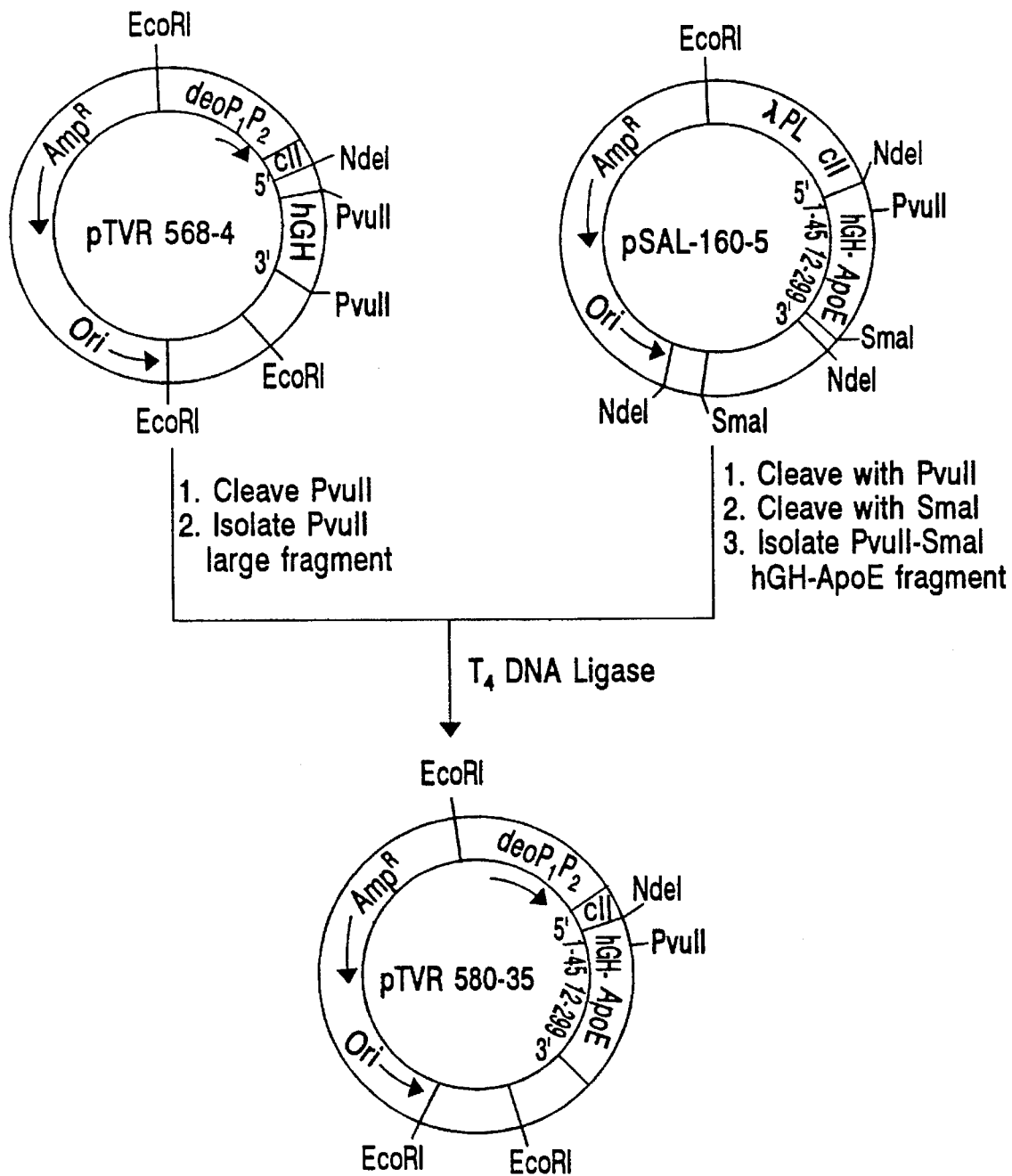

FIG. 19: Construction of pTVR 580-35

Plasmid pSAL-160-5 (constructed as shown in FIGS. 31–34) expresses a fused hGH apolipoprotein E protein where the N terminal consists of the first 45 amino acids of hGH fused to ApoE3 deleted of the first 11 amino acids. The small hGH-ApoE fragment produced by cleaving this plasmid with PvuII and SmaI was ligated into the large fragment produced by PvuII digestion of pTVR 568-4 (FIG. 11). This effectively replaces the hGH sequence in pTVR 568-4 with the hGH-ApoE fused sequence. The resulting plasmid, designated pTVR 580-35 contains, in 5' to 3' order, the deo P1-P2 operator/promoter region, the cII ribosomal binding site and the hGH ApoE fused sequence; it expresses large amounts of a fused hGH ApoE protein under the control of deo P1-P2 and the cII RBS.

Figure 20:
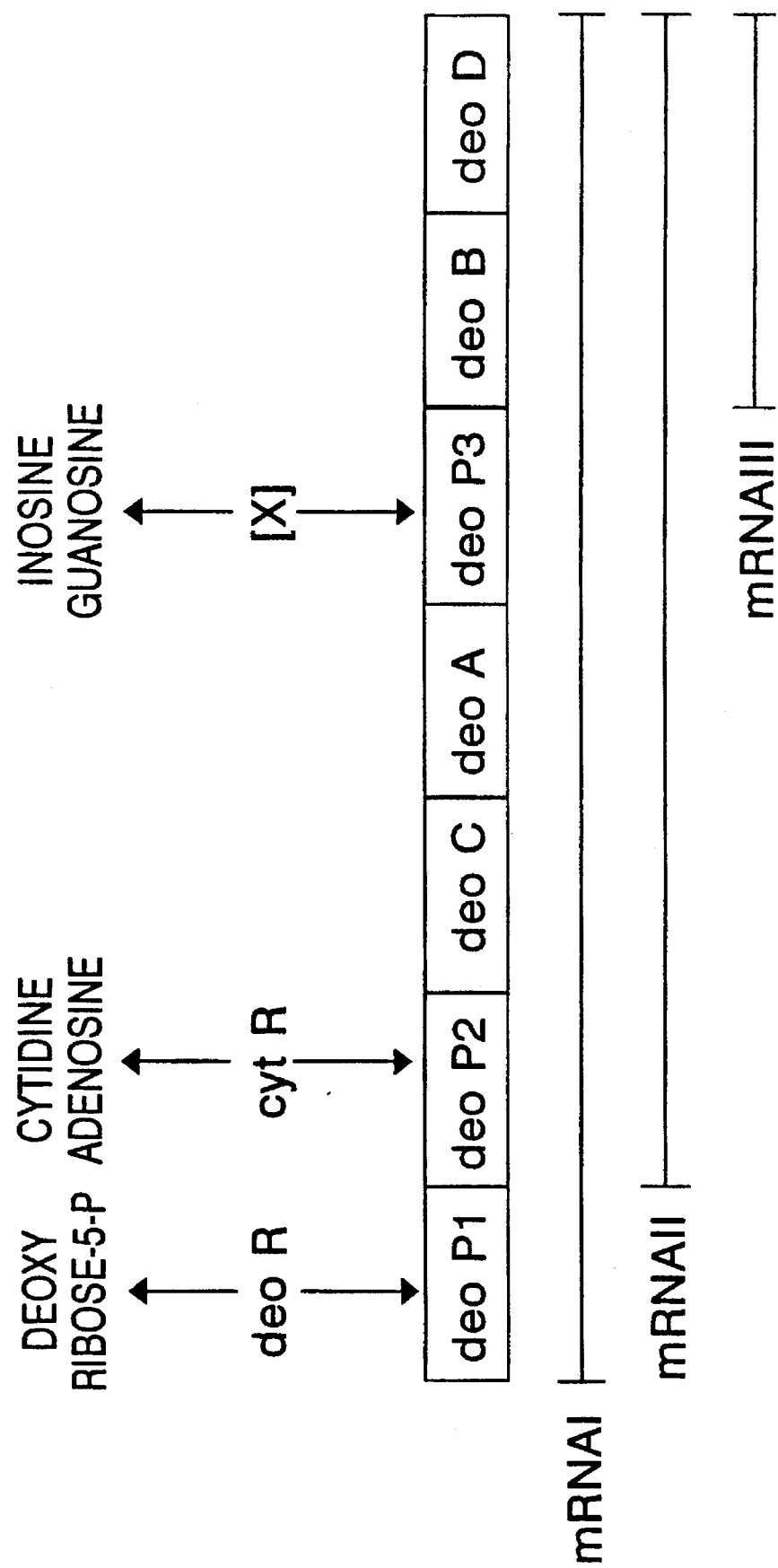

FIG. 20: Schematic map of the deo operon

This Fig. depicts a schematic map of the entire deo operon. The various deo genes code for the following enzymes: deo C, deoxyriboaldolase; deo A, thymidine phosphorylase; deo B, deoxyribomutase; and deo D, purine nucleotide phosphorylase. Three operator/promoter regions have been described: at deo P1, transcription is repressed by the deo R repressor and induced by deoxyribose-5-P; at deo P2, transcription is repressed by the cyt R repressor, induced by cytidine or adenosine and depends on cAMP and CRP; at deo P3, transcription is controlled by unknown protein factors and induced by inosine or guanosine. The cyt R and deo R genes are not linked to the deo operon.

Figure 21:
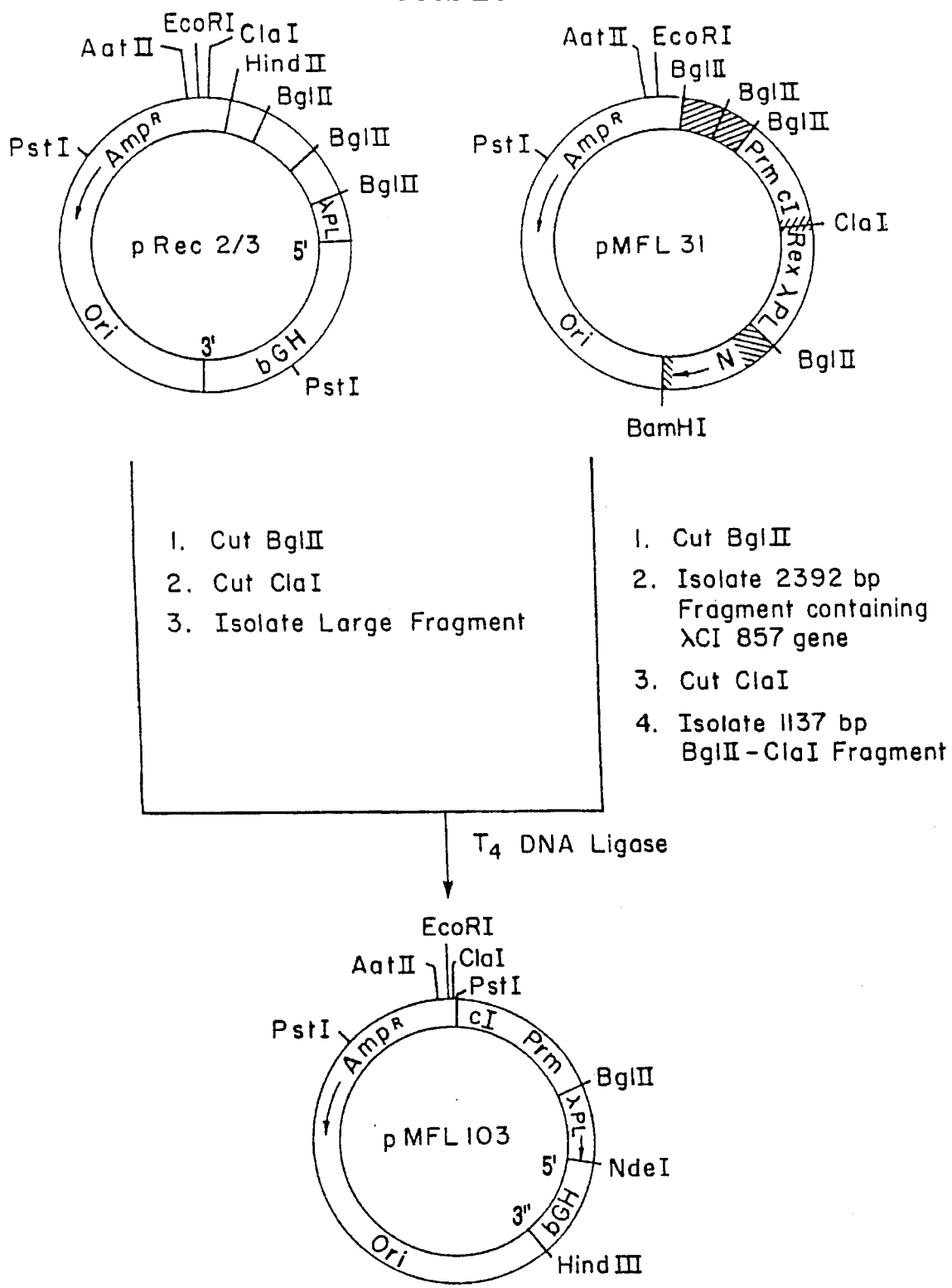

FIG. 21: Construction of pMFL 103

Plasmid pMFL-31 was produced by the insertion of the 5400 bp EcoRI-BamHI fragment of λ DNA (containing the cI 857, Rex A, Rex B and N gene sequences) into pBR322 restricted with EcoRI and BamHI (see Example 8).

The cI 857 BglII-ClaI fragment was removed from pMFL-31 as shown and ligated to pRec ⅔ (ATCC Accession No. 39385) cleaved with BglII and ClaI, to produce the new plasmid pMFL 103, from which the Rex A and Rex B genes have been eliminated.

Figure 22:
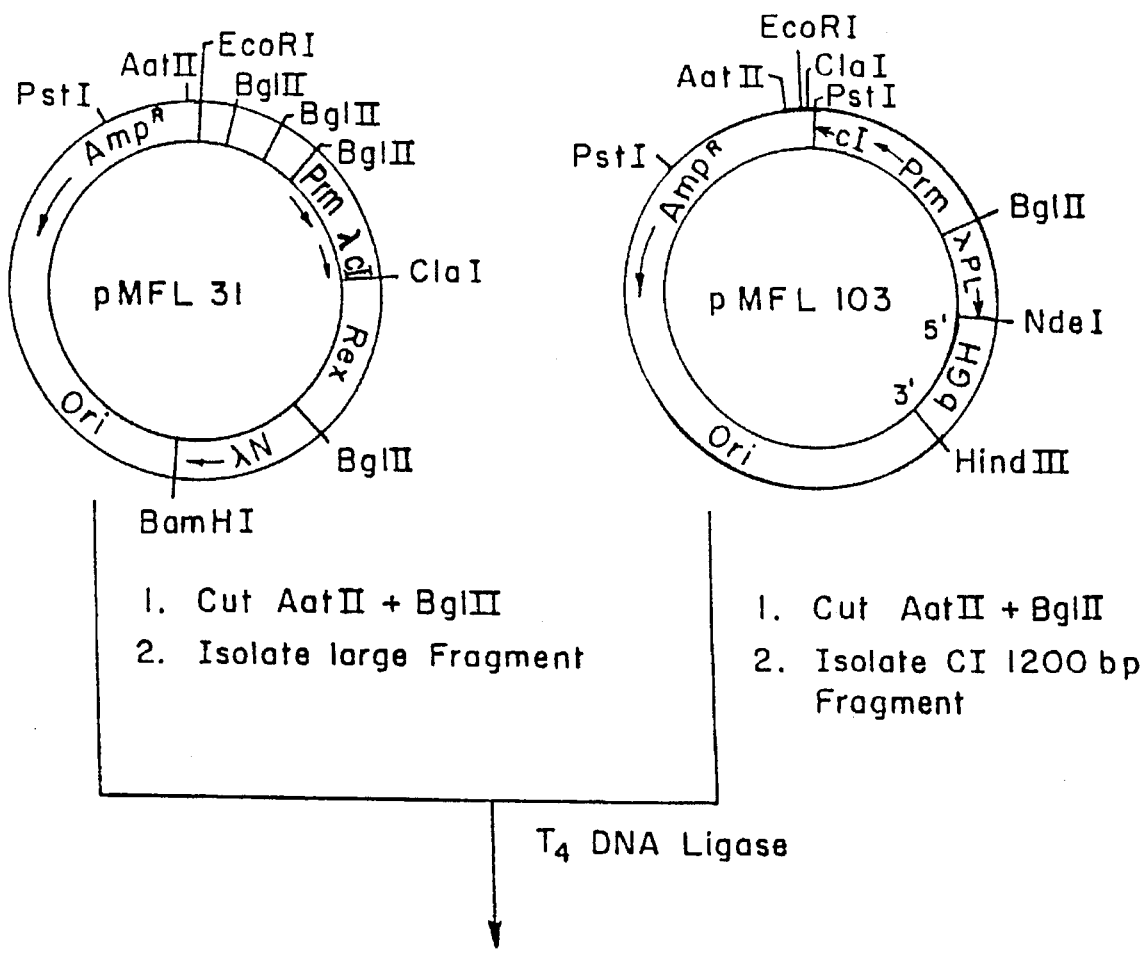
Figure 22:
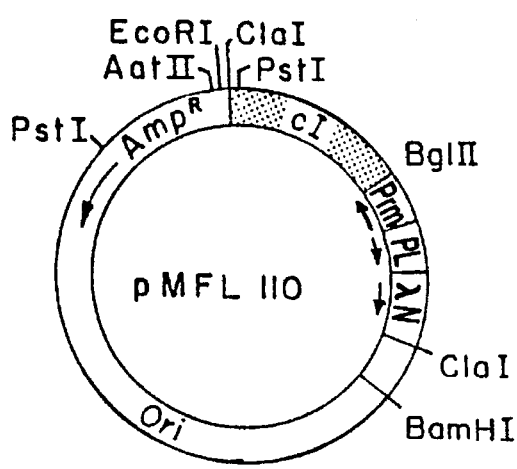

FIG. 22: Construction of pMFL 110

The cI 857 gene was removed from pMFL 103 by AatII-BglII digestion. This was inserted into the large pMFL 31 fragment restricted with the same enzymes. Thus a new plasmid, designated pMFL 110, was produced in which approximately 2500 bp of the Rex A and Rex B genes have been eliminated from pMFL 31 and which has an AatII site upstream from the 5' end of the cI 857 gene. This plasmid, pMFL 110, contains the cI 857 gene (BglII-Aat fragment) upstream from the λ $P_L$ and N genes (on a BglII-BamHI fragment). In this plasmid the λ cI 857 gene is under the control of the authentic Prm promoter.

Figure 23:
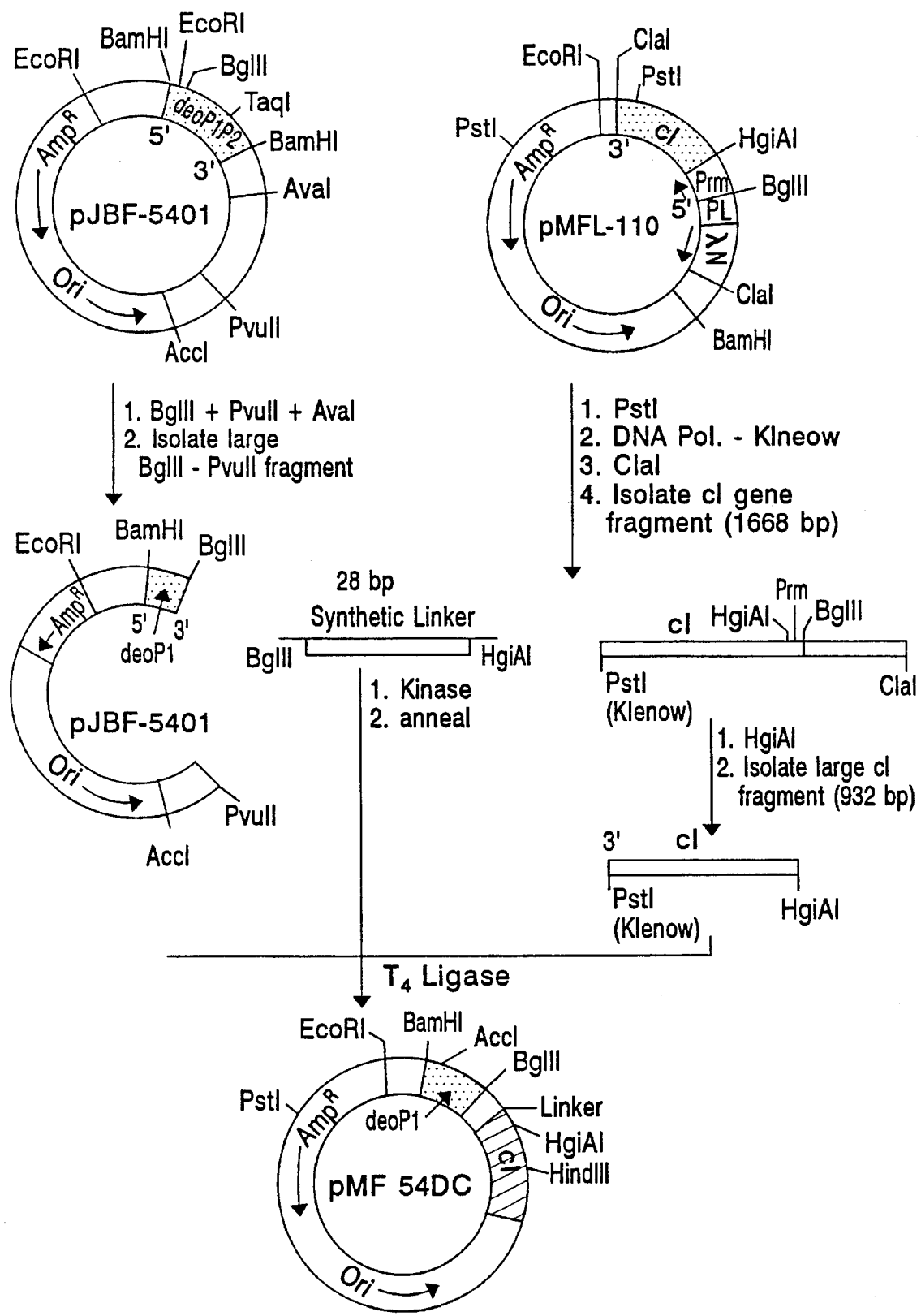

FIG. 23: Construction of pMF-54DC

Plasmid pMFL 110 was cleaved with PstI and the 3' protruding ends digested away with Klenow enzyme. This was followed by ClaI digestion. The PstI (Klenow)-ClaI fragment containing the cI 857 gene, (1668 bp long), was digested with Hgi AI which generates a 932 bp fragment which contains the cI 857 gene lacking 7 bp encoding the amino terminus of the protein from the start codon ATG. This fragment does not contain the Prm promoter region.

A 28 bp synthetic DNA fragment was synthesized to repair the 7 bp deletion and to create BglII, ScaI and NdeI endonuclease recognition sites upstream from the ATG start codon of cI 857, and to create an Hgi AI site immediately following the ATG start codon.

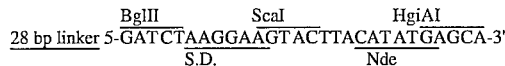

The Shine-Dalgarno sequence of λ cII gene was inserted between the BglII and ScaI sites, 11 bp upstream from the first ATG codon of cI protein. The 28 base pair synthetic DNA fragments was treated with polynucleotide kinase to phosphorylate the 5' end, then mixed with a 20 base pair complementary strand to generate a double strand DNA fragment. This fragment was also phosphorylated at the 5' end to facilitate ligation.

20 bp complementary synthetic DNA fragment

3'-ATTCCTTCATGAATGTATAC-5'

The fragment obtained by digestion of pJBF 5401 (see FIG. 1) with BglII, PvuII and AvaI contains the deo P1 site between the BamHI site and the BglII cleavage site at the 3' end of the fragment. This fragment was annealed to the synthetic fragment and then to the 932 bp PstI (Klenow)—Hgi AI fragment, and the mixture was ligated with $T_4$ ligase. The resulting plasmid, designated pMF-54DC, contains the deo P1 operator/promoter, and the cI 857 repressor and it directs expression of cI 857 repressor protein under the control of the deo P1 promoter.

Figure 24:
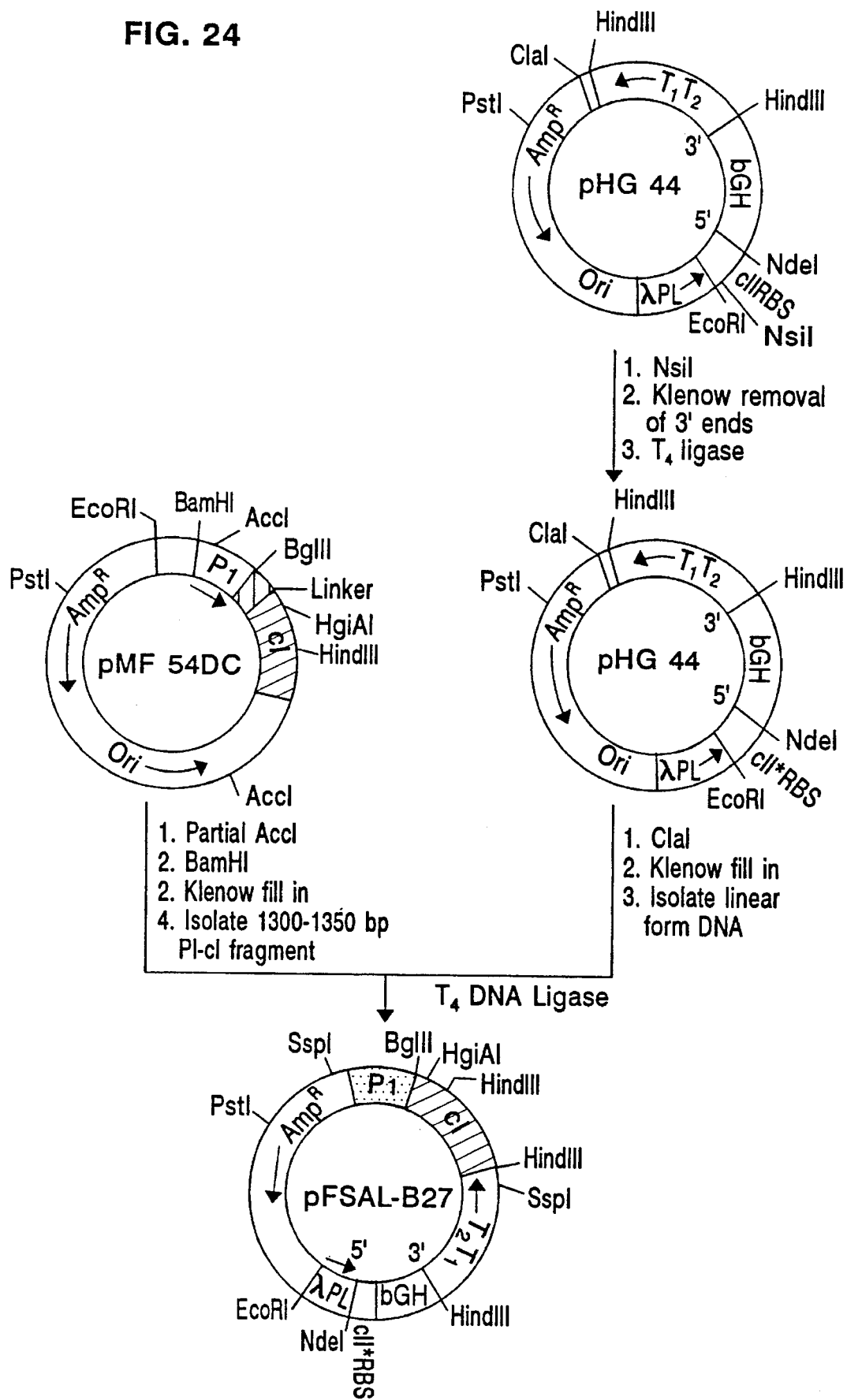

FIG. 24: Construction of pFSAL-B27

Plasmid pHG 44 (ATCC Accession No. 39806) has been described in copending, coassigned U.S. patent application Ser. No. 644,671 and EPO Publication No. 173,280. It is a plasmid derived from pBR322, harboring the λ $P_L$ promoter, the cII ribosomal binding site controlling the bGH gene, and $T_1T_2$ transcription termination sequences. The cII ribosomal binding site was modified by cleavage with NsiI and removal of 3' ends to produce plasmid pSAL 440-22. (The cII* RBS indicates modification of the cII RBS, which is now N-protein independent.) Plasmid pSAL 440-22 was cleaved with ClaI and the 5' ends filled in with *Escherichia coli* DNA polymerase (Klenow fragment). The full-length linear form of DNA produced was ligated to the fragment (1300–1350 bp long), containing deo P1 and cI 857, which had been isolated from plasmid pMF-54DC after partial AccI, and BamHI digestion followed by Klenow fill-in.

This produced plasmids pFSAL-B27 and pFSAL-A5. Plasmid pFSAL-B27 contains in clockwise orientation the deo P1 and the λ cI 857 repressor, whereas they are in counterclockwise orientation in pFSAL-A5. Sequence analysis subsequently demonstrated that the deo P1 promoter sequence present in plasmid pFSAL-B27 is truncated at the 5' end, whereas the complete deo P1 promoter sequence is present in pFSAL-A5. The truncated deo P1 promoter sequence no longer contains the EcoRI restriction site. Both plasmids contain in counterclockwise orientation the λ $P_L$, the modified cII ribosomal binding site (cII*), the bGH gene and the $T_1T_2$ terminator sequence. These plasmids express a bGH analog protein only when heat-induced (at 42°) which demonstrates that the deo P1 operator/promoter region is directing the expression of a functional thermolabile cI 857 repressor protein (see Example 9). Plasmid pFSAL-B27 has been deposited in the ATCC as pFSAL-130-B27 (ATCC Accession No. 67071 on Apr. 1, 1986). A diagram of pFSAL-A5 is shown in FIG. 25.

Figure 25:
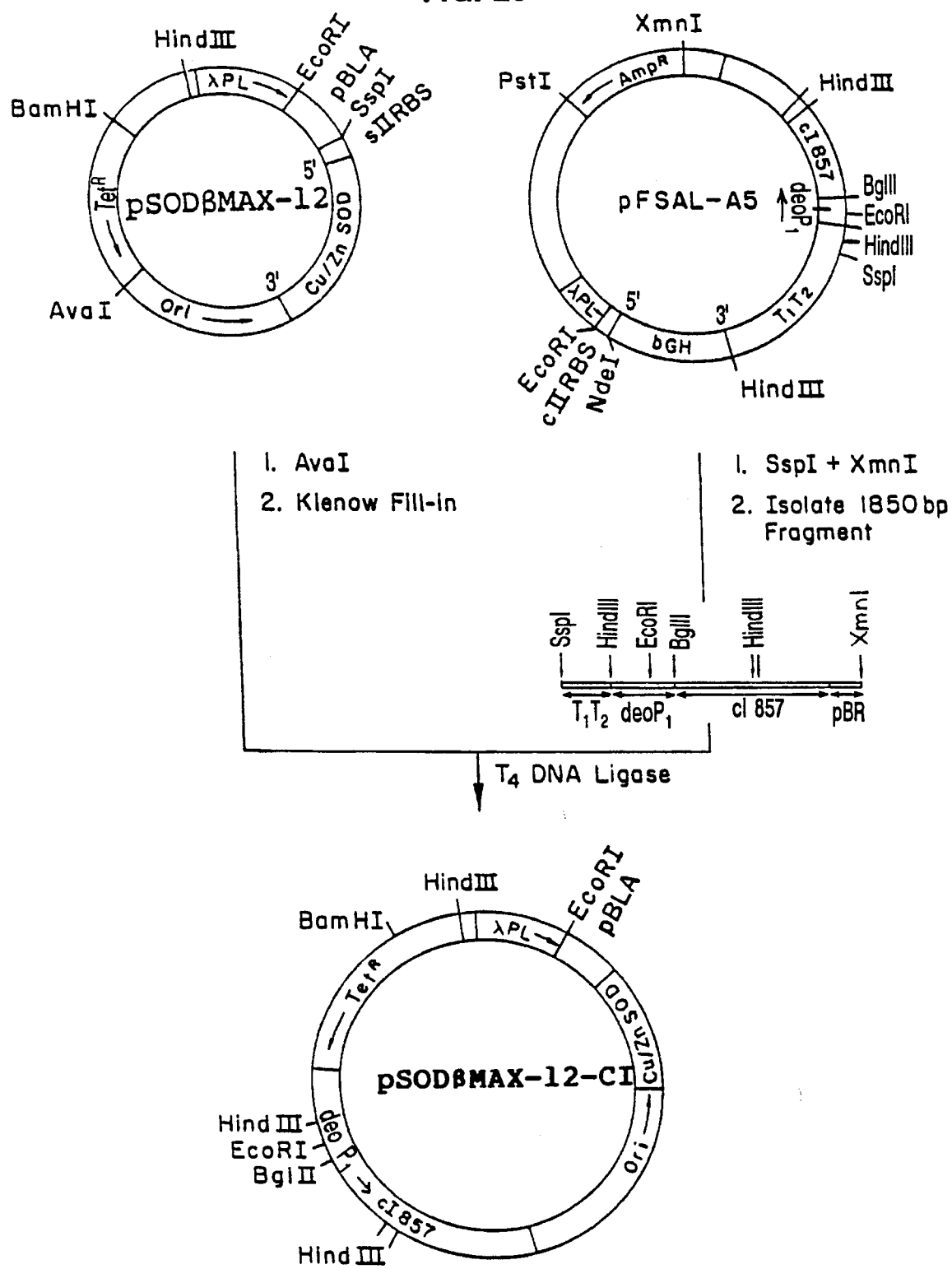

FIG. 25: construction of pSODβMAX-12-cI

Plasmid pFSAL-A5 was constructed as described in the legend to FIG. 24; it is similar to plasmid pFSAL-B27 except that the orientation of the deo P1 and the λ cI 857 repressor is counterclockwise. In addition, plasmid pFSAL-A5 contains the complete deo P1 promoter sequence whereas plasmid pFSAL-B27 contains the truncated deo P1 promoter sequence. Plasmid pFSAL-A5 was cleaved with SspI and XmnI and the small fragment containing deo P1 and λ cI 857 was ligated to the filled-in AvaI site of plasmid pSODβMAX-12 (see FIG. 16).

The resulting plasmid, designated pSODβMAX-12-cI contains deo P1 controlling the λ cI 857 repressor, and in a 5' to 3' direction, the λ $P_L$ promoter, the β-lactamase ribosomal binding site and the Cu—Zn SOD gene. This plasmid is independent of λ genes on the *Escherichia coli* chromosomes and hence can be transformed into a wide variety of hosts. Plasmid pSODβMAX-12-cI expresses hSOD analog at about half the level of the parent plasmid pSODβMAX12.

Figure 26:
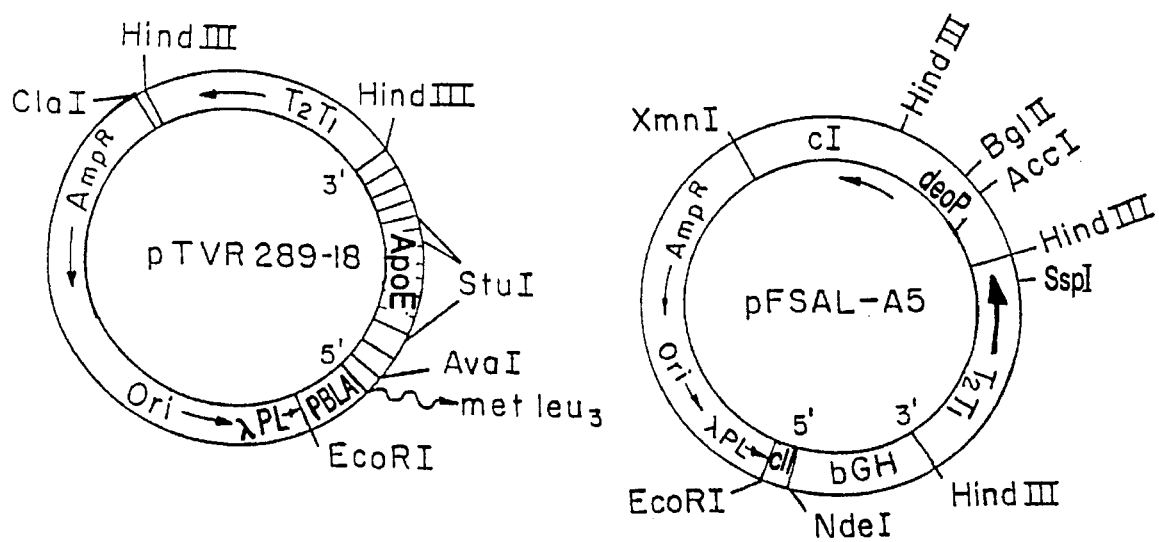
Figure 26:
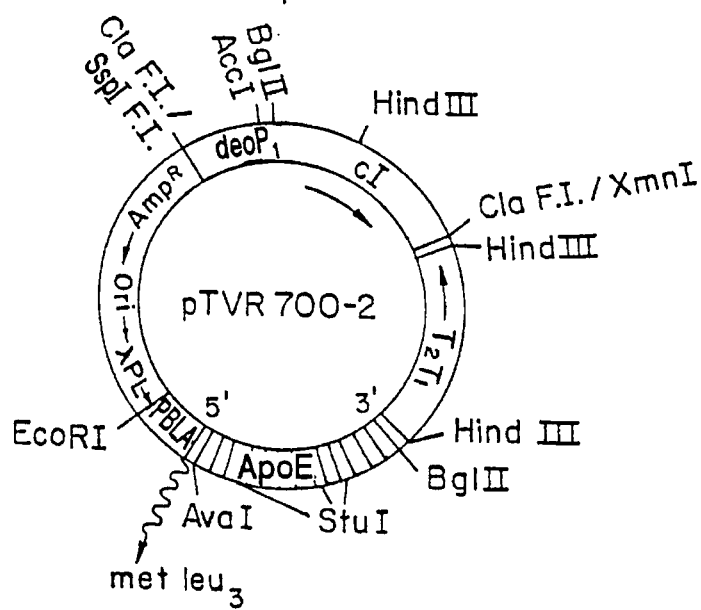

FIG. 26: Construction of pTVR 700-2

The small fragment containing the deo P1 and λ cI 857 repressor was obtained from plasmid pFSAL-A5 as described in FIG. 25. It was ligated to the filled-in ClaI site of plasmid pTVR 289-18 which expresses met-leu-leu-leu-met-ApoE (apolipoprotein E analog) under the control of the λ $P_L$ promoter (see FIG. 29).

The resulting plasmid, pTVR 700-2, contains in counterclockwise direction the λ promoter, the β-lactamase promoter—ribosomal binding site and the sequence for the ApoE analog, and in a clockwise direction the deo P1 operator/promoter and the cI 857 repressor. It expresses met-leu-leu-leu-met-ApoE only when heat-induced at 42° C., indicating that the deo P1 promoter is controlling the expression of functional thermolabile cI 857 repressor protein (see Example 11).

Note: Plasmid pTVR 700-2 was first introduced into *E. coli* MC 1061 where it was designated pTVR 596-1 and subsequently transfected into wild-type *Escherichia coli* 12435 where it was designated pTVR 700-2.

Figure 27:
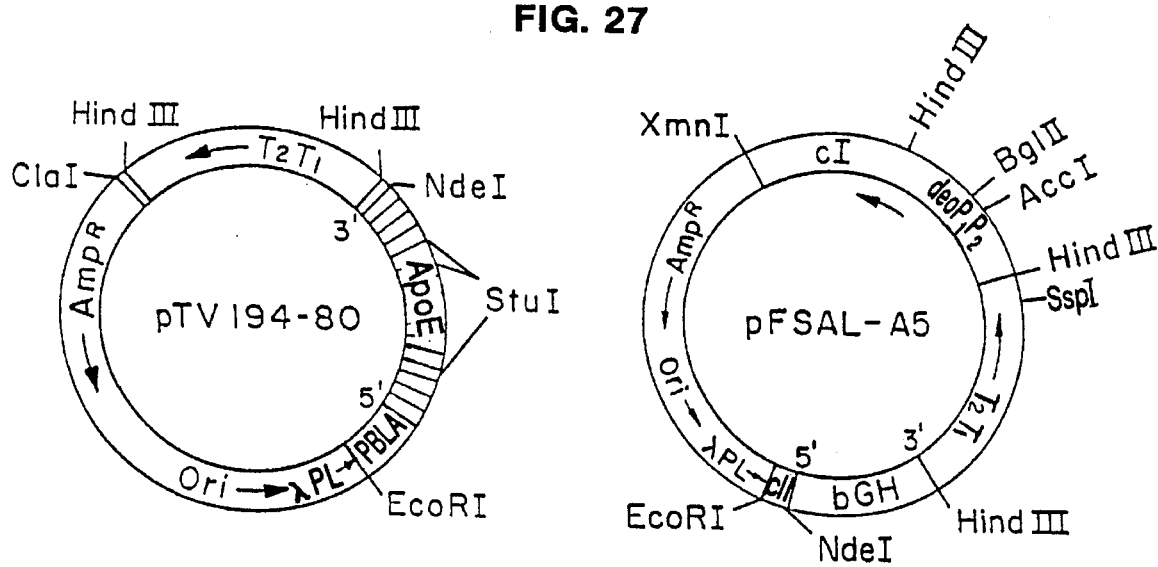
Figure 27:
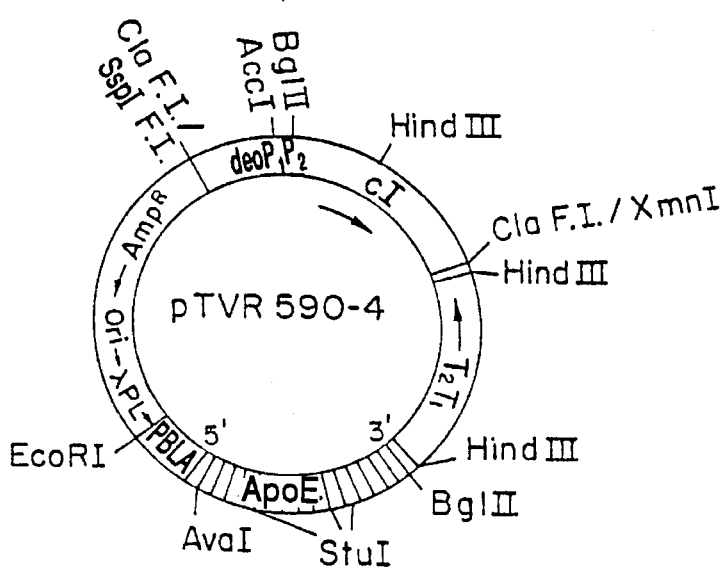

FIG. 27: Construction of pTVR 590-4

The small fragment containing deo P1 and λ cI 857 repressor was obtained from plasmid pFSAL-A5 as described in FIG. 25. It was ligated to the filled-in ClaI site of plasmid pTV 194-80 which expresses met-ApoE under the control of the λ $P_L$ promoter (plasmid pTV 194-80 was constructed as shown in FIGS. 31–33 and 35).

The resulting plasmid, pTVR 590-4, contains in a counterclockwise direction the λ $P_L$ promoter, the β-lactamase promoter-ribosomal binding site and the sequence for met-ApoE, and in a clockwise direction the deo P1 promoter and the cI 857 repressor. It expresses met-ApoE only when heat induced at 42° C., indicating that the deo P1 promoter is controlling the expression of functional repressor (see Example 11). Plasmid pTVR 590-4 has been deposited with the American Type Culture Collection in Rockville, Md. under ATCC Accession No. 67360.

Note: Plasmid pTVR 590-4 was first introduced into *Escherichia coli* MC 1061 where it was designated pTVR 583-17 and subsequently transfected into wild-type *Escherichia coli* 12435 where it was designated pTVR 590-4.

FIG. 28: Production of pE4GPX

Plasmid pMSE4 (ATCC Accession No. 53250) contains cDNA which encodes the complete coding sequence for MnSOD (human manganese superoxide dismutase) under the control of the λ $P_L$ promoter and the cII ribosomal binding site. It was cleaved with StuI which removed a 67 bp fragment at approximately 450 bp from the 5' end of the MnSOD sequence. The fragment containing the GPX sequence, obtained from plasmid p18UL-1 (ATCC Accession No. 67361) by NdeI digestion, Klenow fill-in and SspI digestion, was inserted between the two StuI sites within the MnSOD cDNA. Plasmid p18UL-1 has been deposited with the ATCC in Rockville, Md. under ATCC Accession No. 67361. The resulting plasmid, pE4GPX, expresses an MnSOD-GPX fused protein under the control of the λ $P_L$ and the cII ribosomal binding site.

Figure 29:
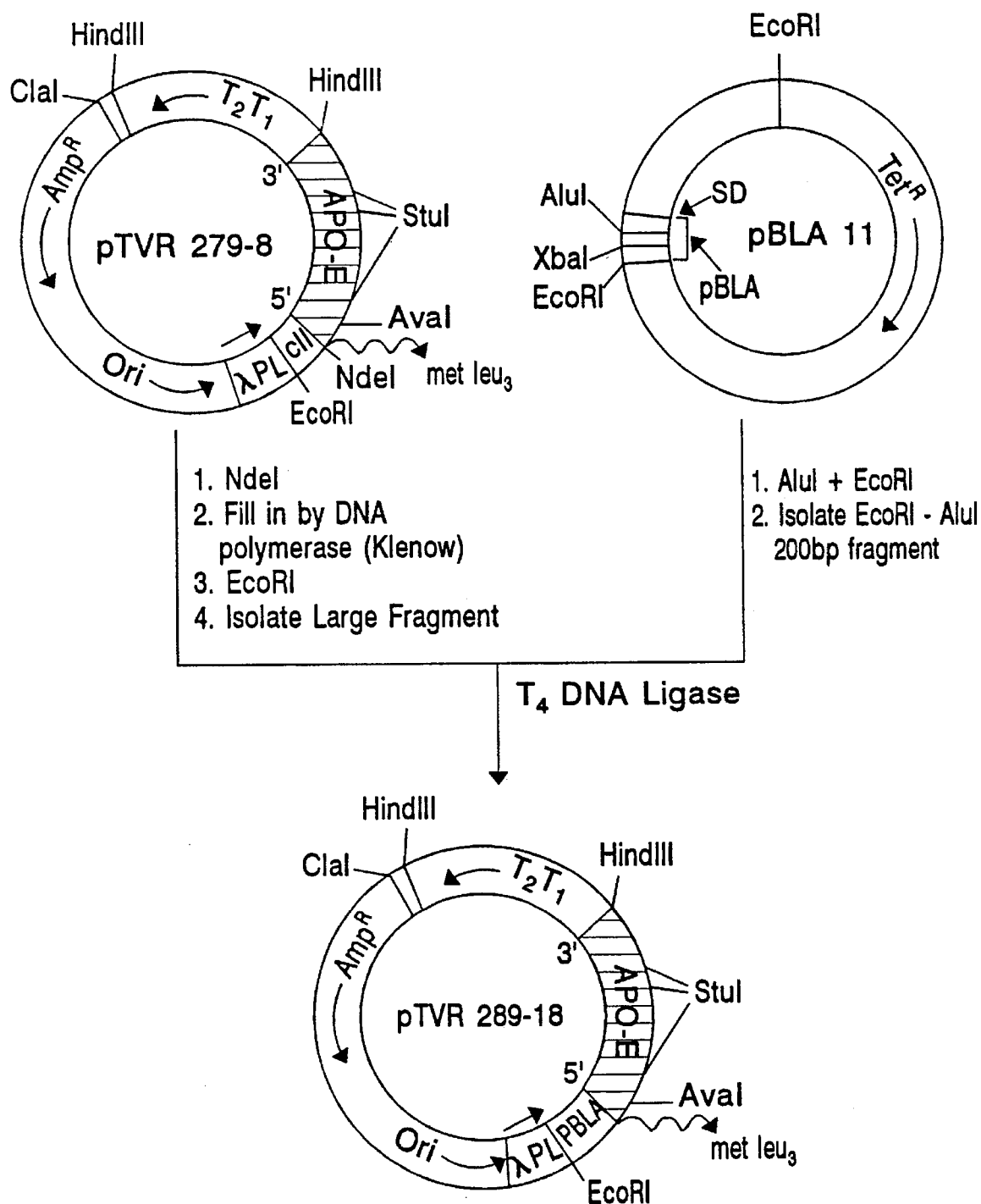

FIG. 29: Production of pTVR 289-18

The construction of plasmid pTVR 279-8 (ATCC Accession No. 53216 on Aug. 2, 1985) is fully described in coassigned copending U.S. Ser. No. 896,750 and also described in EPO Publication No. 173,280. This plasmid expresses a met-leu-leu-leu-met apolipoprotein E3 analog under the control of the λ $P_L$ promoter and the cII ribosomal binding site.

The cII ribosomal binding site was removed from pTVR 279-8 by NdeI digestion, Klenow fill-in and EcoRI digestion, and the large fragment produced was isolated. This fragment was ligated to the EcoRI-AluI 200 bp fragment from pBLA11 (ATCC Accession No. 39788 on Aug. 2, 1984) which contains the promoter and ribosomal binding site of β-lactamase (designated pBLA). The resulting plasmid contains in 5' to 3' order the λ $P_L$ promoter, the β-lactamase promoter-ribosomal binding site and the sequence for met-leu-leu-leu-met-ApoE, with deletion of the NdeI site at the 5' end of the ApoE sequence. This plasmid, designated pTVR 289-18, expresses met-leu-leu-leu-met-ApoE. (The construction of plasmid pTVR 289-18 is also described in copending, coassigned U.S. application Ser. No. 896,750, and is hereby incorporated by reference to more clearly illustrate how the plasmid is constructed.)

FIG. 30: Construction of pSODα13 and PSODβ1

The plasmid pSODα2 (ATCC Accession No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC Accession No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODα1 contains the ribosomal binding site of the β-lactamase gene and the λ $P_L$ promoter.

Figure 31:
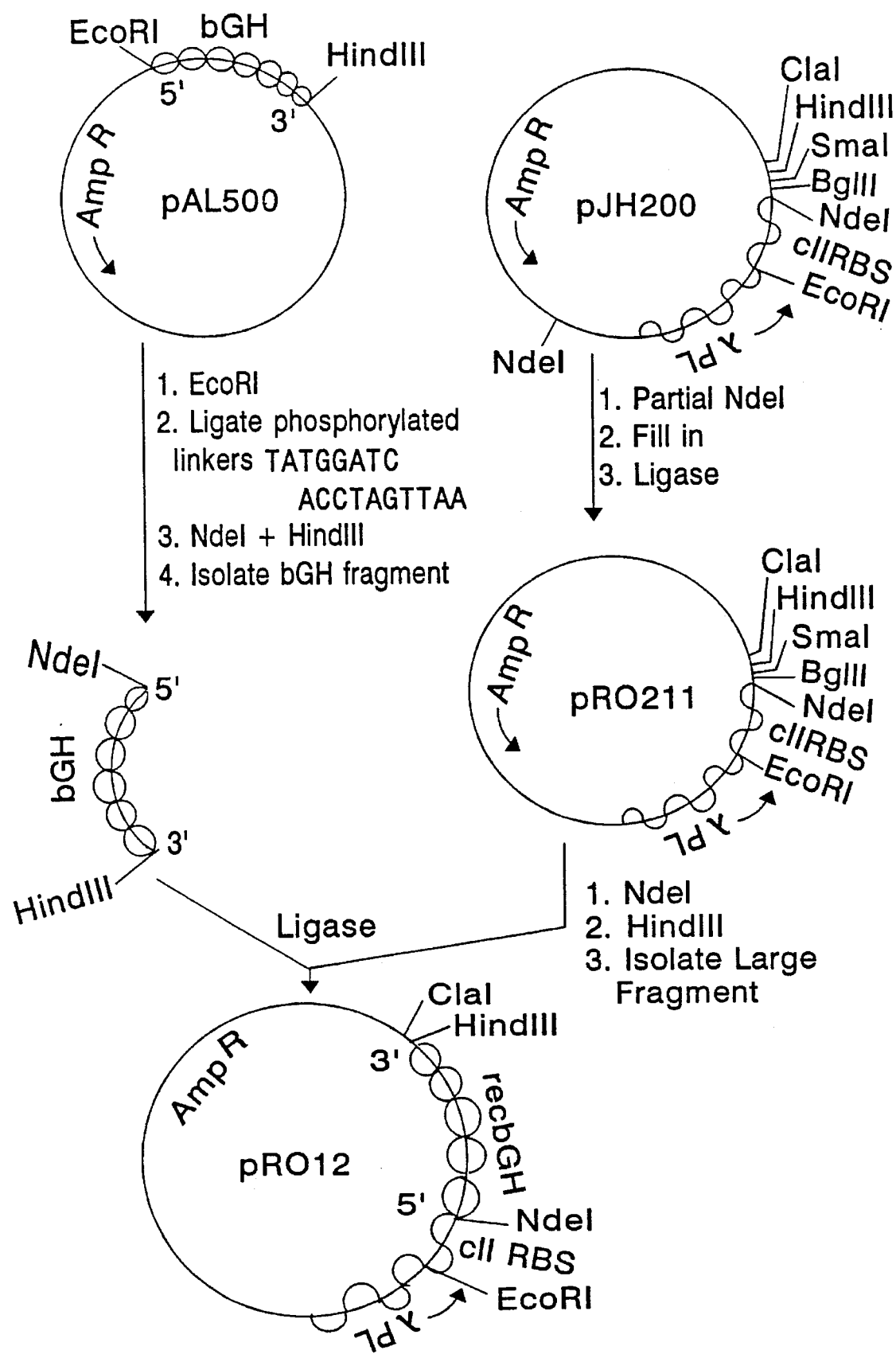

FIG. 31: Construction of pRO211 and pRO12

The plasmid pJH200 (ATCC Accession No. 39783) was partially digested with NdeI, treated with DNA polymerase I (Klenow) to fill in the ends and the resulting DNA was religated to form the expression vector pRO211. The expression vector pRO211 was digested with NdeI and HindIII, the large fragment isolated and ligated to an NdeI-HindIII bGH fragment isolated from pAL500 (ATCC Accession No. 39782) to produce pRO12. (The NdeI-HindIII fragment was produced from pAL500 by digesting it with EcoRI and ligating to the ends of the digestion product synthetic linkers with the sequence:

```
TATGGATC
ACCTAGTTAA
```

The ligation mixture was digested with NdeI and HindIII and the resulting NdeI-HindIII bGH fragment isolated.

Figure 32:
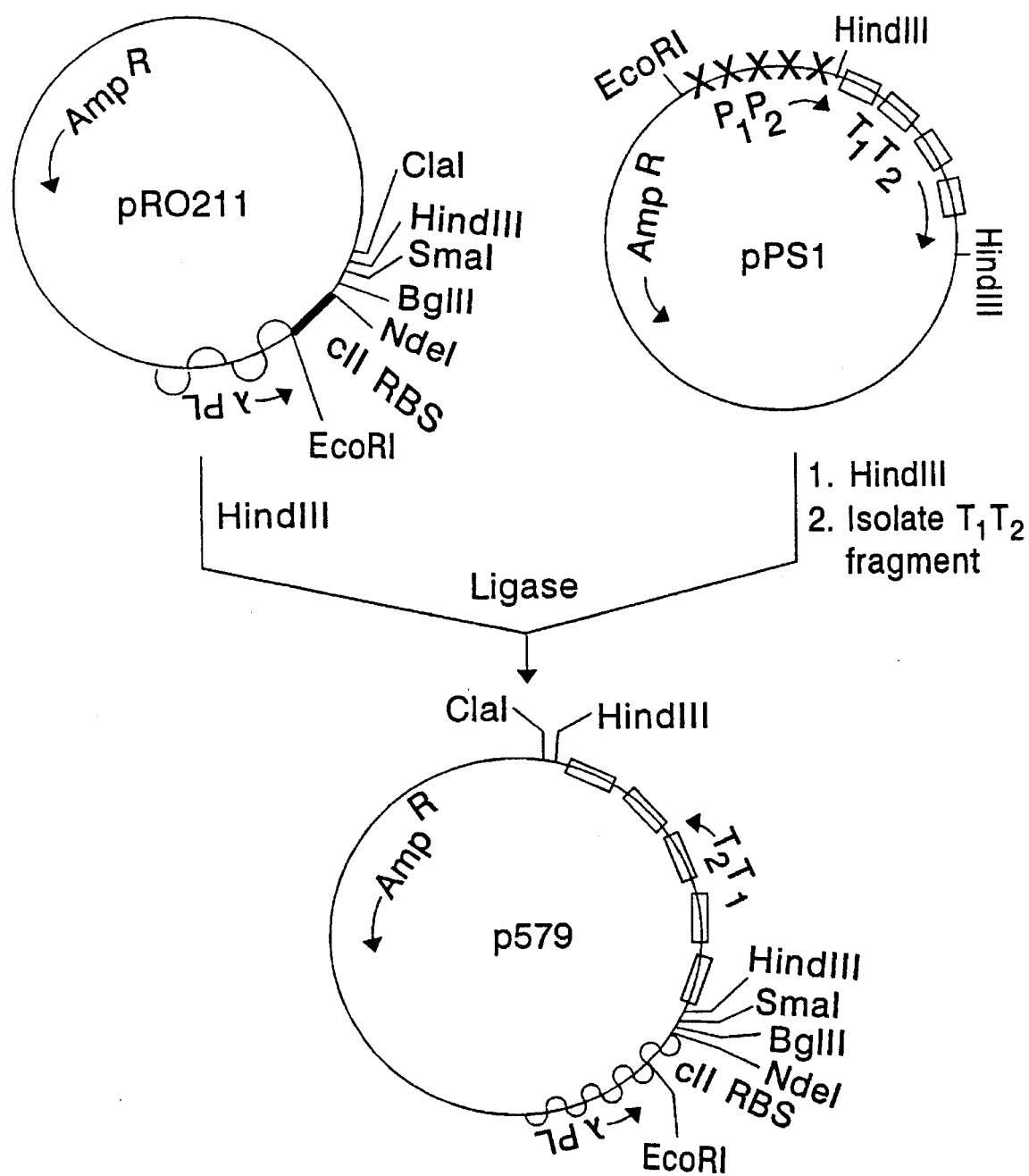

FIG. 32: Construction of p579

The rRNA operon $T_1T_2$ transcription termination fragment was isolated from plasmid pPS1 (ATCC Accession No. 39807) which had been digested with HindIII. The $T_1T_2$ fragment was inserted into the unique HindIII site of pRO211 (FIG. 31) which had been digested with HindIII. The resulting expression vector, p579, contains the λ $P_L$ promoter, the $C_{II}$ ribosomal binding site, followed by the $T_1T_2$ transcription termination signals.

Figure 33:
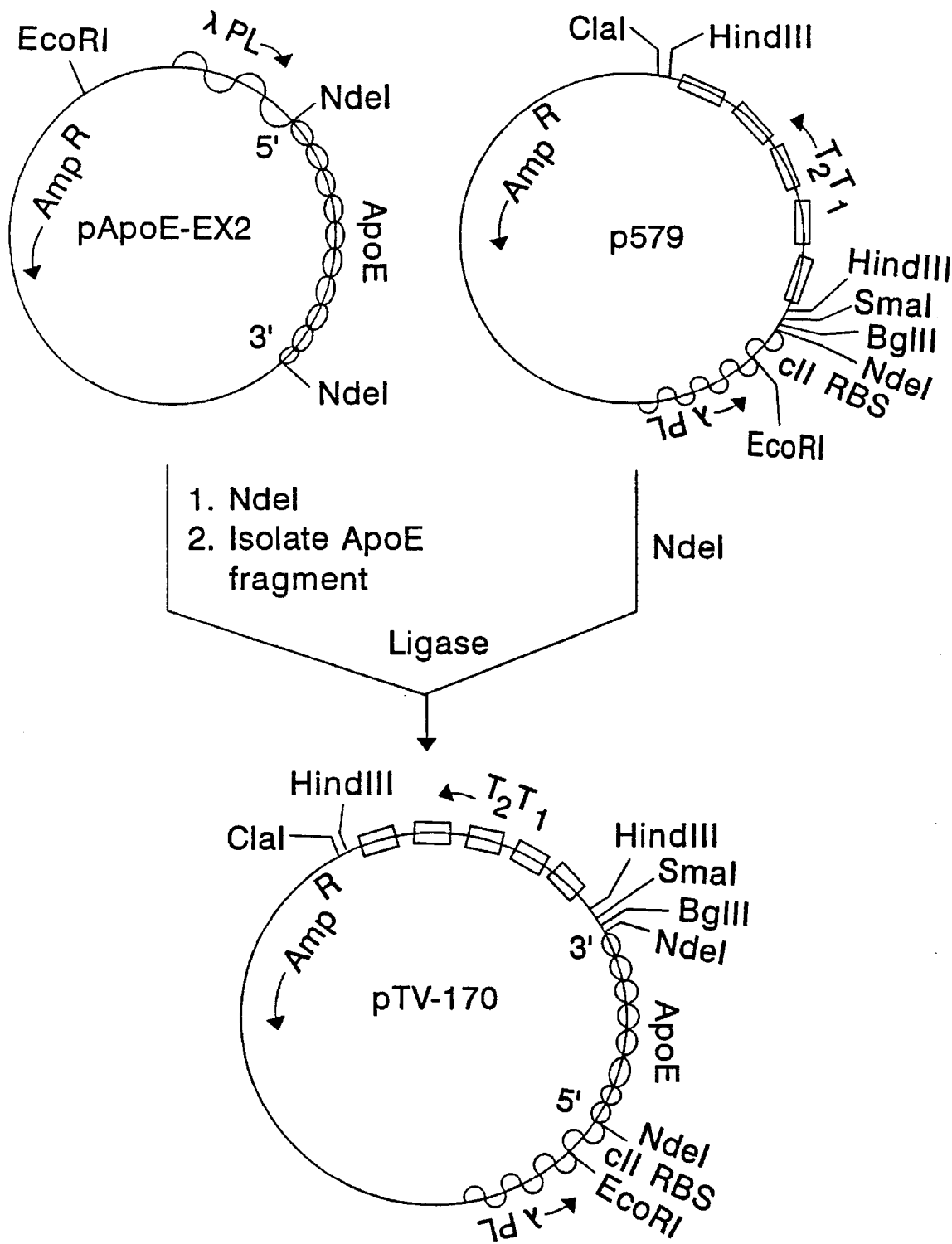

FIG. 33: Construction of pTV-170

The NdeI-NdeI ApoE fragment was isolated from plasmid pApoE-EX2 (ATCC Accession No. 39787) and inserted into the unique NdeI site of the expression vector p579 (FIG. 32) which had been digested with NdeI. The resulting plasmid pTV-170 expresses an analog of natural human ApoE protein having a methionine residue added at the N-terminus.

Figure 34:
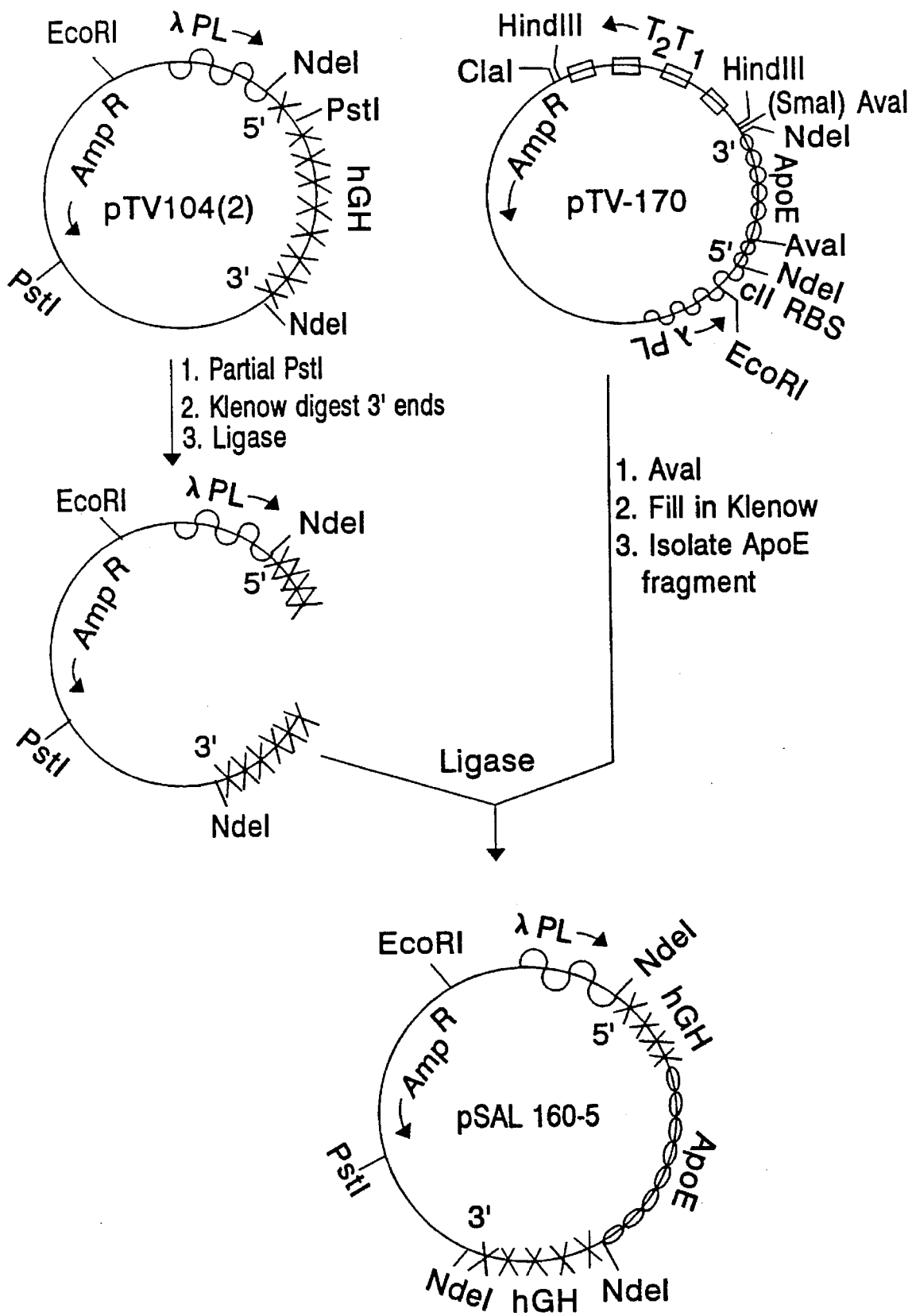

FIG. 34: Construction of pSAL 160-5

An AvaI-AvaI fragment containing the ApoE DNA sequence was isolated from pTV-170 (FIG. 33) which was digested with AvaI. The fragment was filled in with DNA polymerase I (Klenow) and isolated on agarose gel. The purified ApoE fragment was inserted into the PstI site of the pTV 104(2) plasmid (ATCC Accession No. 39384) which was partially digested with PstI followed by digestion of 3' ends with DNA polymerase I (Klenow). The resulting plasmid was designated pSAL 160-5.

Figure 35:
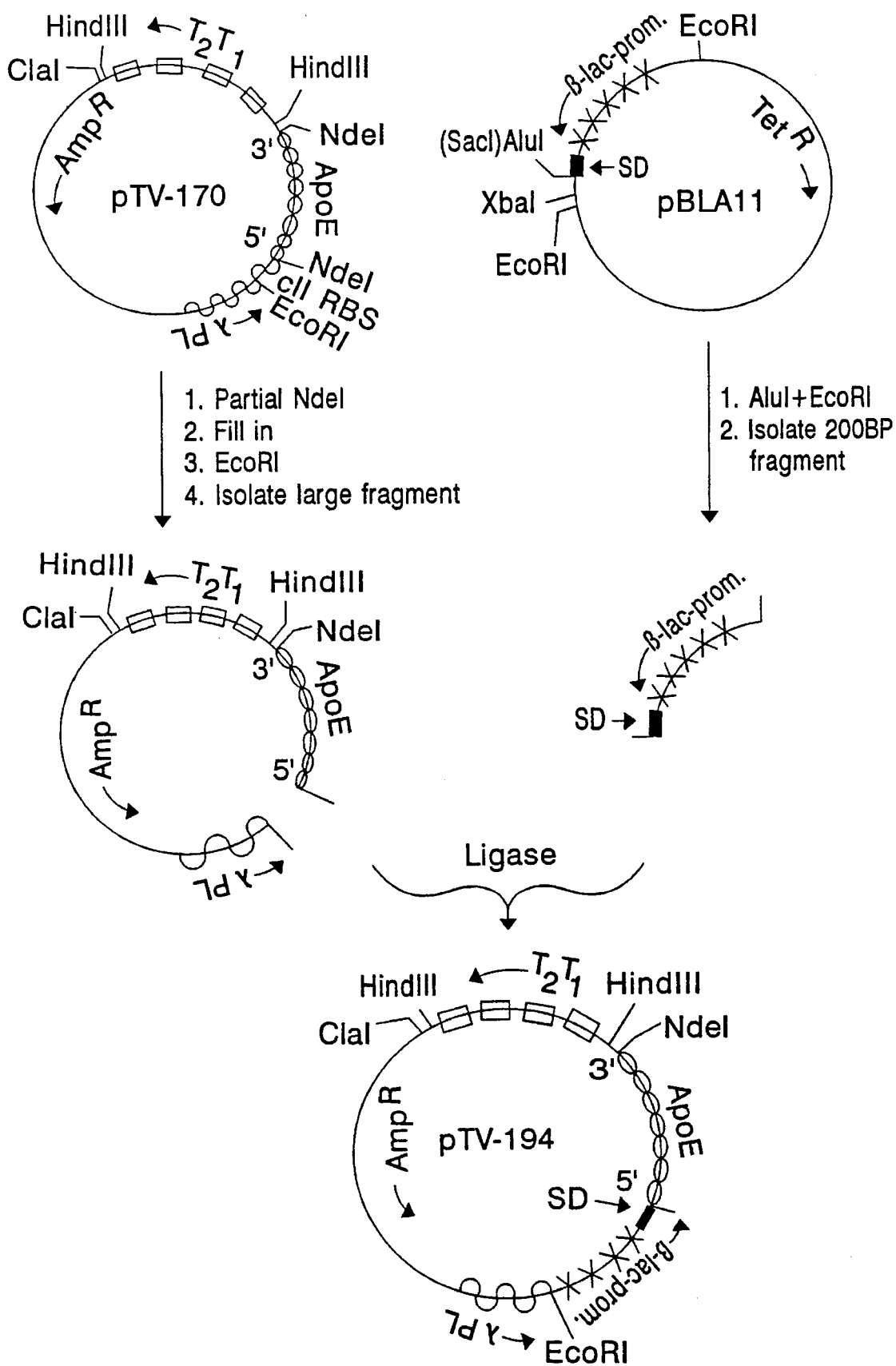

FIG. 35: Construction of pTV-194

The β-lactamase promoter and ribosomal binding site fragment was isolated from plasmid pBLA11 (ATCC Accession No. 39788) after digestion with EcoRI and AluI. This fragment was ligated to the large fragment of pTV-170 (FIG. 33) plasmid which had been partially digested with NdeI, filled in with DNA polymerase I (Klenow) and then digested with EcoRI.

Figure 36:
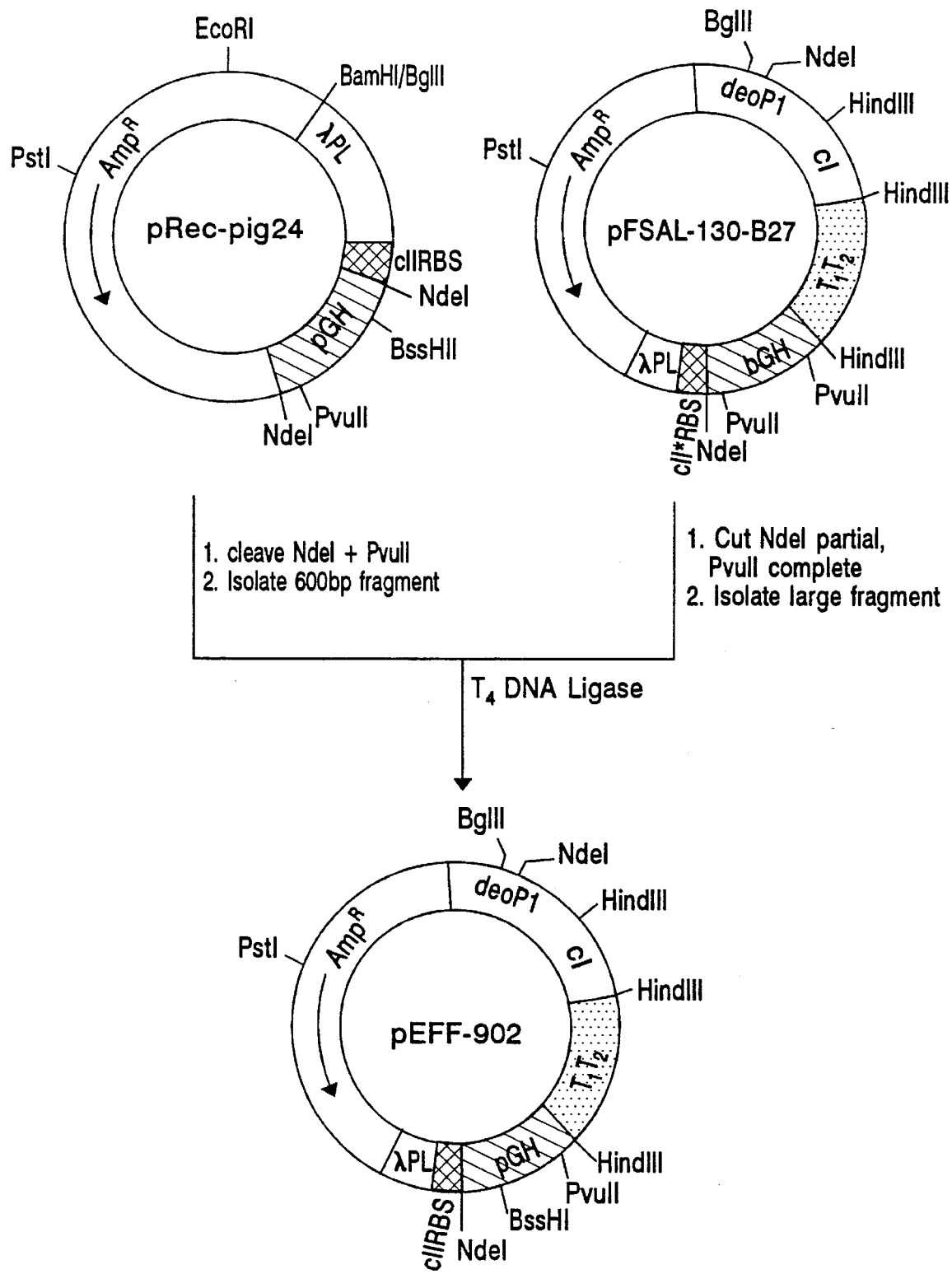

FIG. 36: Construction of pEFF-902—an "independent" plasmid expressing pGH analog Plasmid pRec-pig24 (ATCC Accession No. 53433) has been described in copending, coassigned U.S. patent application Ser. No. 821,830. It expresses a met-asp-gln-porcine growth hormone analog (pGH) under the control of the λ $P_L$ repressor and the cII ribosomal binding site. The 600 bp fragment encoding the pGH analog was cleaved from pRec-pig24 by NdeI and PvuII digestion and was inserted into plasmid pFSAL-130-B27 (ATCC Accession No. 67071; FIG. 24) from which the bGH encoding sequence had been removed by partial NdeI and complete PvuII digestion. The resulting plasmid, designated pEFF-902, contains the truncated deo P1 promoter controlling the λ cI 857 repressor and additionally in 5' to 3' order: the λ $P_L$ promoter, the cII ribosomal binding site, the pGH analog DNA sequence and the $T_1T_2$ transcription termination coding sequences. This plasmid, which is a high expressor of the pGH analog protein is independent of λ genes on the *Escherichia coli* chromosome and hence can be transformed into a wide variety of hosts.

Figure 37:
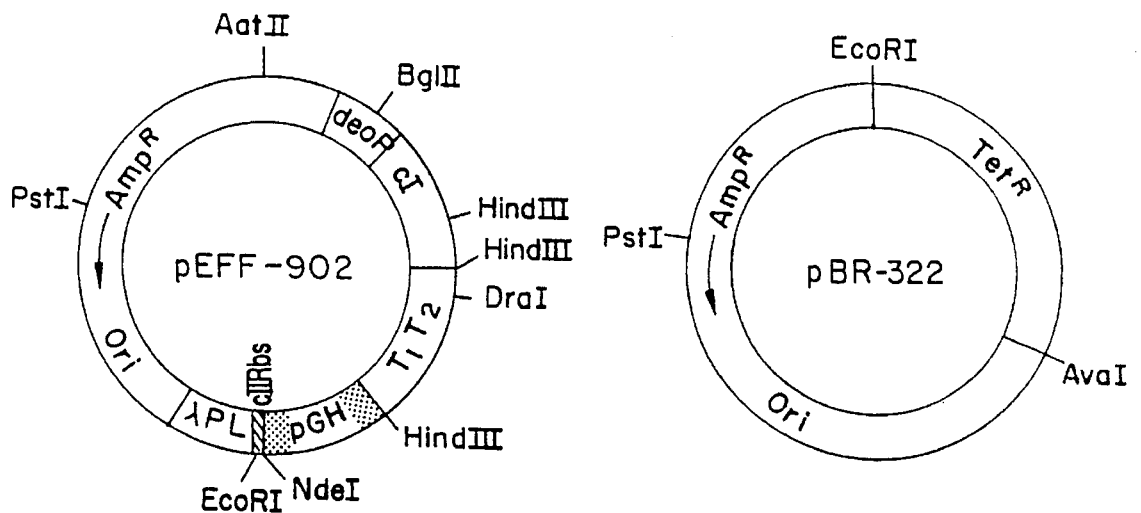
Figure 37:
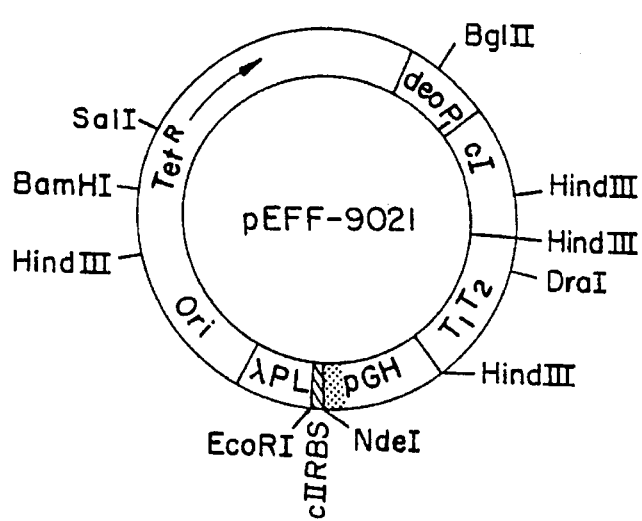

FIG. 37: Construction of pEFF-9021—a further "independent" plasmid expressing pGH analog (tetracycline—resistant)

A blunt-ended fragment containing the tetracycline resistance gene from plasmid pBR322 (ATCC Accession No. 37017), produced by cleavage with EcoRI and AvaI and fill-in with Klenow enzyme was inserted into the large fragment of plasmid pEFF-902 from which the ampicillin gene had been removed by AatII and PstI digestion followed by digestion of 3' ends with Klenow. This produced plasmid pEFF-9021 which is similar to plasmid pEFF-902 except that the ampicillin resistance gene has been replaced with the tetracycline resistance gene. Plasmid pEFF-9021 contains the truncated deo P1 promoter controlling the λ cI 857 repressor; it also contains in 5' to 3' order the λ $P_L$ promoter, the cII ribosomal binding site and the pGH analog DNA sequence and the $T_1T_2$ transcription termination coding sequences. It is an independent plasmid which is a high expressor of the pGH analog. A different isolate from the same ligation was found to be identical except that the tetracycline resistance gene is in the opposite orientation; this plasmid, designated pEFF-9022, is also a high expressor of the pGH analog.

Figure 38:
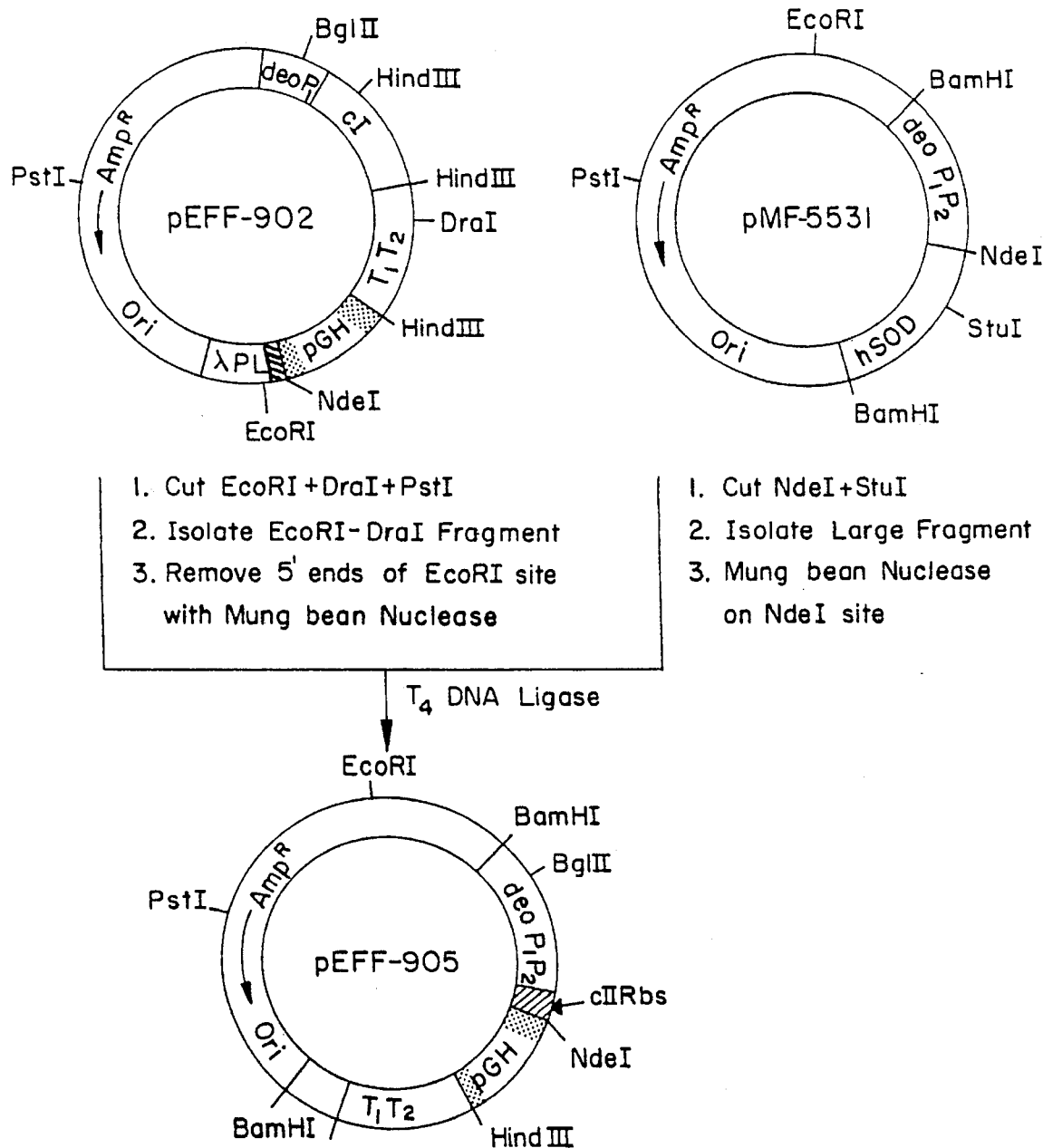

FIG. 38: Construction of pEFF-905—a deo $P_1P_2$ plasmid expressing pGH analog

The fragment containing in 5' to 3' order the cII ribosomal binding site, the pGH analog DNA sequence and the $T_1T_2$ transcription termination sequences was obtained from plasmid pEFF-902 by digestion with EcoRI, DraI and PstI, followed by isolation of the EcoRI-DraI fragment and then removal of the EcoRI 5' ends with Mung bean nuclease. This fragment was ligated to the large fragment obtained from plasmid pMF 5531 (FIG. 4) from which part of the hSOD coding sequence had been removed by NdeI and StuI digestion, followed by Mung bean digestion on the large fragment produced to remove the NdeI 5' ends. The resulting plasmid, designated pEFF-905, contains in 5' to 3' order, the deo P1-P2 promoter sequence, the cII ribosomal binding site, the pGH analog DNA sequence and the $T_1T_2$ transcription termination sequences. This plasmid is a very good expressor of the pGH analog protein but the construct proved to be unstable.

Figure 39:
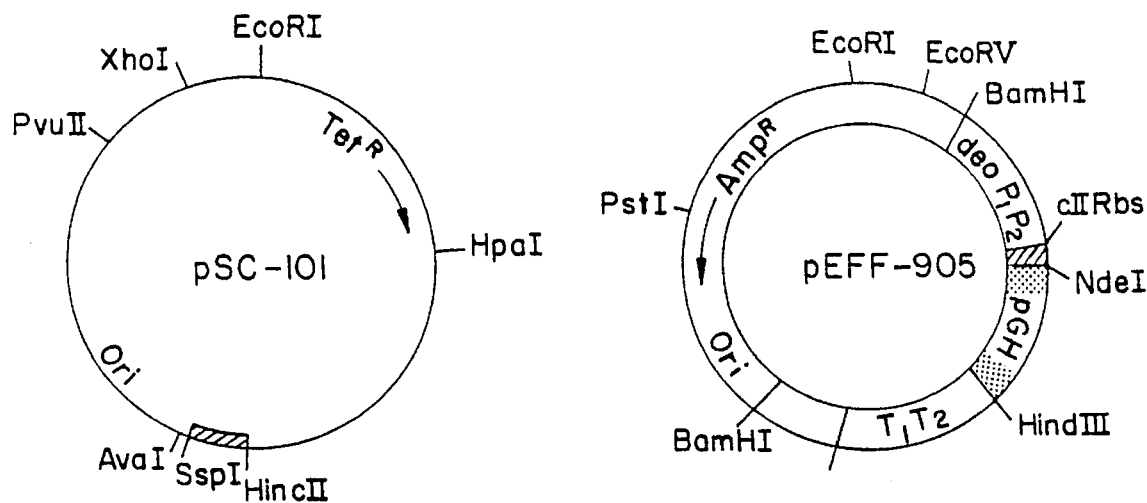
Figure 39:
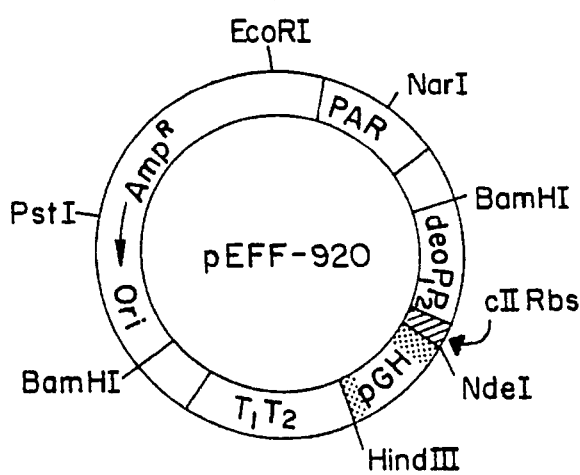

FIG. 39: Construction of pEFF-920—a deo P1-P2 plasmid (PAR⁺) expressing pGH analog A fragment containing the PAR (partition) sequence was isolated from plasmid pSC101 (ATCC Accession No. 37032) by cleaving the plasmid with SspI, PvuII and EcoRI, isolating the large fragment produced and cutting it with HincII. A 350 bp SspI-HincII fragment was isolated and was inserted into the EcoRV site in plasmid pEFF-905; the resulting plasmid was designated pEFF-920. This plasmid harbors the PAR sequence and in 5' to 3' order the deo P1-P2 promoter, the cII ribosomal binding site, the pGH analog DNA sequence and the $T_1T_2$ transcription termination sequences. Plasmid pEFF-920 is a very good expressor of the pGH analog protein and it has been deposited in *Escherichia coli* strain Sφ930 in the ATCC under Accession No. 67706.

Figure 40:
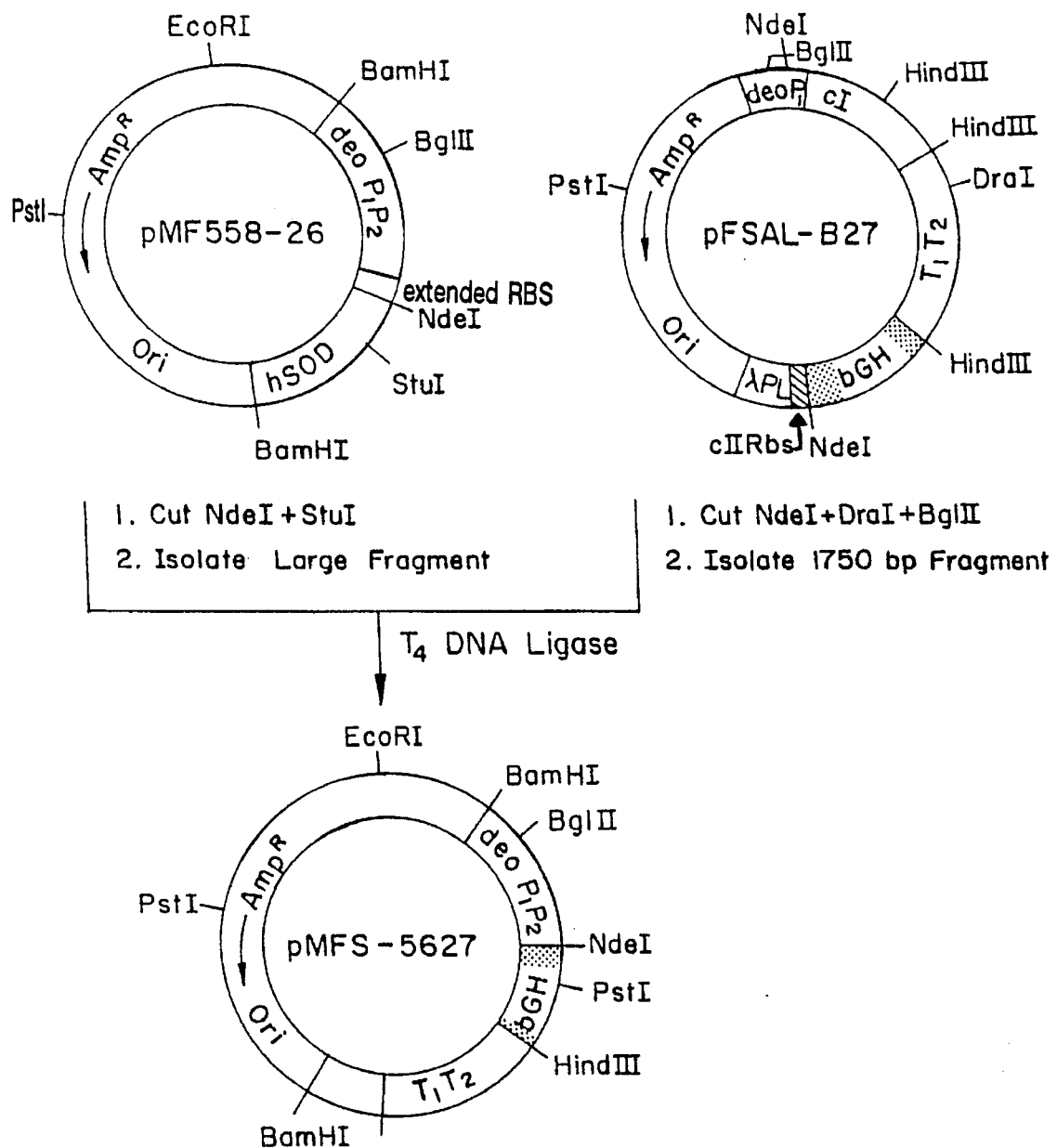

FIG. 40: Construction of pMFS-5627—a deo P1-P2 plasmid expressing bGH analog

The fragment containing in 5' to 3' order the bovine growth hormone (bGH) analog DNA sequence and the $T_1T_2$ transcription termination coding sequences was isolated from pFSAL-130-B27 (ATCC Accession No. 67071; see FIG. 24) by digestion with NdeI, DraI and BglII. This fragment was ligated to the large fragment obtained from pMF 558-26 (FIG. 6) after NdeI and StuI digestion. The resulting plasmid, designated pMFS-5627 contains in 5' to 3' order the deo P1-P2 promoter, the deo ribosomal binding site, the bGH analog DNA sequence and the $T_1T_2$ transcription termination coding sequences. This plasmid is a poor expressor of the bGH analog protein.

Figure 41:
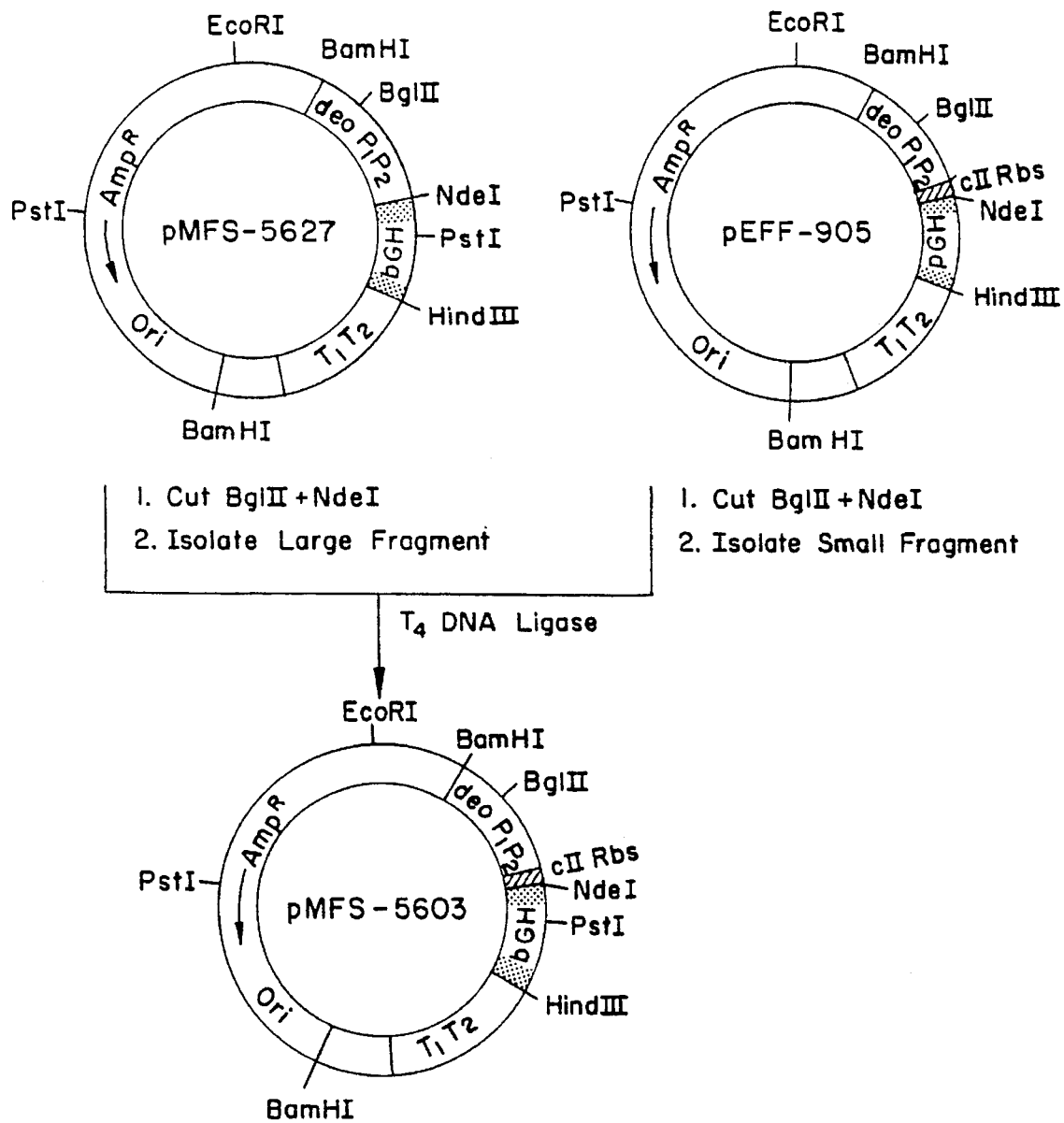

FIG. 41: Construction of pMFS-5603—another deo P1-P2 plasmid expressing bGH analog The small fragment containing part of the deo P1-P2 promoters and the cII ribosomal binding site, isolated from plasmid pEFF-905 by digestion with BglII and NdeI, was ligated to the large fragment obtained from pMFS-5627 cleaved with BglII and NdeI. The resulting plasmid, designated pMFS-5603 contains in 5' to 3' order the deo P1-P2 promoter, the cII ribosomal binding site, the bGH analog DNA sequence and the $T_1T_2$ transcription termination coding sequences. It is an intermediate expressor of the bGH analog protein.

Figure 42:
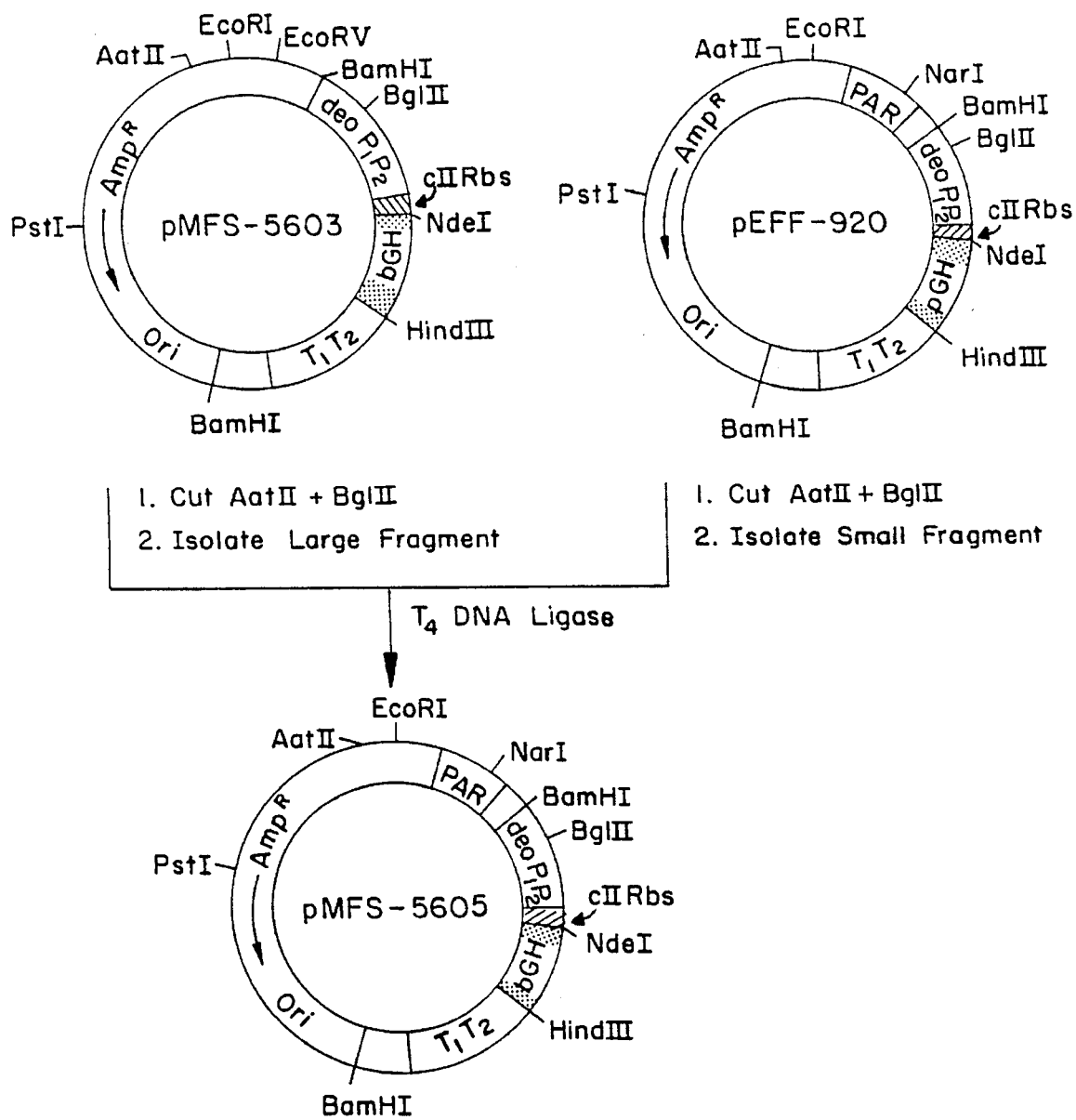

FIG. 42: Construction of pMFS-5605—a deo P1-P2 plasmid (pAR$^+$) expressing bGH analog The small fragment containing the PAR (partition) sequence from plasmid pEFF-920 (FIG. 39) was isolated from plasmid pEFF-920 after digestion with AatII and BglII. This fragment was ligated to the large fragment of plasmid pMFS-5603 which had been cleaved with AatII and BglII. The resulting plasmid, designated pMFS-5605, contains the PAR sequence and, in 5' to 3' order the deo P1-P2 promoter, the cII ribosomal binding site, the bGH analog DNA sequence and the $T_1T_2$ transcription termination coding sequences. It is a very good expressor of the bGH analog protein.

Plasmid pMFS-5607 (Tet$^R$) was constructed from plasmid pMFS-5605 (Amp$^R$) using the method shown in FIG. 7. Plasmid pMFS-5607 has been deposited in *Escherichia coli* strain Sφ930 (F$^-$) in the ATCC under Accession No. 67704. (*Escherichia coli* F$^-$ strains are further described in Example 21.)

Figure 43:
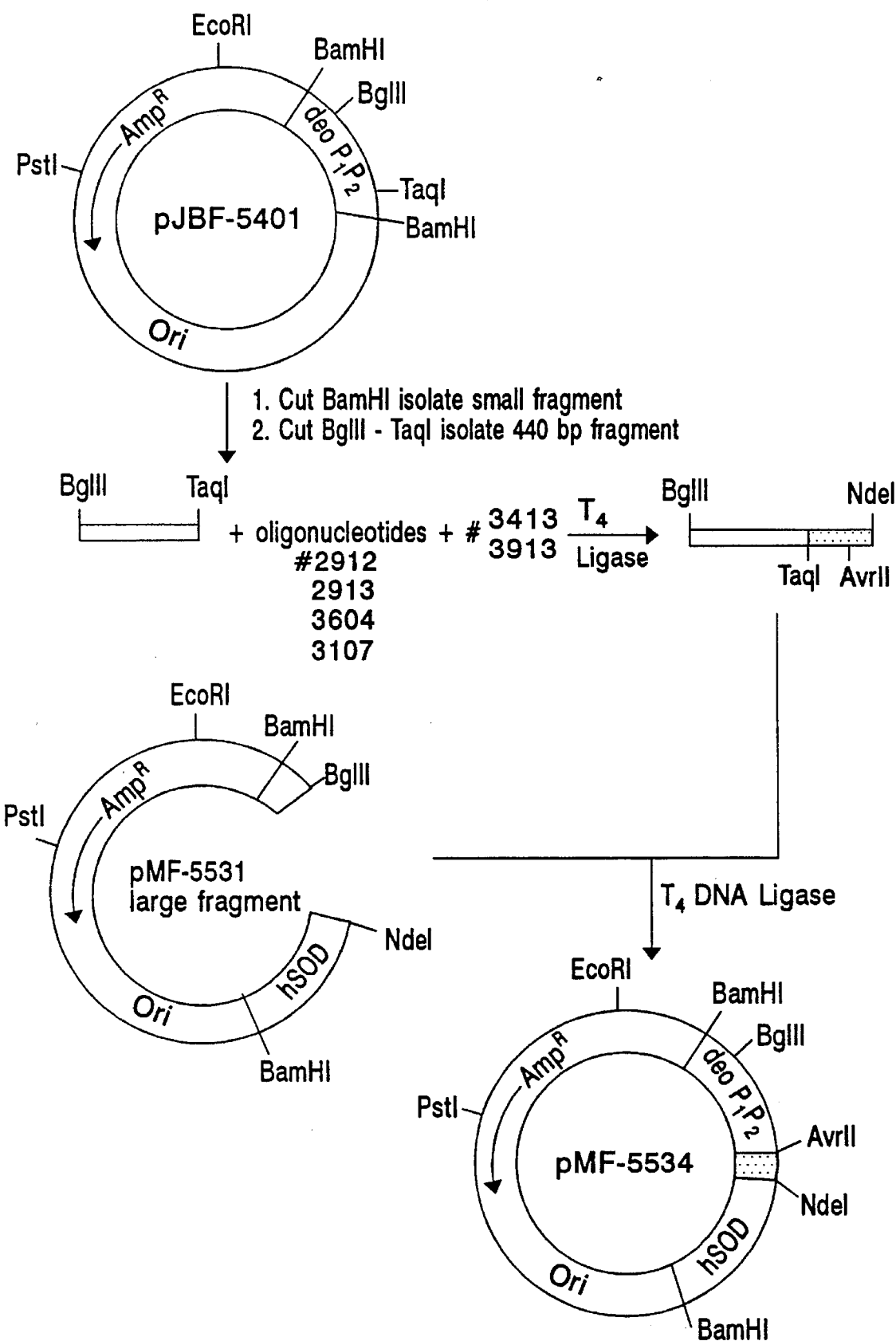

FIG. 43: Construction of plasmid pMF-5534—a plasmid containing a translational enhancer and expressing hSOD analog Plasmid pJBF5401 (FIG. 1) was cleaved with BamHI and the small (900 bp) fragment isolated and purified from low melt agarose. The BamHI fragment was then cleaved with restriction enzymes BglII and TaqI and the 440 bp fragment generated was isolated and purified. Synthetic linkers numbers 2912, 3604, 3107, 2913 (detailed in Description of FIG. 4) that are identical to a portion of the published deo nucleotide sequence covering the deo P2 promoter operator (Valentine-Hansen et al., EMBO 1: 317 (1982)) were annealed, ligated to each other and then ligated to the BglII-TaqI 440 bp fragment.

Short oligonucleotide sequences of 34 and 39 bases in length were chemically synthesized. These sequences are as shown.

```
                      AT  rich
5'    AAGCCTAGGTTTGTTTAACTTTAAGGAGAAATCA       #3413
3' CTGTTCGGATCCAAACAAATTGAAATTCCTCTTTAGTAT     #3913
```

After annealing of oligonucleotides numbers 3413 and 3913, the duplex was ligated to the extended BglII-TaqI fragment. This final ligation yielded a fragment, flanked by BglII-NdeI restriction sites, which includes an AT rich region (the translational "enhancer"—see Example 18). This fragment was ligated to the large fragment of pMF-5531 which had been produced by cleaving with BglII-NdeI. The resulting plasmid, designated pMF-5534, is a high level expressor of hSOD analog protein. It contains in 5' to 3' order the deo P1-P2 promoters, the modified deo ribosomal binding site with the enhancer sequence and the hSOD analog coding sequence.

Plasmid pMF-5534 was deposited in *Escherichia coli* strain Sφ930(F$^-$) in the ATCC Under Accession No. 67703.

Figure 44:
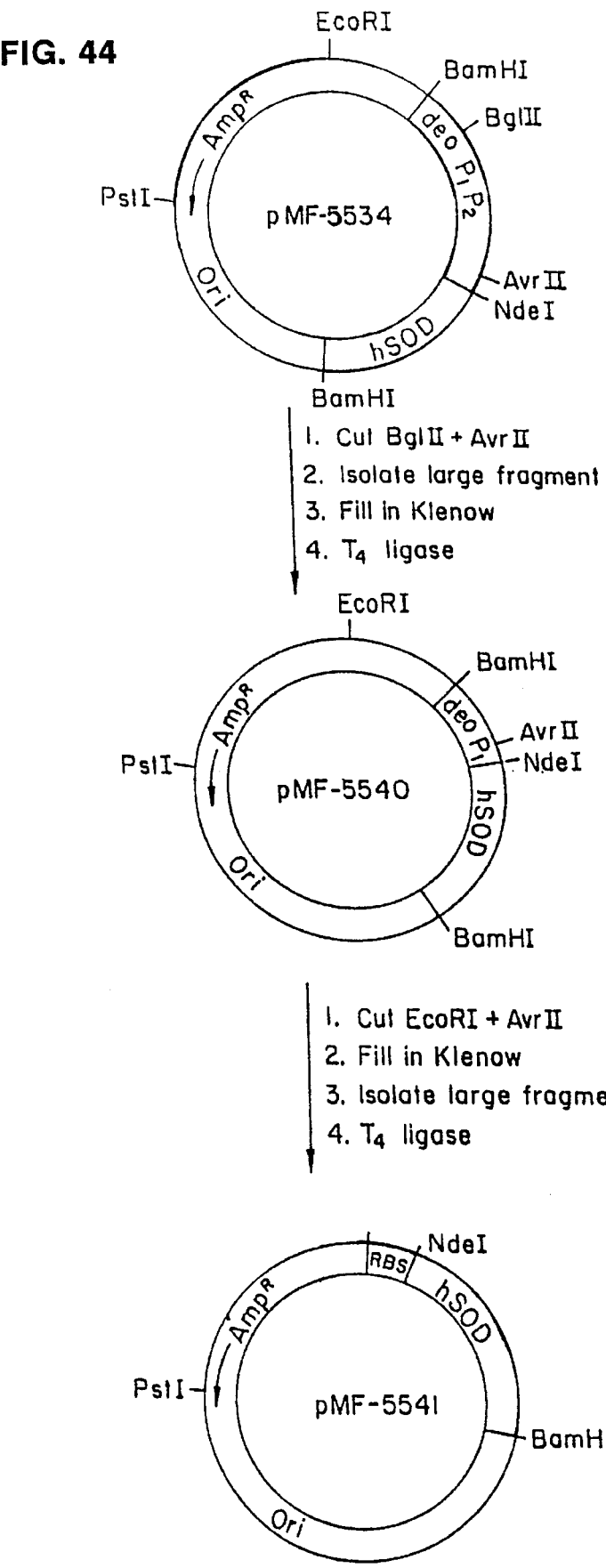

FIG. 44: Construction of plasmid pMF-5541

Plasmid pMF-5534 (FIG. 43) was cleaved with BglII and AvrII. The largest fragment observed on agarose gel was isolated and purified, and the cohesive ends were filled in with Klenow enzyme and ligated, thus recreating the AvrII site. This produced plasmid pMF-5540 which contains in 5' to 3' sequence the deo P1 promoter, the modified deo ribosomal binding site (RBS) with the enhancer sequence and the hSOD analog coding sequence. Plasmid pMF-5540 produces a high level of hSOD analog protein under the control of the deo P1 promoter and the translational enhancer.

Plasmid pMF-5540 was cleaved with EcoRI and AvrII; the cohesive ends were then filled in with Klenow enzyme and the large fragment was isolated and ligated with T4 ligase. These procedures removed the deo P1 and P2 promoter sequences except for the deo ribosomal binding site (RBS), and resulted in the formation of plasmid pMF-5541 which contains in 5' to 3' order the modified deo RBS with the enhancer sequence and the hSOD analog coding sequence. This plasmid produces an extremely low level of hSOD analog protein.

Figure 45:
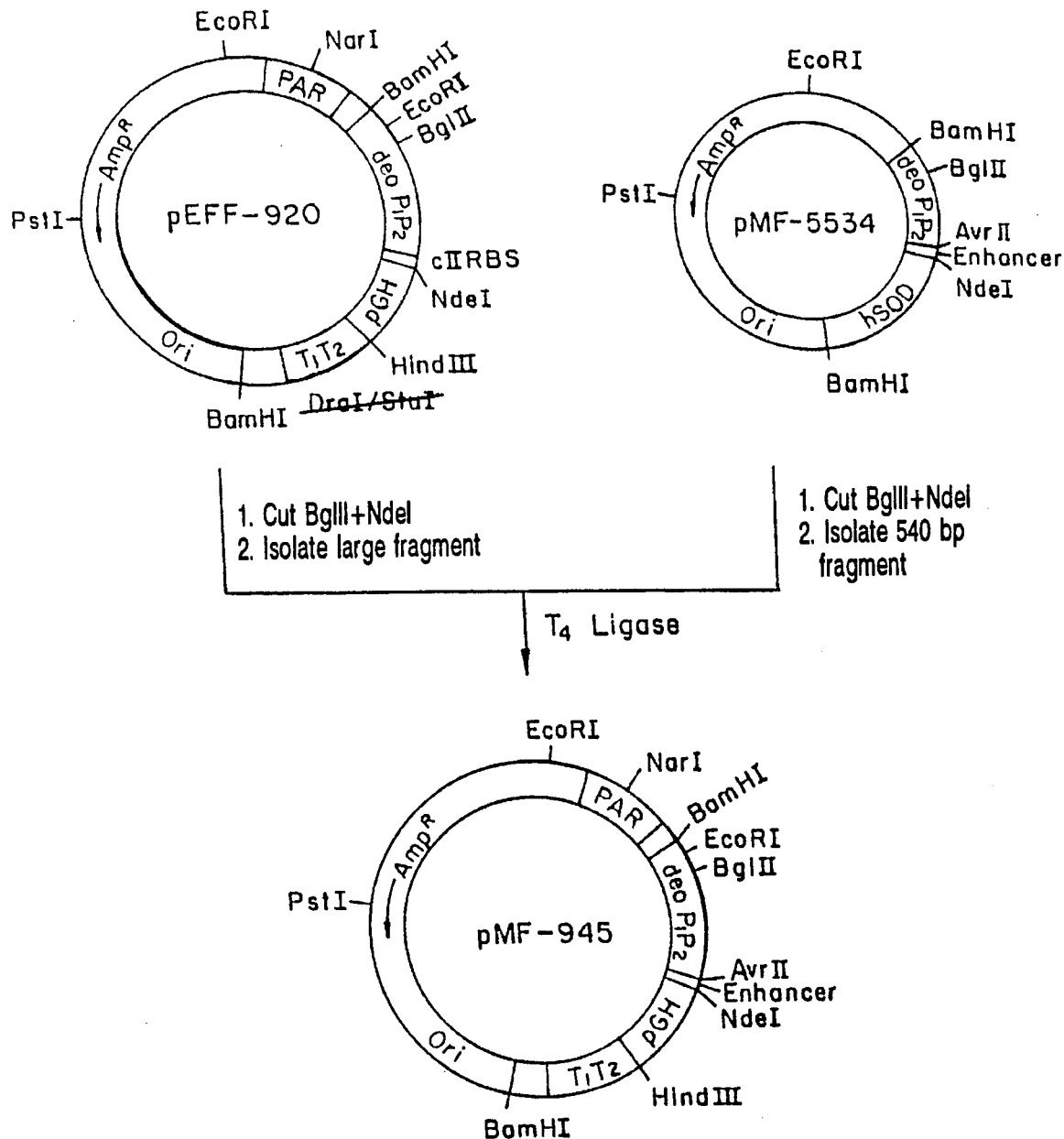

FIG. 45: Construction of plasmid pMF-945

Plasmid pEFF-920 (FIG. 39 and ATCC Accession No. 67706) was cleaved with BglII and NdeI, and the large fragment was isolated. This fragment was ligated to the small 540 bp fragment produced by cleaving plasmid pMF-5534 (FIG. 43) with BglII and NdeI. This produces plasmid pMF-945 which harbors the PAR sequence and in 5' to 3' order the deo P1-P2 promoter sequences, the modified deo RBS with the enhancer sequence, the pGH analog coding sequence and the $T_1T_2$ transcription termination sequences. Plasmid pMF-945 is a high level expressor of pGH analog protein.

Figure 46:
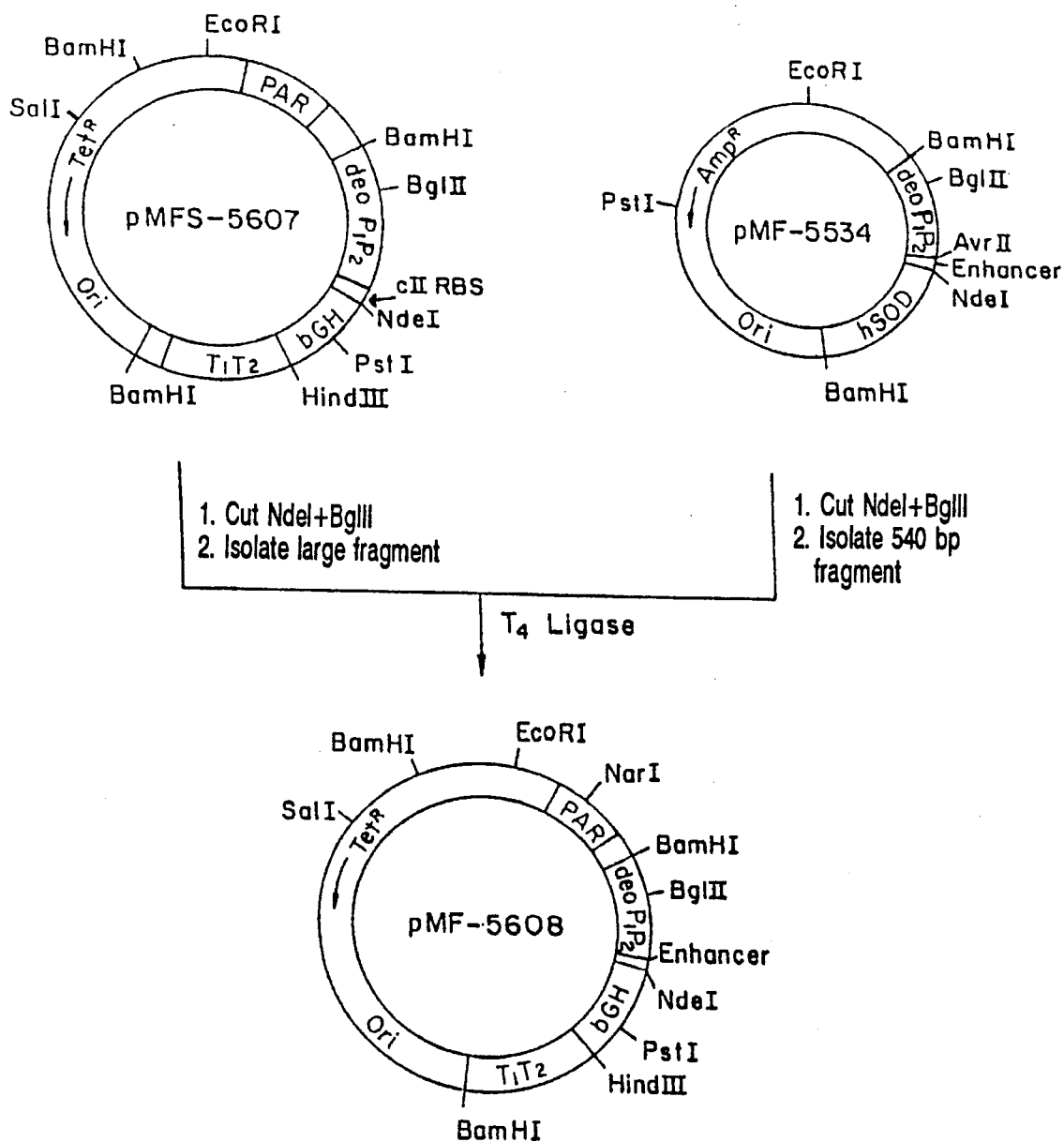

FIG. 46: Construction of plasmid pMF-5608

Plasmid pMFS-5607 (ATCC Accession No. 67704) is similar to plasmid pMFS-5605 (FIG. 42) except that the ampicillin resistance gene has been replaced by one for tetracycline resistance using the same method as described in FIG. 7. Plasmid pMFS-5607 was cleaved with NdeI and BglII and the resulting large fragment was ligated to the small (540 bp) fragment produced by cleaving pMF-5534 (FIG. 43) with NdeI and BglII. The resulting plasmid, designated pMF-5608 contains the PAR sequence and in 5' to 3' order, the deo P1-P2 promoter sequence, the modified deo RBS with the AT rich sequence (the enhancer), the bGH analog coding sequence and the $T_1T_2$ transcription termination sequences. It is a low level expressor of bGH analog protein.

Figure 47:
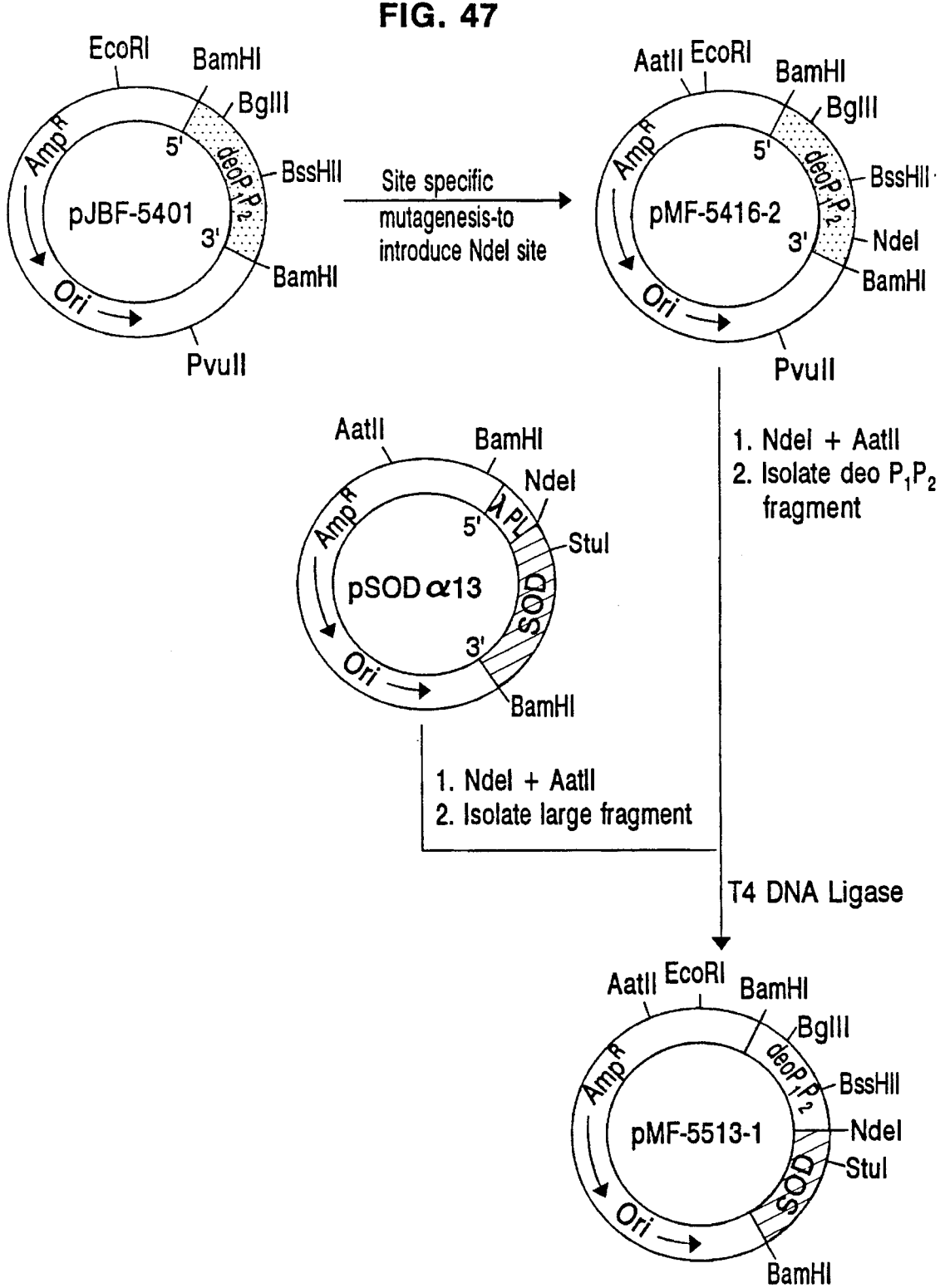

FIG. 47: Construction of plasmid pMF-5513-1

Site specific mutagenesis of plasmid pJBR-5401 was carried out as described in FIG. 2 and resulted in the production of plasmid pMF-5416-2 which contains the complete sequence of the deo P1-P2 promoters. This plasmid was cleaved with NdeI and AatII and the small deo P1-P2 fragment was isolated and ligated to the large fragment obtained by digestion of plasmid pSODα13 by NdeI and AatII (see FIG. 3).

The resulting plasmid, pMF-5513-1 contains in 5' to 3' order the complete deo P1-P2 promoter sequence deo P1 -P2 promoter sequence and the hSOD analog coding sequence. This plasmid is believed to be identical to plasmid pMF-553 1 on the basis of restriction enzyme analysis.

Figure 48:
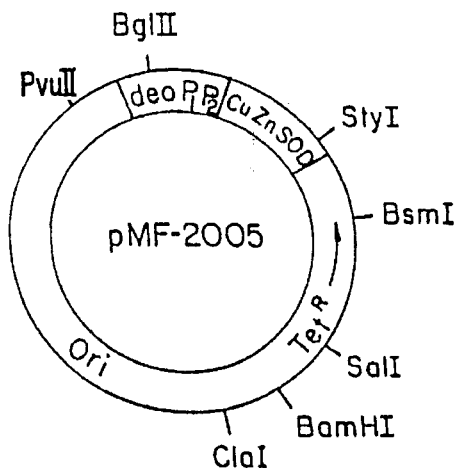
Figure 48:
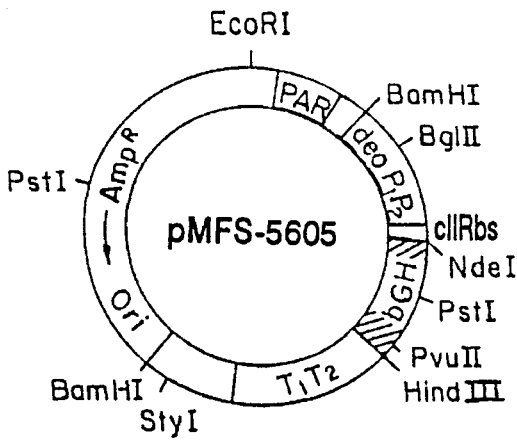
Figure 48:
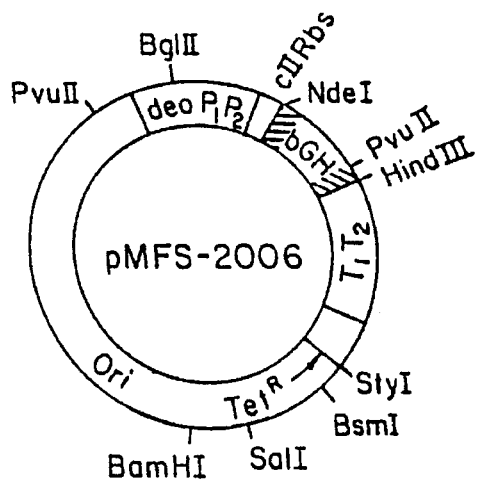

FIG. 48: Construction of plasmid pMFS-2006

The large fragment from plasmid pMF-2005 (FIG. 9) cleaved with BglII and StyI was ligated by T4 ligase to the small fragment obtained from plasmid pMFS-5605 (FIG. 42) cleaved with BglII and StyI. The resulting plasmid, designated pMFS-2006 harbors the tetracycline resistance gene and contains in 5' to 3' order the deo P1-P2 promoter sequence, the cII ribosomal binding site, the bGH analog coding sequence and the $T_1T_2$ transcription termination coding sequences. This plasmid directs high level expression of bGH analog protein (met-asp-gln-bGH).

Figure 49:
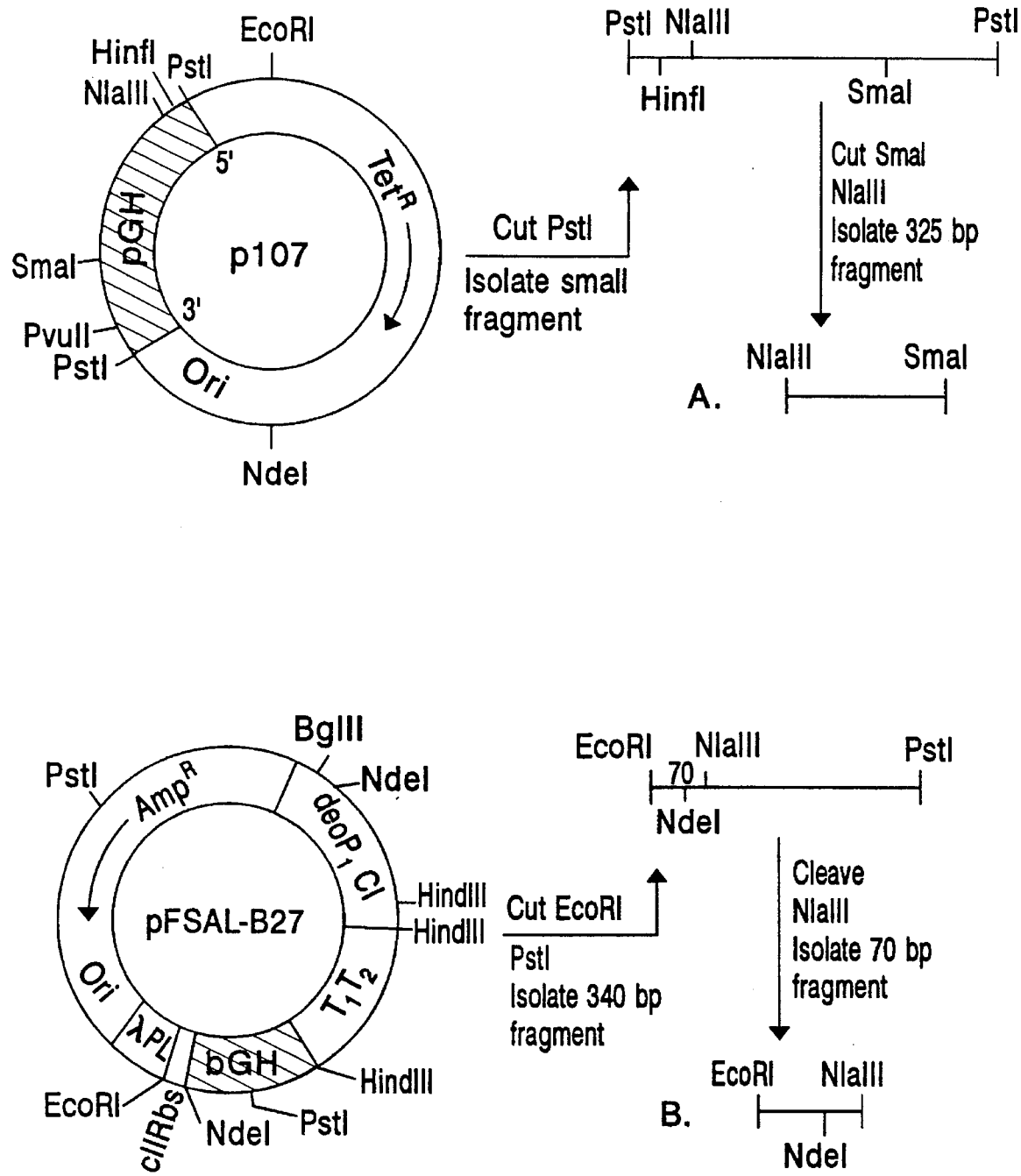

FIG. 49: Production of fragments using NlaIII for use in construction of pGH 30-2

A. An oligo dT-primed cDNA library of pig pituitary mRNA was C-tailed and inserted into plasmid pBR322 which had been PstI-cleaved and G-tailed. It was transformed into *Escherichia coli* strain HB101 and selection was done on Tet LB plates. Hybridization to a bGH probe identified plasmid p107 (also called pPGH cDNA 107) which contains the full length coding sequence of pGH analog plus the leader sequence. Plasmid 107 was cut with PstI and the small fragment produced containing the pGH analog coding sequence (deleted for one glycyl residue), was cleaved with SmaI and NlaIII. The 325 bp fragment produced, containing the central section of the pGH sequence, was isolated from 2% soft agarose gels, and purified by phenol.

B. Plasmid pFSAL-B27 (FIG. 24 and ATCC Accession No. 67071) was cleaved with EcoRI and PstI. The 340 bp fragment was isolated and cleaved with NlaIII and the resulting 70 bp fragment, containing the cII ribosomal binding site and the 5' end of the bGH analog sequence (identical to the 5' end of the pGH analog sequence), was isolated from 2% soft agarose gels and purified by phenol.

Figure 50:
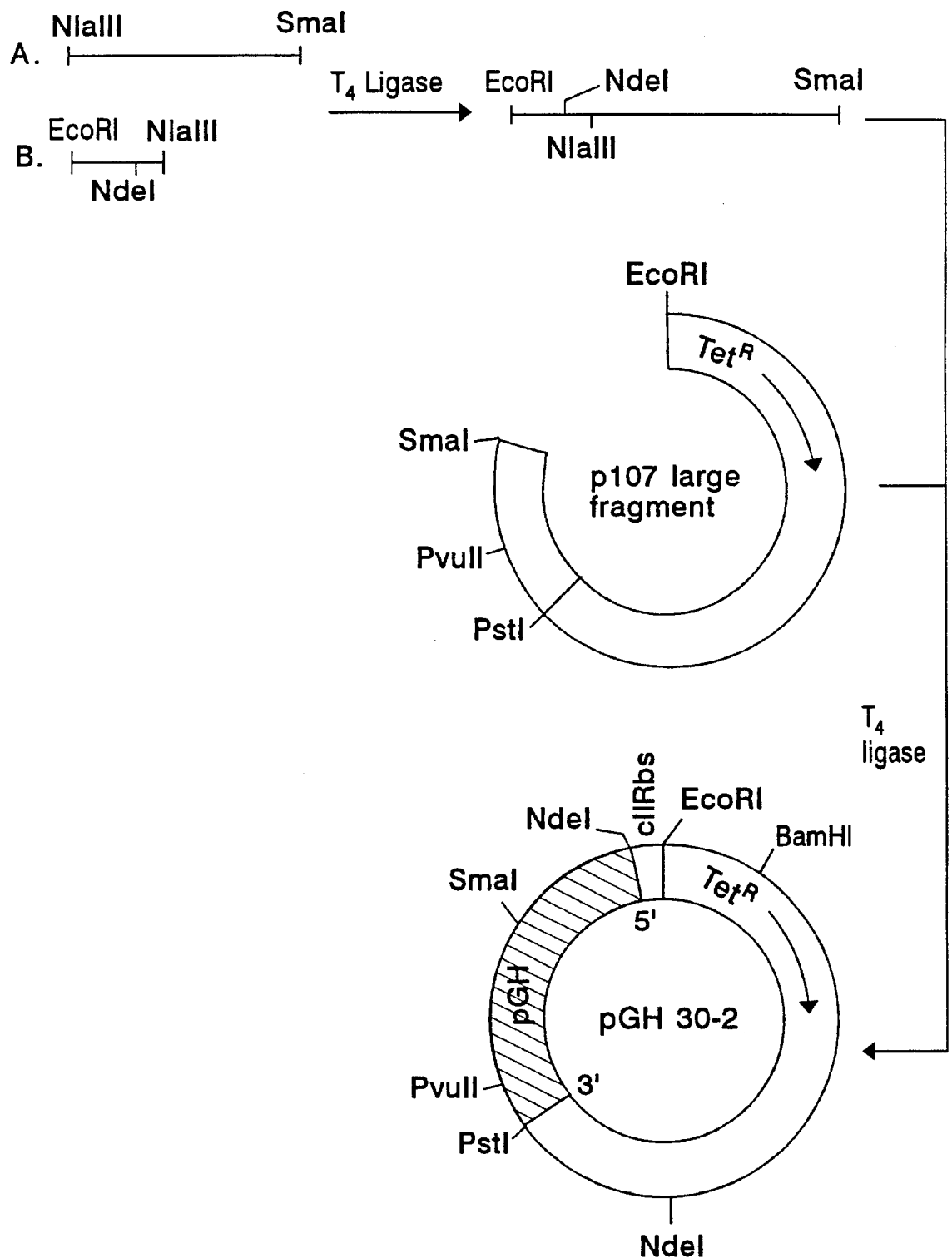

FIG. 50: Production of plasmid pGH 30-2

The two fragments produced as described in FIG. 49 were ligated by T4 ligase and then ligated to the large fragment obtained by cleaving plasmid p107 with EcoRI and SmaI. This produced plasmid pGH 30-2 which contains the cII ribosomal binding site and the full length pGH analog coding sequence.

Figure 51:
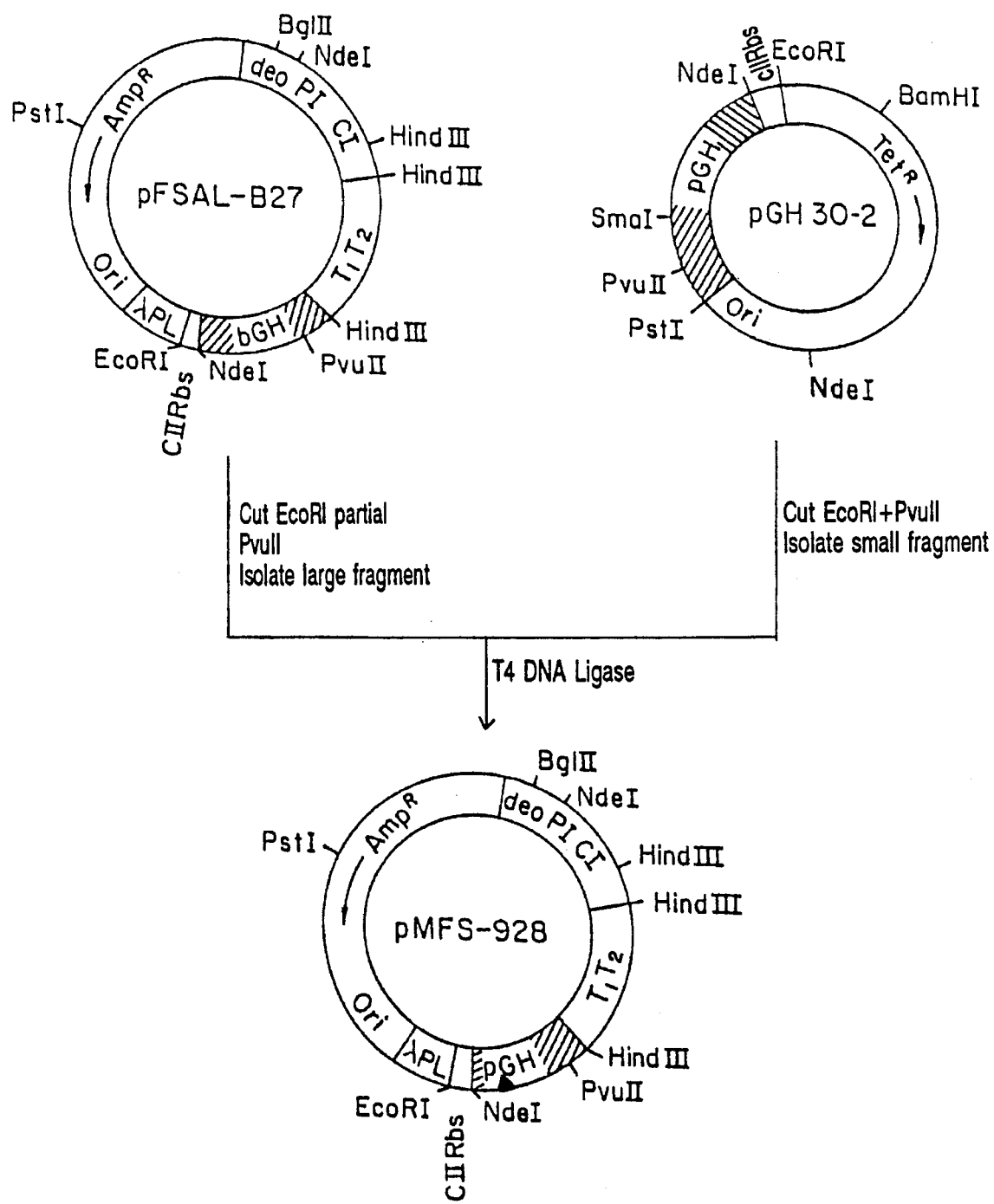

FIG. 51: Production of plasmid pMFS-928

The large fragment from plasmid pFSAL B27 (FIG. 49) after partial EcoRI and PvuII cleavage was ligated to the small fragment produced from plasmid pGH 30-2 cleaved with EcoRI and PvuII. The resulting plasmid, designated pMFS-928 contains the ampicillin-resistance gene and in 5' to 3' order the λ $P_L$, the cII ribosomal binding site, the pGH analog coding sequence and the $T_1T_2$ transcription termination sequences; it further contains the cI repressor sequence under the control of the truncated deo P1 promoter.

Plasmid pMFS-928 directs expression of met-asp-gln-pGH possibly deleted for one glycyl residue. Preliminary sequence data indicated that this glycyl residue corresponds to position 39 of naturally-occurring pGH; the additional N-terminal sequence met-asp-gln in the pGH analog corresponds to positions −3, −2 and −1. At present, it is unclear if there is a glycyl residue deleted in plasmid pMFS 928, due to the problem of condensation of G residues in DNA sequence analysis. Analysis of the complementary strand is underway to determine if the complete pGH analog sequence is present or not; if the sequence is complete, then plasmids pMFS 928 and pMFS 929 are identical.

Figure 52:
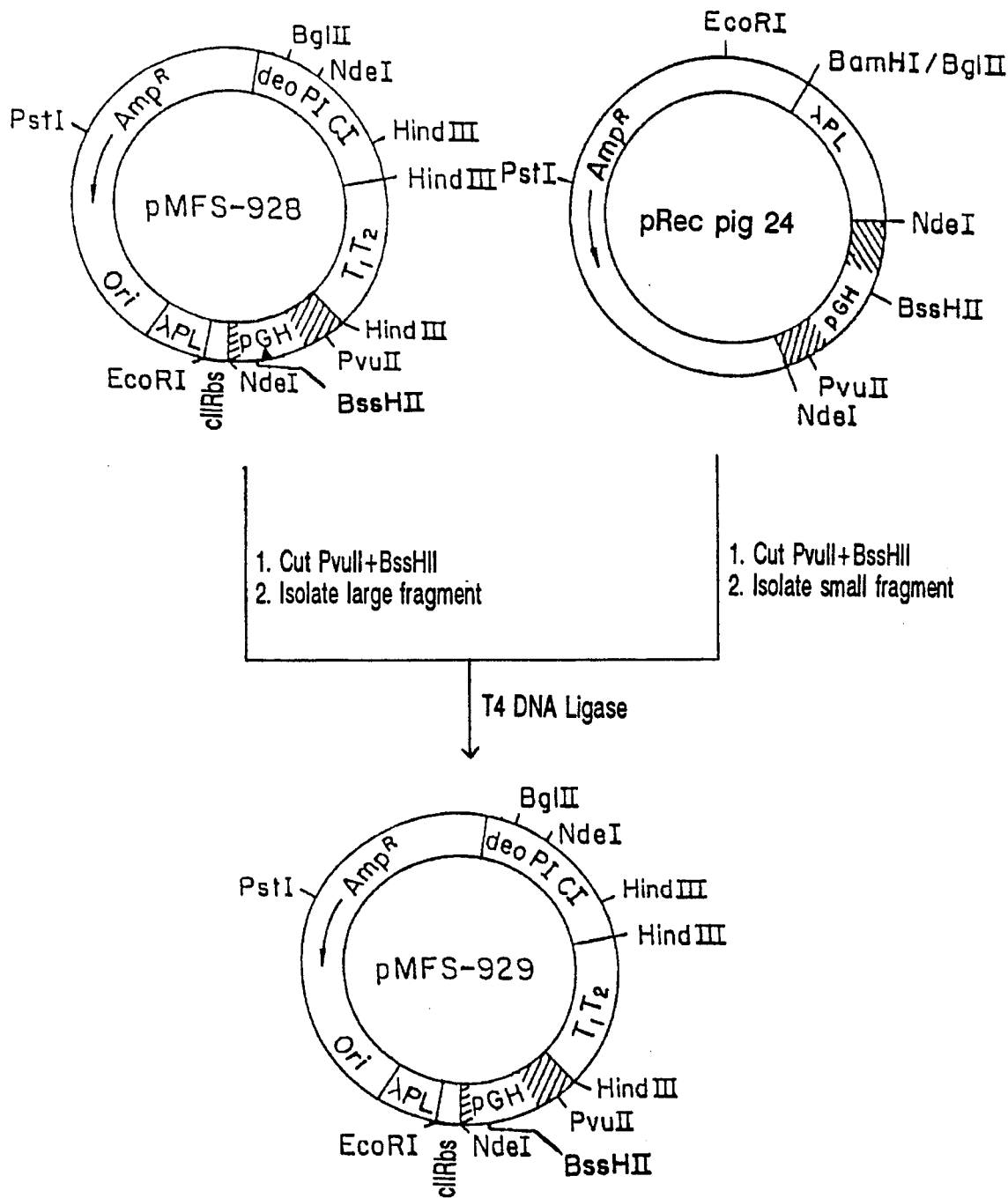

FIG. 52: Production of plasmid pMFS-929

The large fragment from plasmid pMFS-928 after PvuII and BssHII cleavage was ligated to the small fragment produced from plasmid pRec pig 24 (ATCC Accession No. 53433 and FIG. 36) cleaved with PvuII and BssHII. The resulting plasmid, designated pMFS-929, contains the ampicillin resistance gene and in 5' to 3' order the λ $P_L$, the cII ribosomal binding site the full length non-deleted pGH analog coding sequence and the $T_1T_2$ transcription termination coding sequences; it further contains the cI repressor sequence under the control of the truncated deo P1 promoter. It has been deposited in the ATCC under Accession No. 67705.

DETAILED DESCRIPTION OF THE INVENTION

A double-stranded DNA plasmid has been developed which upon introduction into a suitable bacterial host cell, e.g., *Escherichia coli*, renders the host cell capable of effecting expression of a desired, naturally-occurring, eucaryotic polypeptide or a polypeptide analog thereof having the biological activity of, and an amino acid sequence which is substantially the same as, yet different from, that of the naturally-occurring polypeptide and thereby effecting production of the polypeptide or polypeptide analog comprising in 5' to 3' order the following:

a) DNA which includes in 5' to 3' order the tandem promoters deo P1 and deo P2;

b) DNA which includes a ribosomal binding site for rendering mRNA transcribed from the DNA encoding the polypeptide or polypeptide analog capable of binding to ribosomes within the host cell;

c) an ATG initiation codon; and d) the DNA encoding the polypeptide or polypeptide analog in phase with the ATG initiation codon;

and which additionally includes a DNA sequence comprising an origin of replication from the bacterial plasmid capable of autonomous replication in the host cell and a DNA sequence which contains a gene associated with a selectable or identifiable phenotypic trait which is manifested when the plasmid is present in the host cell.

Suitable *Escherichia coli* host cells into which the double-stranded DNA may be introduced include Sϕ732, Sϕ744, MC1061, Sϕ540, Sϕ928, Sϕ929, Sϕ930 or wild-type *Escherichia coli* (ATCC Accession No. 12435). Preferred *Escherichia coli* host cells are cells which contain no functional deo R and cyt R repressor such as *Escherichia coli* strains Sφ744 and Sφ732.

*Escherichia coli* cell Sφ732, which contains plasmid pMF-2005, has been deposited with the American Type Culture Collection, Rockville, Md. 20852, U.S.A. under ATCC Accession No. 67362. The *Escherichia coli* wild-type strain (ATCC Accession No. 12435) is freely available from the Public Collection of the ATCC. Other host cells are known in the art. See Table I at page 84. The phenotype of these cells are also described in Table IA. The *Escherichia coli* strain MC1061 has been described by M. Casadaban and S. N. Cohen, J. Mol. Biol. 138: 179–207 (1980).

The invention also provides a variety of F⁻ *Escherichia coli* host cells which may be used as host cells for the plasmids. While specific F⁻ host strains used are described in more detail in Example 21, it will be understood by those skilled in the art that any suitable F⁻ *Escherichia coli* host strain may be used. Specific examples of *Escherichia coli* hosts which may be used include F⁻MG1655, F⁻W3110, F⁻W2637, F⁻MM294, F⁻1000 and F⁻1100. These strains are discussed in greater detail in Example 21.

Suitable naturally-occurring polypeptides which may be produced by the plasmid of the invention include human copper/zinc superoxide dismutase, human manganese superoxide dismutase, human glutathione peroxidase, human growth hormone, bovine growth hormone, porcine growth hormone, human apolipoprotein E or various domains of the fibronectin molecule. Of course, it will be understood by those skilled in the art that the plasmids may also contain DNA encoding other desired, naturally-occurring polypeptides.

The double-stranded DNA plasmid of the invention also includes the tandem promoters deo P1 and deo P2. As is described in greater detail in Example 1, in order to clone the deo P1-P2 operator/promoter region, it was first necessary to isolate and purify the deo operon. The deo operon was isolated from *Escherichia coli* Sφ1084 which is described in Buxton et al., J. Bacteriol. 136: 668–681 (1978). The method of purification of the deo operon and of constructing a plasmid containing the tandem promoters deo P1 and deo P2 is described in further detail in Example 1.

Various ribosomal binding sites for rendering mRNA transcribed from DNA encoding a desired polypeptide or polypeptide analog capable of binding to ribosomes within the host cell are also contemplated by the invention. One ribosomal binding site which may be used is the natural deo ribosomal binding site derived from the deo operon. A preferred ribosomal binding site which has been used is derived from the deo operon and has a two-base alteration in sequence downstream from the Shine-Dalgarno sequence at nucleotides −1 and −3 in relation to the A of the initiation codon. This ribosomal binding site is described in greater detail in the Description of FIG. 2.

Another preferred ribosomal binding site which has been used is the cII ribosomal binding site from λ bacteriophage having the sequence:

TAAGGAAATACTTACAT
ATTCCTTTATGAATGTA.

Other suitable ribosomal binding sites which may be used include a mutant cII ribosomal binding site from λ bacteriophage having the sequence:

TAAGGAAGTACTTACAT
ATTCCTTCATGAATGTA;

the natural β-lactamase ribosomal binding site derived from pBR322;

a synthetic oligonucleotide having the sequence:

AATTCGAGCGCAAGGAAACAGGCTCA
    GCTCGCGTTCCTTTGTCCGAGTAT; and synthetic oligonucleotide having the sequence:

AATTCAATAATATTGAAAAAGGAAGAG
    GTTATTATAACTTTTTCCTTCTCAT.

Another ribosomal binding site which has been used in the subject invention is a synthetic nucleotide having the sequence:

GACAAGCCTAGGTTTGTTTAACTTTAAGGAGAAATCATA
CTGTTCGGATCCAAACAAATTGAAATTCCTCTTTAGTAT.

Plasmids of the invention also contain an ATG initiation codon. The DNA encoding the desired naturally-occurring eucaryotic polypeptide or polypeptide analog is in phase with the ATG initiation codon.

The plasmid of the invention also includes a DNA sequence comprising an origin of replication from a bacterial plasmid capable of autonomous replication in the host cell. Suitable origins of replication may be obtained from numerous sources. One such source, plasmid pBR322, is freely available from the Public Collection of the American Type Culture Collection as ATCC Accession No. 37017. The origin of replication may also be derived from pOP1Δ6. This plasmid is well-known in the art and is described by D. H. Gelfand et al., PNAS 15: 5869–5873 (1978) and by M. Muessing et al., Cell 24:235 (1981).

A DNA sequence which contains a gene associated with a selectable or identifiable phenotypic trait which is manifested when the plasmid is present in the host cell is also a component of the plasmid. Suitable genes include those associated with temperature sensitivity or drug resistance, e.g., resistance to ampicillin, chloramphenicol or tetracycline.

The plasmid of the invention is preferably a circular, closed plasmid.

As described above, the plasmids of the invention may be used to produce numerous, naturally-occurring polypeptides or polypeptide analogs thereof. Among the plasmids contemplated by the invention are plasmids which produce human copper/zinc superoxide dismutase, human manganese superoxide dismutase, human glutathione peroxidase, human growth hormone, bovine growth hormone, porcine growth hormone, human apolipoprotein E or fibronectin domains.

The plasmids of the invention may also be used to produce eucaryotic polypeptide analogs having the biological activity of and an amino acid sequence which is substantially the same as, yet different from, that of the naturally-occurring polypeptide or analogs which have an amino acid sequence identical to that of the naturally-occurring polypeptide but differ in that the polypeptide is acetylated or non-glycosylated, for example.

The plasmids of the invention have been used to produce an analog of naturally-occurring human copper/zinc superoxide dismutase comprising a dimer of two polypeptide subunits each of which has an amino acid sequence identical to that of naturally-occurring human copper/zinc superoxide dismutase but which is not acetylated at its amino terminus. Plasmid pMF 5531, having the restriction map shown in FIG. 4, produces such an analog of human copper/zinc superoxide dismutase. Other plasmids which produce analogs of human copper/zinc superoxide dismutase as defined above include plasmid pMF 5519, having the restriction map shown in FIG. 5; plasmid pMF 558-26 having the restriction map shown in FIG. 6; plasmid pMF 5534, having the restriction map shown in FIG. 43; plasmid pMF-5520, having the restriction map shown in FIG. 7; plasmid pMF 2005, having the restriction map shown in FIG. 9; plasmid pMFS 5533A, having the restriction map shown in FIG. 17; and plasmid pMFS-5538, having the restriction map shown in FIG. 18.

The plasmids of the invention have also been used to produce a polypeptide analog of human growth hormone, having the amino acid methionine attached to the N-terminus of the naturally-occurring human growth hormone polypeptide sequence. An example of such a plasmid is plasmid pTVR 568-4, having the restriction map shown in FIG. 11.

The plasmids of the invention have also been used to produce an analog of bovine growth hormone having the amino acids methionine, aspartic acid and glutamine attached to the N-terminus of the naturally-occurring bovine growth hormone polypeptide sequence. Examples of plasmids for producing analogs of bovine growth hormone as defined above include plasmid pMFS-5600, having the restriction map shown in FIG. 12; plasmid pMFS 5627, having the restriction map shown in FIG. 40; plasmid pMFS-5603, having the restriction map shown in FIG. 41; plasmid pMFS-5605, having the restriction map shown in FIG. 42; and plasmid pMFS 2006, having the restriction map shown in FIG. 48.

The plasmids of the invention have also been used to produce an analog of porcine growth hormone having the amino acids methionine, aspartic acid and glutamine attached to the N-terminus of the naturally-occurring porcine growth hormone polypeptide sequence. Examples of plasmids for producing analogs of porcine growth hormone as defined above include plasmid pEFF-905, having the restriction map shown in FIG. 38; and plasmid pEFF-920, having the restriction map shown in FIG. 39.

The plasmids of the invention have also been used to produce numerous fused polypeptides. Examples of fused polypeptides which have been produced with the plasmids of the invention include plasmid pDGE4-3, having the restriction map shown in FIG. 10 and used to produce a manganese superoxide dismutase-glutathione peroxidase fused polypeptide; and plasmid pTVR 580-35, having the restriction map shown in FIG. 19 and used to produce a human growth hormone-apolipoprotein E fused polypeptide.

The subject invention also provides host plasmid systems for producing a naturally-occurring eucaryotic polypeptide or a polypeptide analog thereof comprising the various plasmids of the invention in a suitable *Escherichia coli* host. The *Escherichia coli* host containing the plasmid is selected from the group of *Escherichia coli* hosts consisting of Sϕ744, Sϕ732, wild-type (ATCC Accession No. 12435), Sϕ540, Sϕ928, Sϕ929, MC1061, and Sϕ930.

The *Escherichia coli* host of the host plasmid system may also be an F⁻ strain. While the host may be any F⁻ strain known to those skilled in the art, specific F⁻ strains which may be used in the host plasmid system include the following F⁻ strains: F⁻MG1655; F⁻W3110; F⁻W2637; F⁻MM294; F⁻1000; and F⁻1100.

The invention also provides a host plasmid system for producing an analog of naturally-occurring human copper/zinc superoxide dismutase comprising a dimer of the polypeptide subunits each of which has an amino acid sequence identical to that of naturally-occurring human copper/zinc superoxide dismutase but which is not acetylated at its amino terminus comprising a plasmid containing DNA encoding the analog of human copper/zinc superoxide dismutase, such as the plasmids discussed above, in a suitable *Escherichia coli* host.

The invention also provides a host plasmid system for producing a superoxide dismutase-glutathione peroxidase fused polypeptide comprising a plasmid containing DNA encoding the fused polypeptide, i.e., pDGE4-3, in a suitable *Escherichia coli* host.

The invention also provides a host plasmid system for producing a polypeptide analog of human growth hormone having the amino acid methionine attached to the N-terminus of the naturally-occurring human growth hormone comprising a plasmid containing DNA encoding an analog of human growth hormone, i.e., pTVR 568-4, in a suitable *Escherichia coli* host.

The invention also provides a host plasmid system for producing an analog of bovine growth hormone having the amino acids methionine, aspartic acid and glutamine attached to the N-terminus of the naturally-occurring bovine growth hormone polypeptide comprising a plasmid containing DNA encoding an analog of bovine growth hormone, i.e., plasmids pMFS-5600, pMFS-5627, pMFS-5603, pMFS-5605, or pMFS-2006, in a suitable *Escherichia coli* host.

The invention also provides a host plasmid system for producing an analog of porcine growth hormone having the amino acids methionine, aspartic acid and glutamine attached to the N-terminus of the naturally-occurring porcine growth hormone polypeptide comprising a plasmid containing DNA encoding an analog of porcine growth hormone, i.e., plasmid pEFF-905 or pEFF-920, in a suitable *Escherichia coli* host.

The invention also provides a host plasmid system for producing a human-growth hormone-apolipoprotein fused polypeptide comprising a plasmid containing DNA encoding the fused polypeptide, i.e., plasmid pTVR 580-35, in a suitable *Escherichia coli* host.

In another aspect of the invention, the invention provides a method for producing a naturally-occurring polypeptide or a polypeptide analog thereof such as the analogs defined above which comprises growing the host-plasmid system of the invention under conditions permitting production of the polypeptide or analog and recovering the resulting polypeptide or analog.

Using the method of the invention, an analog of naturally-occurring human copper/zinc superoxide dismutase comprising a dimer of two polypeptide subunits each of which has an amino acid sequence identical to that of the naturally-occurring polypeptide but which is not acetylated at the N-terminus, a manganese superoxide dismutase-glutathione peroxidase fused polypeptide, a methionine polypeptide analog of human growth hormone, a met-asp-gln polypeptide analog of bovine growth hormone, a met-asp-gln polypeptide analog of porcine growth hormone and a human growth hormone-apolipoprotein E fused polypeptide have been produced by growing host plasmid systems comprising plasmids which contain DNA encoding each of these polypeptides, analogs or fused polypeptides and a suitable Escherichia coli host, under suitable conditions permitting production of the polypeptides, analogs or fused polypeptides and recovering the resulting polypeptide, analog or fused polypeptide.

The method for producing a naturally-occurring polypeptide or polypeptide analog comprises low aeration conditions as is described in greater detail in Examples 2, 16 and 17. Example 2 sets forth optimal growth conditions for production of an analog of human copper/zinc superoxide dismutase such as the analog defined above. Examples 16 and 17 set forth optimal conditions for production of analogs of porcine and bovine growth hormones.

The invention further provides a method for producing constitutively a desired naturally-occurring polypeptide or polypeptide analog wherein a carbon source other than glucose is used in the growth medium. While not wishing to be bound by theory, it is believed that DNA is transcribed at lower levels when the DNA to be expressed is under the control of a deo P2 promoter/operator region and glucose is present in the medium. Glucose appears to be implicated in reducing levels of transcription. Suitable non-glucose carbon sources which may be used in the growth medium include glycerol, fructose, succinate, sodium lactate and sodium malate although it will be understood by those skilled in the art that other sources may be used.

The invention also provides a method for producing desired polypeptides or analogs which comprises initially growing the Escherichia coli cells in glucose, thereby reducing the transcription level of DNA encoding the desired polypeptide while the Escherichia coli cells are growing, and subsequently adding a non-glucose carbon source after depletion of the glucose.

Non-glucose carbon sources which may be used in this aspect of the invention include glycerol, succinate, sodium lactate, fructose and sodium malate. Other non-glucose carbon sources which may be used will be readily appreciated by those skilled in the art.

Suitable growth media which may be used include LB or minimal salt media. The type of medium used and elements contained in the solution are described in greater detail in Example 2. Other elements which may be used in the solution will be readily appreciated by those skilled in the art.

Another factor which has been demonstrated to increase production of desired polypeptides is low aeration of the growth medium.

The invention further provides a method wherein the polypeptide or polypeptide analog produced in the host plasmid system is secreted into the medium in which the host plasmid system is grown upon addition of a divalent metal ion to the growth medium.

While preferred divalent metal ions include $Cu^{+2}$ and $Zn^{+2}$, it will be understood by those skilled in the art that any suitable divalent metal ion may be used. The invention further contemplates a process wherein the divalent ion is a mixture of $Cu^{+2}$ and $Zn^{+2}$ metal ions. Once again, those skilled in the art will appreciate that a mixture of any suitable divalent metal ions may be used. It should also be noted that the polypeptide is secreted into the medium, not the periplasmic space.

It should be further noted that when the plasmid expressing the desired polypeptide contains a translational enhancer, such as described below, yields of polypeptide have been found to be surprisingly higher when growth of the Escherichia coli cells is conducted at about 30° C.

In a different embodiment of this invention, the invention provides a double-stranded DNA plasmid which upon introduction into a suitable bacterial host cell, e.g., Escherichia coli, renders the host cell capable, upon increasing the temperature of the host cell to a temperature at which a cI thermolabile repressor is inactivated, of effecting expression of DNA encoding a desired, naturally-occurring eucaryotic polypeptide or a polypeptide analog thereof having the biological activity of, and an amino acid sequence which is substantially the same as, yet different from, that of naturally-occurring polypeptide, and thereby effecting production of the polypeptide of polypeptide analog thereof comprising in 5' to 3' order the following:

a) DNA which includes the promoter and operator $P_L O_L$ from λ bacteriophage;
b) DNA which includes a ribosomal binding site for rendering mRNA transcribed from the DNA encoding the polypeptide or polypeptide analog capable of binding to ribosomes within the host cell;
c) an ATG initiation codon; and
d) DNA encoding the polypeptide or polypeptide analog in phase with the ATG initiation codon;

and which additionally comprises in 5' to 3' order a DNA sequence which contains the deo P1 promoter or part thereof and DNA which encodes a cI thermolabile repressor of the λ $P_L$ promoter, expression of the repressor being under the control of the deo P1 promoter or part thereof;

and further includes a DNA sequence comprising an origin of replication from a bacterial plasmid capable of autonomous replication in the host cell and a gene associated with a selectable or identifiable phenotypic trait which is manifested when the plasmid is present in the host cell.

Suitable Escherichia coli host cells into which the plasmid described above may be introduced are the same as those described above, including the F⁻ host strains described above. Preferred Escherichia coli strains include wild-type (ATCC Accession No. 12435) and Escherichia coli strain MC1061 (ATCC Accession No. 67361, deposited with the ATCC on Mar. 20, 1987).

One aspect of the invention is the presence of DNA encoding a λ cI 857 thermolabile repressor protein in the plasmid. Since production of the λ repressor protein does not depend on the presence of λ genes in the host chromosome, the plasmid is termed an "independent" plasmid.

Suitable naturally-occurring polypeptides which may be produced by the plasmids of the invention include human growth hormone, bovine growth hormone, porcine growth hormone, human copper/zinc superoxide dismutase, apolipoprotein E or fibronectin domains. Of course, it will be understood by those skilled in the art that the plasmid may also contain DNA encoding other desired naturally-occurring polypeptides.

An important component of the independent plasmid is the ribosomal binding site and suitable binding sites include any of those discussed earlier in the application.

The plasmid of the invention also contains an ATG initiation codon. The DNA encoding the desired naturally-occurring eucaryotic polypeptide or analog is in phase with the ATG codon.

This independent plasmid includes an origin of replication from a bacterial plasmid capable of autonomous replication in the host. Suitable origins of replication may be obtained from a number of sources, for example, from plasmid pBR322. This strain is freely available from the American Type Culture Collection as ATCC Accession No. 37017. The origin of replication may also be derived from pOP1Δ6.

A DNA sequence which contains a gene associated with a selectable or identifiable phenotypic trait which is manifested when the independent plasmid is present in the host cell is also a component of the plasmid. Suitable genes include those associated with temperature sensitivity or drug resistance, e.g., resistance to ampicillin, chloramphenicol or tetracycline.

The plasmid of the invention is preferably a circular, closed plasmid.

As described above, the plasmids of the invention may be used to produce numerous, naturally-occurring polypeptides or polypeptide analogs thereof. Among the plasmids which are contemplated are plasmids which produce human copper/zinc superoxide dismutase, human growth hormone, bovine growth hormone, porcine growth hormone, apolipoprotein E and fibronectin domains. The plasmids of the invention may also be used to produce eucaryotic polypeptide analogs having the biological activity of and an amino acid sequence which is substantially the same as, yet different from, that of the naturally-occurring polypeptide.

The plasmid of the invention has been used to produce a polypeptide analog of bovine growth hormone having the amino acids methionine, aspartic acid and glutamine attached to the N-terminus of the naturally-occurring bovine growth hormone polypeptide sequence. An example of such a plasmid is plasmid pFSAL-130-B27, having the restriction map shown in FIG. 24 and deposited under ATCC Accession No. 67071 and plasmid pMF-B27 described in Example 23.

The plasmid of the invention has also been used to produce a polypeptide analog of human growth hormone having the amino acid methionine attached to the N-terminus of the human growth hormone polypeptide sequence. An example of such a plasmid is plasmid pTVR 723-6 described in Example 22.

The plasmid of the invention has also been used to produce a polypeptide analog of porcine growth hormone having the amino acids methionine, aspartic acid and glutamine attached to the N-terminus of the naturally-occurring porcine growth hormone polypeptide sequence. Examples of plasmids for producing analogs of porcine growth hormone as defined above include plasmid pEFF-902, having the restriction map shown in FIG. 36; plasmid pEFF-9021, having the restriction map shown in FIG. 37; and plasmid pMFS 929, having the restriction map shown in FIG. 52 and deposited under ATCC Accession No. 67705 on May 23, 1988.

The plasmid of the invention has also been used to produce an analog of naturally-occurring human copper/zinc superoxide dismutase comprising a dimer of two polypeptide subunits each of which has an amino acid sequence identical to that of naturally-occurring human copper/zinc superoxide dismutase but which is not acetylated at its amino terminus. An example of such a plasmid is plasmid pSODβMAX-12-cI, having the restriction map shown in FIG. 25.

The plasmid of the invention may also be used to produce an analog of apolipoprotein E. An example of a plasmid producing a met-leu-leu-leu-met apolipoprotein E analog is plasmid pTVR 700-2, having the restriction map shown in FIG. 26; and an example of a plasmid producing a met-apolipoprotein analog is plasmid pTVR 590-4, having the restriction map shown in FIG. 27. Plasmid pTVR 714 (also pTVR 721-4) also produces an analog of apolipoprotein E. This plasmid is described in Example 12.

The subject invention also provides host plasmid systems for producing a naturally-occurring eucaryotic polypeptide or a polypeptide analog thereof comprising the various plasmids of the invention in a suitable *Escherichia coli* host. The *Escherichia coli* host may be any of the hosts described above.

The *Escherichia coli* host of the host plasmid system may also be an F$^-$ strain. While the host may be any F$^-$ strain known to those skilled in the art, specific F$^-$ strains which may be used include the following F$^-$ strains: F$^-$MG1655; F$^-$W3110; F$^-$W2637; F$^-$MM294; F$^-$1000; and F$^-$1100.

The invention further provides a host plasmid system for producing a polypeptide analog of bovine growth hormone such as that defined above which comprises a plasmid containing DNA encoding a met-asp-gln bovine growth hormone analog, i.e., plasmid pFSAL-130-B27, in a suitable *Escherichia coli* host. A preferred host for this aspect of the invention is wild-type *Escherichia coli* (ATCC Accession No. 12435).

The invention further provides a host plasmid system for producing a met-asp-gln polypeptide analog of porcine growth hormone which comprises a plasmid containing DNA encoding met-asp-gln porcine growth hormone, i.e., plasmid pEFF-902, pEFF-9021 or pMFS 929, in a suitable *Escherichia coli* host.

The invention further provides a host plasmid system for producing various polypeptide analogs of apolipoprotein E as defined above which comprises a plasmid containing DNA encoding apolipoprotein E, i.e., plasmid pTVR 700-2, pTVR 590-4 or pTVR 714 (also pTVR 721-4), in a suitable *Escherichia coli* host. In a preferred embodiment of the invention, the analog of apolipoprotein E is a met-apolipoprotein E analog and the host is wild-type *Escherichia coli* (ATCC Accession No. 12435) wherein the host plasmid system has been deposited under ATCC Accession No. 67360.

In another aspect of the invention, the invention provides a method for producing a naturally-occurring polypeptide or a polypeptide analog thereof which comprises growing the host plasmid system (wherein the plasmid is an independent plasmid) of the invention under conditions permitting production of the polypeptide or analog and recovering the resulting polypeptide or analog.

Using the method of the invention, a met-asp-gln polypeptide analog of bovine growth hormone, a met-asp-gln polypeptide analog of porcine growth hormone, a polypeptide analog of human copper/zinc superoxide dismutase as defined above, and a polypeptide analog of apolipoprotein E also as defined above, may each be produced by growing host plasmid systems comprising plasmids which contain DNA encoding an analog of bovine growth hormone, an analog of porcine growth hormone, an analog of human copper/zinc superoxide dismutase, and an analog of apolipoprotein E, respectively, and a suitable *Escherichia coli* host, under suitable conditions permitting production of the analogs, respectively, and recovering the resulting analogs.

In another embodiment of the invention, the invention provides a double-stranded DNA plasmid which upon introduction into a suitable *Escherichia coli* host cell renders the host cell capable of effecting expression of DNA encoding a desired polypeptide or a polypeptide analog thereof having the biological activity of, and an amino acid sequence which is substantially the same as, yet different from, that of the naturally-occurring polypeptide, and thereby effecting production of the polypeptide or polypeptide analog comprising in 5' to 3' order the following:

a) DNA which includes in 5' to 3' order the tandem promoters deo P1 and deo P2;
b) an AT rich sequence translational enhancer;
c) an NdeI restriction enzyme site;
d) an ATG initiation codon; and
e) DNA encoding the polypeptide or polypeptide analog in phase with the ATG initiation codon;

and which additionally includes a DNA sequence comprising an origin of replication from a bacterial plasmid capable of autonomous replication in the host cell and a DNA sequence which contains a gene associated with a selectable or identifiable phenotypic trait which is manifested when the plasmid is present in the host cell.

The additional translation enhancer increases production level of polypeptides produced by the plasmids of the invention. It has been found that addition of these AT rich regions greatly enhances expression of DNA encoding desired polypeptides (see Example 18 for greater detail). In a preferred embodiment, it has been found that when *Escherichia coli* cells and plasmids containing the AT rich regions are grown in production media at about 30° C. rather than 37° C., the production level is enhanced still further.

While it will be understood by those skilled in the art that the plasmids may produce any desirable naturally-occurring polypeptide or analog thereof, preferably the plasmid of the invention produces human copper/zinc superoxide dismutase. In a preferred embodiment, the plasmid of the invention is designated pMF 5534 and has been deposited in *Escherichia coli* strain Sϕ930 (F⁻) under ATCC Accession No. 67703.

The invention also provides a host plasmid system for production of an analog of naturally-occurring human copper/zinc superoxide dismutase comprising a dimer of two polypeptide subunits each of which has an amino acid sequence identical to that of naturally-occurring copper/zinc superoxide dismutase but which is not acetylated at its amino terminus comprising a plasmid containing DNA encoding an analog of human copper/zinc superoxide dismutase, i.e., plasmid pMF 5534, in a suitable *Escherichia coli* host.

Suitable hosts for the host plasmid system include Sϕ744, Sϕ732, wild-type (ATCC Accession No. 12435), Sϕ928, Sϕ929, MC1061, and Sϕ930. The host may also be an F⁻ strain.

The invention also provides a method for producing a polypeptide analog of copper/zinc superoxide dismutase such as defined above which comprises growing the host plasmid system under suitable conditions permitting production of the analog and recovering the resulting copper/zinc superoxide dismutase analoog.

In a preferred embodiment, such suitable conditions comprise growing the host plasmid at about 30° C.

Although we have discussed the plasmids and host plasmids of the subject invention in terms of tandem promoters deo P1 and deo P2, it will be appreciated by those skilled in the art, in view of the fact that deo P2 is the stronger promoter, that the subject invention further provides plasmids where deo P2 alone is the promoter.

More specifically, the invention provides a double-stranded DNA plasmid which upon introduction into a suitable *Escherichia coli* host cell capable of effecting expression of a desired, naturally-occurring, eucaryotic polypeptide or a polypeptide analog thereof having the biological activity of, and an amino acid sequence which is substantially the same as, yet different from, that of the naturally-occurring polypeptide and thereby effecting production of the polypeptide or polypeptide analog comprising in 5' to 3' order the following:

a) DNA which includes in the promoter deo P2;
b) DNA which includes a ribosomal binding site for rendering mRNA transcribed from the DNA encoding the polypeptide or polypeptide analog capable of binding to ribosomes within the host cell;
c) an ATG initiation codon; and
d) DNA encoding the polypeptide or polypeptide analog in phase with the ATG initiation codon;

and which additionally includes a DNA sequence comprising an origin of replication from the bacterial plasmid capable of autonomous replication in the host cell and a DNA sequence which contains a gene associated with a selectable or identifiable phenotypic trait which is manifested when the plasmid is present in the host cell.

The subject invention also provides plasmids such as those discussed above which additionally comprise an AT rich sequence translation enhancer.

In addition, it will further be understood by those skilled in the art that the deo P1 promoter may be used alone. An example of such a plasmid is plasmid pMF 5540. Plasmids having a deo P1 promoter may additionally comprise an AT rich sequence translation enhancer.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides into such vectors to form plasmids or the introduction of the resulting plasmids into hosts. The examples also do not include detailed descriptions for conventional methods employed for assaying the polypeptides produced by such host plasmid systems. Such methods are well-known to those of ordinary skill in the art and are described in numerous publications including by way of example the following: T. Maniatis, E. F. Fritsch and J. Sombrook, *Molecular Cloning: A Laboratory Manual*, Cold Spring Harbor Laboratory, New York (1982).

Example 1

Construction of Deo P1-P2 Vector Expressing an hSOD Analog Protein

In order to clone the deo P1-P2 operator/promoter region, it was first necessary to isolate and purify the deo operon.

λ cI 857: DNA encoding the deo operon was isolated from *Escherichia coli* Sϕ1084 harboring a deo transducing phage in a lysogenic state, Buxton et al., J. Bacteriol. 136: 668–681 (1978). The method of purification of the DNA is essentially as described by D. Freifelder, Biochem. Biophys. Res. Commun. 18: 141–144 (1965); and D. Freifelder, Biochem. Biophys. Acta 108: 318–319 (1965). Two liters of *Escherichia coli* culture grown in LB medium were heat-shocked for 30 min at 42° C. and then transferred to 39° C. for 3 hr. The cells were harvested by centrifugation and were resuspended in buffer containing 1–5 mM $MgCl_2$ and a few drops of chloroform to lyse the cells. The lysate was applied on top of a CsCl step gradient and centrifuged for 2 hr at a speed of 25,000 RPM in an SW25 rotor. An opalescent band which formed on top of the highest density cushion of CsCl was isolated and centrifuged with sodium perchlorate to obtain pure phage λ deo DNA.

Construction of pJBF-5401—A Vector Containing the Deo Promoters P1 and P2

The deo P1 and P2 operator/promoter regions are located on a 980 bp AvaII fragment, Valentin-Hansen et al., the EMBO Journal 1: 317 (1982). This fragment was isolated and cloned as follows (see also FIG. 1): deo DNA was cleaved with AvaII and the 5' protruding ends filled in by Klenow-DNA polymerase. BamHI linkers were attached to the mixture of AvaII fragments, and the mixture of AvaII fragments with BamHI linkers was ligated with $T_4$ ligase to BamHI—cleaved pBR322. *Escherichia coli* Sϕ540 (deleted for the deo operon) was transformed with the ligated plasmid mix, and plated on to LB agar containing ampicillin. The clones harboring a BamHI insert containing the deo P1-P2 were identified by hybridization to a $^{32}$P-labeled synthetic DNA frag-ment corresponding to nucleotides 138-167 of the deo promoter.

The nucleotide sequence of the synthetic fragment was:

5'-TTGCCCCAGGTAGACCGGCATCGATGTGAC-3'

Figure 1:
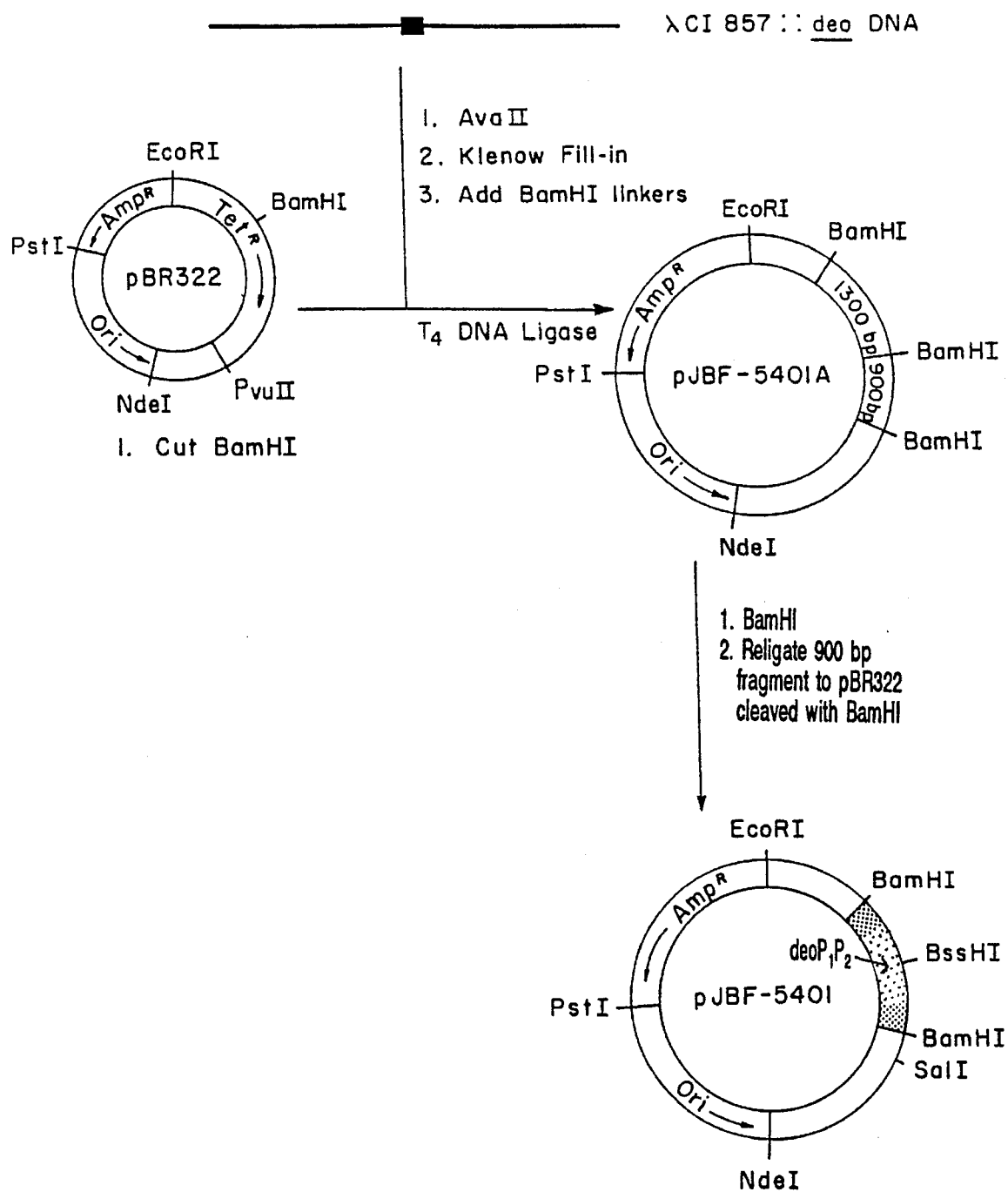
FIG. 1: Construction of pJBF-5401 (cloning of deo P1-P2)

One clone out of several which did hybridize to the primer was picked and used for further analysis. Plasmid DNA isolated from this clone was digested with BamHI and analyzed electrophoretically on agarose gels. Fragments of 900 bp and 1300 bp, in addition to a fragment corresponding to the vector, were observed on the gels. These fragments were subjected to Southern hybridization analysis with the labeled probe. The deo P1-P2 promoters were shown to reside in the 900 bp fragment. To verify further the presence of deo P1-P2, the 900 bp fragment was cleaved with BglII, BSSHII, EcoRI and HpaII. The sizes of fragments generated by these enzymes upon cleavage of the 900 bp fragment were in good agreement with the predicted restriction pattern of the deo P1-P2 sequence. The 900 bp BamHI fragment was recloned in pBR322 as shown in FIG. 1 and the new plasmid obtained which contains the deo P1-P2 promoters was designated pJBF-5401 (ATCC Accession No. 67359).

Construction of pMF-5416—A Vector Containing deo P1-P2

The vector pJBF-5401 does not contain a convenient restriction sites between the Shine-Dalgarno sequence of the ribosomal binding site and the first ATG translation initiation codon. In order to use the deo P1-P2 promoters in an expression vector, it was therefore necessary to construct a restriction site and yet retain the same distance between the ribosomal binding site and the first ATG. This was accomplished by constructing an NdeI restriction site, consisting of the sequence CATATG which is cleaved CA/TATG. The gene to be cloned must have an NdeI site at the 5' end of the gene for insertion into the NdeI site of the plasmid; the ATG of the NdeI site is the initiation codon.

The new NdeI site in the deo P1-P2 vector was constructed by site—specific mutagenesis, Y. Morinaga et al., Biotechnology 2: 636–639 (1984) using BTG synthetic DNA fragment No. 2015, as described in FIG. 2. The four possible plasmids resulting from this procedure are shown in FIG. 2.

Bacteria containing plasmid A are eliminated because they are ampicillin sensitive. Bacteria containing plasmid B are eliminated because they will not hybridize to the nick-translated radiolabelled BssHII-SalHI fragment. Bacteria containing plasmids C and D are differentiated by hybridization to synthetic DNA fragment No. 2015 under increasingly stringent conditions and subsequently by the presence of the new Nde site introduced on the synthetic DNA fragments. Plasmid D, designated pMF5416, contains the deo P1-P2 promoters proximal to the new NdeI restriction site. However, sequence analysis (by the dideoxy method of Sanger) of 450 bp of the deo P1-P2 promoter sequence revealed that a 48 bp sequence extending from bp 702–749 of the deo P1-P2 promoter is not present. This sequence which is normally present in the deo P2 promoter region and is essential for transcription, was apparently deleted during the site-directed mutagenesis.

Construction of pMF-5531—A Plasmid Producing Low Levels of an hSOD Analog

The human copper/zinc superoxide dismutase (hSOD) coding sequence was then introduced into the vector containing deo P1-P2 promoter and subsequently the deletion in the P2 was repaired.

The plasmid pSODα13 (showing in FIG. 30 and constructed as described in the Description of the Figures) contains the gene encoding hSOD downstream from an Nde restriction site. Thus, it was possible to construct a new plasmid as shown in FIG. 3, which contains the hSOD gene downstream from the deo P1-P2 promoter (with the 48 bp deletion). This new plasmid has been designated pMF-5516.

In order to achieve expression, the deletion in the deo P2 region was now repaired as shown in FIG. 4 and described in the Description of the Figures. This produced a plasmid which contains, in 5' to 3' sequence, the complete deo P1-P2 promoter sequence (including the authentic ribosomal binding site), the NdeI restriction site and the hSOD gene.

This plasmid was transformed into *Escherichia coli* Sϕ744, a mutant lacking the cyt R and deo R repressors. K. Hammer-Jesperson and P. Nygaard, Molec. Gen. Genet. 148: 49–55 (1976). Following transformation, about 120 clones were screened for hSOD analog expression by electrophoresing on polyacrylamide gels extracts of cultures grown on LB medium. Several clones generated a very weak protein band which co-migrated with authentic purified hSOD. One clone was picked, and plasmid DNA was purified from it by density gradient centrifugation. The plasmid was designated pMF-5531. Plasmid pMF-5531 was introduced by transformation into *Escherichia coli* Sϕ540 and Sϕ732. Cultures were grown in LB medium (Example 13a) containing 0.2% glycerol overnight, and a cell mass equivalent to one $OD_{660}$ unit was processed (as described in Example 15) prior to application to SDS gels. These gels indicated that a low level of SOD analog equivalent to 1.5% of total *Escherichia coli* proteins was produced in *Escherichia coli* host Sϕ540. Slightly higher levels of hSOD were produced in Sϕ732. The hSOD analog produced in Sϕ540 reacted with $^{125}$I-labeled anti-human superoxide dismutase antibody. To eliminate the possibility that the low level of expression is associated with a sequence variation other than expected, a BglII-StuI fragment that includes the junction site of restriction and ligation was sequenced and found to be correct. This confirms that plasmid pMF-5531 contains the entire deo P1-P2 promoter region.

In a subsequent experiment, the site specific mutagenesis of plasmid pJBF5401 described above (and in FIGS. 2 and 3) was repeated and produced plasmid pMF-5416-2 (see FIG. 47). This plasmid was shown to contain the complete deo P1-P2 sequence without deletion.

Plasmid pMF-5513-1 was produced from this plasmid, as shown in FIG. 47. Plasmid pMF-5513-1 contains the hSOD analog coding sequence under the control of the deo P1-P2 promoter sequence, and as far as can be ascertained, this plasmid is identical to plasmid pMF-5531 (FIG. 4).

The protein produced by these plasmids and by plasmids which are described in the following sections is an analog of natural human copper/zinc superoxide dismutase. This analog is non-acetylated and non-glycosylated.

Modification of the deo Ribosomal Binding Site to Produce pMF-5519—A Plasmid With Good Production of an hSOD Analog Plasmid pMF-5531 displays low level expression of the hSOD gene. This could be a function of the distance between the ribosomal binding site and the first ATG of the message since variation in this distance is known to affect translation. The distance in pMF-5531 between the end of the ribosomal binding site and the first ATG is 4 nucleotides. This distance was extended to 6 nucleotides by cleaving pMF-5531 with NdeI, filling in with $T_4$ polymerase and re-ligating, thus producing a new plasmid with two extra base pairs.

This plasmid was used to transform *Escherichia coli* Sϕ744 (cyt R⁻deo R⁻) and several clones were analyzed by restriction endonuclease cleavage with NdeI to verify the elimination of the NdeI site by the fill-in polymerase reaction. Clones that contained plasmids lacking the NdeI site were grown, and the cell lysates were analyzed on SDS polyacrylamide gels. Several lysates revealed a protein band comigrating with an hSOD marker protein. The intensity of that band appeared several fold higher than that found in pMF-5531. The plasmid which appeared to be the highest expressor, designated pMF-5519, was purified and introduced into a variety of *Escherichia coli* hosts, in order to determine the most favorable host for expression. These *Escherichia coli* hosts included wild-type (ATCC Accession No. 12435), Sϕ928 (Δ deo), Sϕ929 (Δ deo, cyt R⁻) and Sϕ744 (deo R⁻, cyt R⁻). The last host enabled the highest level of expression. Subsequently, plasmid pMF-5519 was transformed into *Escherichia coli* Sϕ540, and densitometric analysis of protein profiles revealed that it produced more than twice as much hSOD analog as plasmid pMF-5531 in Sϕ540 (i.e., 3.5% of total protein). Plasmid pMF-5519 was also transformed into Sϕ732 and yielded higher levels of SOD analog than when it was in Sϕ540, namely 5.6% of total protein.

(The genotype of each *Escherichia coli* strain used and the source reference is detailed in Tables I and IA in Example 3).

The results of these experiments reveal that expression ranged from about 300–900 mg of hSOD per 50 O.D. units of bacterial culture. This evaluation was made on the basis of coelectrophoresis and staining of a standard 1 µg pure SOD together with bacterial samples followed by densitometer scanning (Enzyme levels produced by each strain are detailed in Table I in Example 3). The new sequence in the region of the filled-in NdeI site was confirmed by sequence analysis.

Further Extensions of Deo P1-P2 Ribosomal Binding Site

Since extension of the ribosomal binding site by two base pairs (in plasmid pMF-5519) produced a better producer of hSOD analog protein, a further series of four extensions of the deo P1-P2 ribosomal binding site were constructed in an attempt to further increase production. To achieve this end, eight single-stranded synthetic DNA sequences were synthesized as described in the legend to FIG. 6. Complementary strands were mixed to yield a final concentration of 100 pmole/ml and allowed to anneal for 26 hours at 7° C. producing 4 synthetic double stranded DNA linkers designated I, II, III and IV. Each double stranded DNA linker was ligated as shown in FIG. 6 to a 540 bp fragment from the deo P1-P2 operator/promoter region. This fragment had been prepared by cleaving plasmid pMF-5519 with StuI and BamI, purifying the resulting 1000 bp deo P1-P2 fragment from low melt agarose, and incubating the purified fragment with BglII and HinfI to produce a 540 bp BglII-HinfI fragment; this 540 bp fragment was isolated and purified from agarose gel. The resulting fragment was ligated into pMF-5531 as shown in FIG. 6, lengthening the distance between the deo P1-P2 sequence and the first ATG. (Plasmid pMF-5531 bears the unaltered P1-P2 ribosomal binding site sequence and is a low level producer of hSOD protein.) The plasmids produced in each case were used to transform Sϕ732 (cyt R⁻ deo R⁻). Clones were examined for expression of hSOD by growing in LB medium containing ampicillin followed by lysis and electrophoresis on SDS acrylamide gels. Clones which appeared to express hSOD at levels at least as high as pMF-5531 in Sϕ732 were picked, the plasmids were purified and the fragment containing the ribosomal binding site was analyzed by dideoxy sequencing.

At present, the sequence of plasmids containing two of the ribosomal binding site extensions have been verified. These correspond to linkers designated I and IV, i.e., 7–8 bp extension and 9–10 bp extension, respectively, and the plasmids have been designated pMF-558-26 and pMF-5536, respectively. It was found that they express low levels of hSOD analog protein similar to the levels expressed by pMF-5531.

Construction of pMF-5520—A High-Level Expressor of human copper/zinc superoxide dismutase (hSOD) Gene Previous observations in our laboratory have indicated that human copper/zinc superoxide dimsutase (hSOD) expression driven by the $P_L$ promoter system may be improved by replacing the ampicillin resistance gene on the plasmid with the tetracycline resistance gene. This approach was used to further elevate the expression of hSOD driven by the deo promoters. The ampicillin-resistance gene in pMF-5519 was replaced with the tetracycline-resistance gene as shown in FIG. 7. The plasmids produced were transformed into Sϕ540 (deleted for the deo operon) and plated on LB agar containing tetracycline. SDS gel electrophoresis of the tetracycline and ampicillin-resistant clones revealed increased levels of SOD expression from the tetracycline-resistant plasmid. This novel plasmid, which contains the tetracycline gene and expresses an hSOD analog under the control of the deo promoter gene, was designated pMF-5520.

The orientation of the tetracycline-resistance gene was confirmed by the following method. DNA prepared as described by H. C. Birnbaum and J. Doly, Nucl. Acid Res. 7: 1513 (1979) was digested with BamHI and electrophoresed to reveal approximately three fragments of approximately equal size 1400–1500 bp. This confirmed the clockwise orientation of the tetracycline resistance gene. (If the tetracycline-resistance gene was in a counterclockwise orientation, then one would expect one smaller BamHI fragment of about 700 bp; such a fragment was not produced.) Plasmid pMF-5520 was purified and introduced into a variety of *Escherichia coli* hosts to determine the most favorable host for expression. The hSOD expression levels of plasmid pMF-5520 in a wide variety of hosts are described in Example 3.

Construction of pMF-2005—A High Copy Number Plasmid Expressing the hSOD Gene In order to improve yet further the expression of hSOD gene under the control of the deo P1-P2 operator/promoter, it was decided to use a high copy number plasmid, pOP1Δ6, (approximately 7000 bp in length). This plasmid is a copy number mutant of pBGP120 which was derived from Col. E1, as described by D. H. Gelfand et al., PNAS 75: 5869–5873 (1978), M. H. Shepard et al., Cell 18: 267–275 (1979) and M. Muesing et al., Cell 24: 235–242 (1981). This mutant plasmid can comprise about 30% of total intracellular DNA. pOP1Δ6 was first treated as shown in FIG. 8 to replace the ampicillin resistance gene with a tetracycline-resistance gene, and the new tetracycline-resistance high copy number plasmid was designated pMF-2001. The deo P1-P2 operator/promoter region and the hSOD gene were inserted into this plasmid as shown in FIG. 9. The resulting plasmid (approximately 6400 bp in length) was first introduced to Sϕ540 by transformation and then plated on LB+Tet agar. Clones containing the high copy number mutant and the inserted fragment were identified by hybridization to nick-translated $^{32}$P labeled BamHI fragment isolated from pMF-5519. A plasmid purified by CsCl density gradient centrifugation designated pMF-2005 was introduced to a variety of *Escherichia coli* hosts, such as wild-type, Sϕ732, Sϕ540, Sϕ930, Sϕ928 (for genotype see above and also Table I) and was shown to direct a very high level of expression of hSOD protein under the control of the deo P1-P2 operator/promoter. The band intensities of the expressed hSOD protein in these hosts are quite similar, indicating that repressor function in hosts harboring active deo R and cyt R represors is no longer effective in limiting expression; densitometric analysis reveals that the hSOD analog produced represents about 35% of total cell protein. Plasmid pMF-2005 in *Escherichia coli* Sϕ732 has been deposited under ATCC Accession No. 67362.

Construction of Deo P1-P2 Vector with β-lactamase Ribosomal Binding Site

The deo expression vector pMF-5531 was made tetracycline resistant as shown in FIG. 17, producing pMFS-5533A. (As discussed above, this elevates the expression of hSOD driven by the deo promoters.) The synthetic β-lactamase ribosomal binding site from pSODβMAX-12 (deposited in the ATCC under Accession No. 67177) was inserted into pMFS-5533A as shown in FIG. 18. (The production of the plasmid pSODβMAX-12 is shown in FIGS. 13–16.) The resulting plasmid, designated pMFS-5538, contains in 5' to 3' order the deo P1-P2 operator/promoter region, the authentic deo RBS, the synthetic β-lactamase ribosomal binding site and the hSOD gene. Plasmid pMFS-5538 was introduced into the *Escherichia coli* host Sϕ732 and proved to be a moderate expressor of an hSOD analog protein (see Table I in Example 3).

Example 2

Optimal Growth Conditions for Expression of hSOD Analog Protein

Expression of certain bacterial gene products under deo P2-driven transcription is very low in the presence of glucose. This has been demonstrated both for the bacterial gene products of nucleotide catabolising enzymes of the deo operon (K. Hammer-Jesperson and A. Munch-Peterson, Mol. Gen. Genet. 137: 327–335 (1975)) and for the gene product *Escherichia coli* galactokinase (P. Valentin-Hansen et al., EMBO 1: 317–322 (1982)).

Experiments were performed to compare the effect of using succinate or glycerol as carbon source for the deo P1-P2 driven production human copper/zinc superoxide dismutase analog protein. Various strains of *Escherichia coli* hosts (wild-type, Sϕ744, Sϕ930, Sϕ928, Sϕ540) were employed (for the *Escherichia coli* phenotypes see Table I in Example 3). All of these strains were also tested when harboring plasmids pMF-5519 and pMF-5520. The wild-type *Escherichia coli* and Sϕ930 were also tested when harboring plasmid pMF-2005. All the *Escherichia coli* strains tested were grown in LB medium containing 150 ppm $Cu^{++}$, 10 ppm $Zn^{++}$ and either 0.2% succinate or 0.3% glycerol as carbon source (for standard techniques used, see Example 15).

It was found that when using glycerol as a carbon source the final pH of the medium was 5.8–6.0; when using succinate as a carbon source the final pH of the medium was 8.8–9.0. The expression of hSOD analog protein as measured by gel electrophoresis was much higher when glycerol was used; glycerol was thus used as carbon source in subsequent experiments.

In one example, prototroph *Escherichia coli* strain Sϕ732 harboring plasmid pMF 5520 grew well in minimal medium containing 75 ppm $Cu^{++}$, 5 ppm $Zn^{++}$ and 0.3% glycerol. The results are shown in Table I in Example 3.

The minimal medium used in all experiments where it is indicated is set forth below.

1 liter of Minimal medium contains:

$K_2HPO_4$—8 g $KH_2PO_4$—2 g $NH_4Cl$—3 g

Na citrate—2 g $MgSO_4.7H_2O$—400 mg

Fe citrate—40 mg 1.0 ml trace elements

The trace elements solution contains:

$MnSO_4.H_2O$—1 g $ZnSO_4.7H_2O$—2.78 g $COCl_2.6H_2O$—2 g $Na_2MoO_4.2H_2O$—2 g $CaCl_2.2H_2O$—3 g $CuSO_4.5H_2O$—1.85 g $H_3BO_3$—0.5 g

Concentrated HCl—100 mL

Deionized Water—900 mL

The effect of aeration on production of hSOD analog protein by various strains of *Escherichia coli* (Sϕ744, Sϕ928 and Sϕ540) harboring plasmid pMF-5520 was also examined. The expression of hSOD analog protein, as measured by gel electrophoresis, is clearly higher when there is low aeration. These laboratory results were scaled up (in the case of *Escherichia coli* Sϕ744 harboring pMF-5520) to 2 liter fermentors, (1 liter broth). Once again the hSOD expression was higher in low aeration conditions and these were used in all subsequent work.

Kinetics of the Constitutive Expression System

Since expression driven by the deo promoters is constitutive when the cells are grown on a non-glucose carbon source (as described above), it was of interest to determine if expression level is constant at any given time point of culture growth. To that end Sϕ732 containing pMF-5520 was seeded into minimal salt solution containing glycerol to $OD_{660}$ of 0.05 and grown at 37° C. At time intervals, samples of one $OD_{660}$ equivalent were removed and applied to SDS gel electrophoresis. The SOD protein band intensity increased as the culture reached late logarithmic growth phase and intensified further upon aging of culture (16–24 hr of culturing). Densitometric analysis reveals that hSOD represent 3–5% of total cell protein at log phase and accumulates through late log and stationary phase up to 15% of total cell protein.

A remarkable feature of the deo promoter driven expression is the relationship between hSOD expession and culture age. As described above, during logarithmic growth phase the relative intensity of the hSOD protein band on SDS polyacryamide gels is quite low. A progressive increase in hSOD expression level occurs from early stationary phase to late stationary phase and this expression peaks about 16–24 hr after seeding the cells. The observed increase in expression in stationary phase may be attributed to increase of plasmid copy number in the cell, or increase of transcription-translation of plasmid encoded genes as a consequence of reduced transcription-translation from chromosomes of resting cells. The dependence of hSOD expression on culture age was not observed when the host contained the high copy number plasmid pMF-2005; in this case the hSOD expression levels are similar in log phase growth and stationary phase. This is not surprising considering that a single cell contains about 400 plasmids (Shepard et al., Cell 18: 267–275 (1979)).

The data presented here shows clearly that it is possible to achieve high level constitutive expression with the deo promoters. The constitutive expression with deo promoter has several advantages in comparison to an inducible expression system. It alleviates the need for external manipulation such as temperature shift or media supplementation and allows better oxygen transfer due to lower culturing temperature. Moreover, the system facilitates growth and expression of cloned genes in continuous culture. Other host vector systems which express hSOD analog constitutively are described in Example 19.

While not wishing to be bound by theory, it is possible that the deo constitutive system for producing hSOD analog is successful because human superoxide dismutase is a soluble protein. When insoluble protein, e.g., growth hormone, are produced under the control of deo P1-P2 promoters, it is preferable to first achieve the desired biomass by growth on glucose and to then switch over to a non-glucose carbon source for chemical induction (see Examples 16 and 17).

Example 3

Enzymatic Activity of the hSOD Analog Protein Produced

Three deo P1-P2 vectors expressing hSOD analog protein (pMF-5519, pMF-5520 and pMF-2005) were introduced to a variety of *Escherichia coli* hosts and the enzymatic activity of the hSOD analog in crude cell extracts was measured by monitoring the inhibition of reduction of ferricytochrome-C as described by McCord and Fridovich, J. Biol. Chem. 244: 6049–6055 (1969).

The results are shown in Table I. These experiments indicate that the tetracycline-resistant plasmid pMF-5520 produces a somewhat higher level of hSOD analog enzyme than does the ampicillin-resistant plasmid pMF-5519. Table I also clearly demonstrates that the high copy number deo P1-P2 containing plasmid pMF-2005 produces about twice as much hSOD analog enzyme as the other deo P1-P2 vectors.

As also clearly demonstrated in Table I, plasmids producing hSOD analog under the control of a deo P1-P2 promoter are equal to or superior to $pSOD\beta_1T11$, a plasmid producing hSOD under the control of a $\lambda\ P_L$ promoter. Plasmid $pSOD\beta_1T11$ has been deposited with the American Type Culture Collection in Rockville, Md. 20852, U.S.A. under ATCC Accession No. 53468 pursuant to the Budapest Treaty. The plasmid has the restriction map shown in FIG. 13.

TABLE I

| | | SOD Activity in Crude Cell Extracts | | | |
|---|---|---|---|---|---|
| Strain* | Resident Plasmid | % hSOD of Total Protein | Fold Increase in hSOD Protein | hSOD S.A. | Fold increase of hSOD S.A. |
| Sϕ540 | pMF 5519 | 3.5 | | 204 | 1.37 |
| Sϕ540 | pMF 5520 | 6.5 | 1.85 | 281 | |
| Sϕ930 | PMF 5519 | 5.4 | | 254 | |
| Sϕ930 | pMF 5520 | 13.0 | 2.4 | 381 | 1.50 |
| Sϕ732 | pMF 5519 | 5.6 | | 201 | |
| Sϕ732 | pMF 5520 | 14.0 | 2.5 | 397 | 1.97 |
| Sϕ732 | pMF 5538 | | | 110 | |
| ATCC 12435 | pMF 5519 | 6.2 | | 140 | |
| ATCC 12435 | pMF 5520 | 6.3 | 1.05 | 194 | 1.38 |
| ATCC 12435 | pMF 2005 | 35 | 5.6 | 700 | 5.00 |
| Sϕ928 | pMF 5520 | | | 263 | |
| Sϕ929 | pMF 5520 | | | 282 | |
| Sϕ744 | pMF 5520 | | | 397 | |
| A4255 | $pSOD\beta_1T_{11}$ | | | 113–188 | |

*Note: For genotype and source of each bacterial strain, see Table IA.

TABLE IA

Bacterial Strains of *Escherichia coli*[1]

| | |
|---|---|
| * | Sϕ540 - thi, leu, Δdeo11, rspL (λ cI 857 Sam7 :: deo). |
| ** | Sϕ928 - thi, ton, upp, udp, lac, Δdeo11. |
| ** | Sϕ929 - thi, ton, upp, udp, lac, cyt R-15, Δdeo11. |
| ** | Sϕ930 - thi, ton, upp, udp, lac, Δdeo, deo R-7, clm A. |
| *** | Sϕ732 - deo R-1, cyt R-4, str A. |
| **** | Sϕ744 - met, ile, cyt R, deo R. |
| | ATCC 12435 - wild-type. |
| | A 4255 - biotin-dependent wild-type. |

* *Escherichia coli* strain Sϕ540 is described by R. S. Buxton, K. Hammer-Jesperson and T. D. Hansen, J. Bacteriol. 136: 668–681 (1978).
** *Escherichia coli* strains Sϕ928, Sϕ929, and Sϕ930 are described by Valentin-Hansen et al., Molec. Gen. Genet. 159: 91–202 (1978).
*** *Escherichia coli* strain Sϕ732 is described by K. Hammer-Jesperson and A. Munch-Peterson, Molec. Gen. Genet. 137: 327–355 (1975); it is a prototropic strain.
**** *Escherichia coli* strain Sϕ744 is described by K. Hammer-Jesperson and P. Hygaard, Molec. Gen. Genet. 148: 49–55 (1976).
[1]Note that F⁻ strains used are described in Example 21.

Example 4

Construction of deo P1-P2 Vector Expressing MnSOD-GPX Fused Protein

Plasmid pE4GPX (see FIG. 10) was constructed as shown in FIG. 28 and as described in coassigned copending U.S. Ser. No. 085,647. Plasmid pE4GPX was constructed from plasmids pMSE4 (ATCC Accession No. 53250), which contains the complete cDNA sequence encoding human MnSOD and from plasmid p18UL-1 (ATCC Accession No. 67361) which contains the complete cDNA sequence encoding glutathione peroxidase (hGPX). Plasmid pE4GPX is a fusion plasmid which contains the entire coding sequence of hGPX ligated to the 3' end of the truncated hMnSOD gene. It expresses a fused protein under the control of the $\lambda P_L$ and the cII ribosomal binding site. The fused protein produced is about 190 amino acids long; the N-terminal sequence is the first 152 amino acids of hMnSOD. The total length of about 190 amino acids possibly indicates that translation termination occurred within the coding sequence of hGPX.

As shown in FIG. 10, the $\lambda P_L$ promoter-operator was removed from plasmid pE4GPX, and the 1.3 kb fragment from pMF-5531 containing the deo P1-P2 sequence was inserted in its place. This novel plasmid, pDGE4-3 contains in 5' to 3' order the deo P1-P2, the cII RBS and the MnSOD-GPX sequences. This plasmid was transformed into *Escherichia coli* MC1061 (M. Casadaban and S. N. Cohen, J. Mol. Biol. 138: 179–207 (1988)) and the resulting clones were assayed for production of MnSOD-35 GPX fused protein. The cells were grown in LB medium+ampicillin; LB medium is described in Example 13. Cells which contained plasmid pDGE4-3 expressed large quantities of an hMnSOD-hGPX fused protein which comigrated with the fused protein (about 190 amino acids long) produced under the control of the $\lambda P_L$ promoter and cII RBS in plasmid pE4GPX. Western blot analysis using anti MnSOD antibodies demonstrated that small amounts of a full size fusion protein were produced, implying read-through of the TGA "stop" codon within the coding sequence of hGPX.

Thus the deo P1-P2 operator/promoter region together with the cII ribosomal binding site can direct the synthesis of large quantities of a fused MnSOD-GPX protein.

Plasmid pDGE4-3 was also transferred into *Escherichia coli* strain Sɸ732 (cyt R⁻, deo R⁻) and very similar levels of expression were obtained.

Example 5

Construction of deo P1-P2 Vector Expressing human growth hormone (hGH) Protein Plasmid pTVR 568-4 was constructed as shown in FIG. 11 by removing the entire hMnSOD and part of the hGPX coding sequences from plasmid pDGE4-3 and replacing them with the human growth hormone (hGH) coding sequence from plasmid pTV 104(2) (ATCC Accession No. 39384). This new plasmid, pTVR 568-4, contains in 5' to 3' order the deo P1-P2, the cII RBS and the entire hGH sequence. It was transformed into *Escherichia coli* MC1061 and colonies expressing hGH analog were selected by hybridizing polyclonal anti-hGH antibodies to colonies lysed and immobilized on filters. Following overnight growth in LB broth containing ampicillin (as described in Example 13), the culture was lysed and electrophoresed on SDS polyacrylamide gels.

It was found that pTVR 568-4 directs production of hGH at levels estimated to be 20–25% of the total bacterial protein. Direct comparisons on polyacrylamide gels of proteins from cells containing this construction (pTVR 568-4) and from cells containing hGH under the control of the $\lambda P_L$ promoter (pTV 104-2) indicate that 50–100% more hGH is produced by the deo promoter compared to the $\lambda$ promoter.

Example 6

Construction of deo P1-P2 Vector Expressing Bovine Growth Hormone (bGH) Analog Plasmid pMFS-5600 was constructed as shown in FIG. 12 by removing the MnSOD and part of the hGPX coding sequences from the deo P1-P2 expression vector pDGE4-3 and replacing them with the 750 bp bGH sequence from pSAL 440-11. Plasmid pSAL 440-11 is produced as described in the description to FIG. 12.

The ligated plasmid was transformed into *Escherichia coli* strain Sɸ732 (cyt R⁻ deo R⁻) (for details of this strain see Table I in Example 3). Clones expressing the met-asp-gln-bGH analog were picked and grown in buffered LB media containing succinate as carbon source and ampicillin. The clone designated pMFS-5600 was used for isolation of plasmid and further experimentation.

Plasmid pMFS-5600 contains in 5' to 3' order the deo P1-P2, the authentic deo RBS, the cII RBS, the entire bGH coding sequence followed by part of the hGPX coding sequence and the human copper/zinc superoxide dismutase coding sequence. Plasmid pMFS-5600 expresses bGH protein at a high level. The GPX and human copper/zinc superoxide dismutase sequences are not translated because of the translation termination signal at the 3' end of the bGH gene.

Example 7

Construction of deo P1-P2 Vectors Expressing Apolipo-protein E (ApoE) Fused Protein Plasmid pTVR 580-35 was constructed as shown in FIG. 19 by replacing the hGH coding sequence in plasmid pTVR 568-4 with the hGH-ApoE fused sequence from plasmid pSAL 160-5; the sequence comprises the first 45 amino acids of hGH fused to amino acids 12–299 of apolipoprotein E3. Plasmid pSAL-160-5 is shown in FIG. 34 and constructed as described in the Description of the Figures (FIGS. 31–34).

The resulting ligated plasmid was transformed into *Escherichia coli* strain A1645. Plasmid pTVR 580-35 in *Escherichia coli* strain A1645 was grown in LB fortified (LBF) medium. (1 liter of LBF medium contains 20 g tryptone, 10 g yeast extract, 5 g NaCl, 0.3M MgSO$_4$ and 0.1M K$_2$HPO$_4$). Clones expressing a gene product of the expected size were picked out and the clone designated pTVR 580-35 was isolated.

Plasmid pTVR 580-35 contains in 5' to 3' order the deo P1-P2, the authentic deo RBS, the cII RBS and the hGH-ApoE fused coding sequence. It expresses fused hGH-ApoE at high levels. The plasmid was retransfected to prototrophic strain *Escherichia coli* MC1061 and the resulting clone was designated 580-35-1.

Example 8

Construction of deo P1 Vector Expressing the λ cI 857 Repressor Protein

The λ cI 857 gene was cloned as follows: λ DNA harboring the temperature sensitive cI 857 was purchased from New England Biolabs. The DNA was cleaved with EcoRI and BamHI restriction enzymes and mixed with pBR322 restricted with the same enzymes. The mixture was ligated and transformed into Sϕ540. Colonies obtained on LB agar containing ampicillin were isolated, grown on LB agar and assayed for immunity to λ C60 infection. Colonies which upon spreading onto agar plates yielded lysed area due to λ C60 infection were disregarded while those which show no lysis were further analyzed. The clones which repeatedly show immunity to infection with λ C60 contained a plasmid with a 5400 bp insertion which contained the cI 857, Rex A, Rex B, and N gene sequences. This plasmid was designated pMF-31.

Attempts to produce cloning vectors harboring both the cI 857 repressor sequence controlled by its authentic λ Prm promoter and also a eucaryotic gene to be expressed under the λ $P_L$ were unsuccessful; the cells grow poorly and produced very low amounts of the desired eucaryotic protein. We believe that in such clones the cI 857 repressor is overproduced and is detrimental to vigorous cell growth. To permit a low level of cI 857 repressor to be synthesized continuously, it was decided to utilize the weak deo P1 promoter.

The construction of plasmid pMF 54DC is shown in FIGS. 21–23 and detailed in the description to these FIGS. These constructions show the replacement of the authentic Prm promoter of λ cI 857 in plasmid pMFL 31 with the deo P1 promoter and a synthetic linker containing the Shine-Dalgarno sequence of the cII ribosomal binding site proximal to the first ATG of the coding sequence of the repressor. (Also the Rex A and Rex B genes were eliminated from pMFL 31.) The final plasmid designated pMF 54DC, (FIG. 23) was used to transform *Escherichia coli* MC1061. (M. Casadaban and S. Cohen, J. Mol. Biol. 138: 179–207 (1980).

Thirty (30) transformants of *Escherichia coli* MC1061 transformed with pMF 54DC were picked at random and subjected to infection with λ C60. Clones showing immunity to infection by λ C60 did not lyse. The immunity proves the presence of functional cI repressor in the cell and thus provides evidence that the deo P1 promoter is functional. To verify the presence of deo P1 and cI repressor, plasmids from several clones were isolated and analyzed for the presence of the expected endonuclease recognition sites. The plasmid harboring all expected restriction sites was designated pMF 54DC. It directs expression of the λ cI 857 repressor protein under the control of the deo P1 operator/promoter, as demonstrated by resistance to infection by C60; however, the cI 857 protein product is not detectable on polyacrylamide gels stained with Coomassie blue.

Example 9

Construction of an Independent bGH Expression Vector Containing the λ cI 857 Repressor Gene Under the Control of deo P1

The following novel construct includes the λ cI 857 repressor gene on the same plasmid as the bGH gene expressed under the control of the λ cI 857 regulated λ $P_L$ promoter. This allows the plasmid to be introduced to prototrophic bacteria without first introducing the λ cI 857 gene into the host cell chromosome. The fragment containing the λ cI 857 repressor under the control of the deo P1 operator/promoter region was isolated from pMF 54DC as described in FIG. 24. This fragment (approximately 1300 bp long) was ligated to the linear form of pSAL 440-22 (obtained as described in FIG. 24) which contains the gene for bGH under the control of the λ $P_L$ promoter and a modified (N-protein independent) cII ribosomal binding site (see FIG. 24). The ligation was performed as follows: pSAL 440-22 cleaved with ClaI and filled in using the Klenow-DNA Polymerase and the isolated 1300 bp fragments were mixed in a 1:2 ratio respectively and the mixture ligated with $T_4$ ligase. The ligated mixture was used to transform a prototroph *Escherichia coli* (ATCC Accession No. 12435). Several transformants were picked and tested for immunity upon infection with λ C60 at 30° C. and 42° C. Those clones which were immune at 30° C. (no lysis) while sensitive at 42° C. (lysed) were further analyzed to determine the orientation of the inserted fragment by means of restriction enzyme mapping.

To verify the proper function of all elements on the newly constructed plasmid, ATCC Accession No. 12435 transformed clones were grown in liquid media at 30° C. for 6 hours in 3 ml cultures. The cultures were split into two halves; one was heat treated at 42° C. for 2 hours and the other was incubated for the same length of time at 30° C. Protein was extracted from these two cultures and subjected to SDS gel electrophoresis. Following staining and removal of unbound stain it became clear that cultures treated at 42° C. produced a protein which upon electrophoresis migrates identically to reference bGH. This protein band reacted with anti-bGH antibodiy. No such band was observed in the control uninduced culture extracts. The new composite plasmid was designated pFSAL-A5, or pFSAL-B27 depending on the orientation of the inserted cI repressor (as described in the legend to FIG. 24).

Sequence analysis subsequently demonstrated that a partial deo P1 promoter sequence truncated at the 5' end is present in plasmid pFSAL-B27, whereas the complete deo P1 promoter sequence is present in pFSAL-A5. The missing sequence in the truncated deo P1 is believed to consist of the region from the start of deo P1 to the AccI site at position 147–152 (see FIG. 2 in P. Valentin-Hansen et al., The EMBO Journal 1: 317–322 (1982)). Thus, the truncated deo P1 consists of about 72 nucleotides only, from the AccI site to the end of the BglII site at position 222, and no longer contains the EcoRI restriction site at position 104–109. Dandanell and Hammer in The EMBO Journal 4: 3333–3338 (1985) disclose that "filling out the EcoRI site in deo P1 . . . destroyed the operator activity". Surprisingly, truncated deo P1 without the known operator-promoter region in the EcoRI site controls production of the cI 857 repressor.

Note that the fragment containing the deo P1 promoter (or part of it) and the λ cI 857 repressor sequence can be removed from pFSAL-A5 by SspI and XmnI digestion and from pFSAL-B27 by SspI digestion alone (see FIGS. 24 and 25). This fragment can then be inserted into any expression vector, where the gene product is expressed under the λ promoter, to make that vector an independent thermolabile expressor of gene product. Plasmid pFSAL-B27 has been deposited as pFSAL-130-B27 in *Escherichia coli* 12435 as ATCC Accession No. 67071. It produces about 0.1 g bGH analog per gram of dry cell weight after 3–4 hours heat-induction.

The truncated deo P1 sequence in pFSAL-B27 can be converted to the full length sequence by the following route.

Digest plasmid pMF 5534 (ATCC Accession No. 67703 deposited on May 23, 1988) with BglII and AatII (the AatII site is located in the ampicillin-resistance gene), isolate the small fragment and ligate it to the large fragment obtained by digestion of pFSAL-B27 with BglII and AatII. The resulting plasmid contains the full-length deo P1 sequence, and can be cut by SspI to remove the fragment containing the deo P1 promoter and the λ cI repressor sequence as described in the paragraph above.

Example 10

Construction of an Independent Human copper/Zinc Superoxide Dismutase (hSOD) Expression Vector Containing the λ cI 857 Repressor Gene Under the Control of deo P1

Plasmid pFSAL-A5 was cleaved to remove the small fragment containing the λ cI 857 under the control of the deo P1 promoter, and this was ligated to the filled in AvaI site of plasmid pSODβMAX-12 (as shown in FIG. 25). Plasmid pSODβMAX-12 (ATCC Accession No. 67177) is a high-level hSOD expressor which contains in 5' to 3' order the λ $P_L$ promoter, the β-lactamase promoter, a synthetic β-lactamase ribosomal binding site (sII) and the human copper/zinc superoxide dismutase sequence. Ligation of the deo P1+cI 857 sequence into this plasmid gives the resulting high expression plasmid the ability to be transformed into a wide range of Escherichia coli cells, including prototrophic cells, since it is independent of cI repressor produced by the host chromosome. The resulting plasmids from this ligation were used to transform Escherichia coli strain MC1061. Retransformation into the prototroph Escherichia coli strain ATCC Accession No. 12435 was performed and plasmids carrying the deo P1+cI in both orientations were characterized. One isolate designated pSODβMAX-12-cI gave good expression levels of hSOD. The transformed bacteria grew well at 42° C. and expressed hSOD analog protein for at least 6 hours.

Example 11

Construction of Independent ApoE Analog Expression Vectors Containing the λ cI 857 Repressor Gene Under the Control of the deo P1 Promoter (a) Independent Vector Expressing Met ApoE (pTVR-590-4)

The fragment containing deo P1 controlling the cI 857 repressor gene from plasmid pFSAL-A5 was ligated as shown in FIG. 27 into plasmid pTV 194-80, which expresses the ApoE analog met-ApoE. (The construction of plasmid pTV 194-80 is described in Example 4 and FIG. 22 of coassigned copending patent application Ser. No. 644,671 of Oppenheim et al. and in EPO Publication No. 173,280, where it is designated pTV 194.) The plasmid designated pTVR 583-17 was produced and introduced into Escherichia coli MC1061, and subsequently retransformed into Escherichia coli ATCC Accession No. 12435, a prototroph wild-type strain. Clones were screened for immunity to infection by λ C60. Clones which possessed functional cI 857 re-pressor were analyzed by restriction endonuclease mapping and one clone designated pTVR-590-4 was used in further experimentation. This plasmid proved to be a thermolabile expressor of met-ApoE, thereby demonstrating the production of functional thermolabile cI 857 repressor by the plasmid. Plasmid pTVR 590-4 has been deposited with the American Type Culture Collection in Rockville, Md., U.S.A. under ATCC Accession No. 67360 on Mar. 20, 1987.

(b) Independent Vector Expressing Met-Leu-Leu-Met-ApoE (pTVR 700-2)

The fragment containing deo P1 controlling the cI 857 repressor gene from plasmid pFSAL-A5 was inserted as shown in FIG. 26 into plasmid pTVR 289-18, which expresses the apolipoprotein E (ApoE) analog met-leu-leu-leu-met-ApoE, under the control of the λ $P_L$ promoter and the β-lactamase ribosomal binding site. (Plasmid pTVR 289-18 is constructed as shown in FIG. 29 from plasmid pTVR 279-8 which expresses met-leu-leu-leu-met-ApoE under the control of the λ $P_L$ promoter and the cII ribosomal binding site; the production of plasmid pTVR 279-8 (ATCC Accession No. 53216) is described in EPO Publication No. 173,280. The effect of this is to make the resulting plasmid designated pTVR 700-2 independent of the expression of thermolabile repressor on the host chromosome. This plasmid pTVR 700-2 can be transformed into a wide variety of cells. (Plasmid pTVR 700-2 was first introduced into Escherichia coli MC1061 where it was designated pTVR 596-1 and subsequently transfected into wild-type Escherichia coli 12435 where it was designated pTVR 700-2). The expression of of ApoE analog by pTVR 700-2 is even higher than the expression of ApoE analog by pTVR 590-4 (described above).

(c) Further Construction of Independent ApoE Analog Expression Vectors

Further constructions of independent ApoE analog expression vectors have been made in which the ApoE analog is expressed under control of the cII RBS instead of the β-lactamase RBS, in order to avoid the possibility of "leaky" expression by the β-lactamase promoter RBS and production of ApoE before thermal induction. In one such construction the deo P1-cI fragment produced from pFSAL-A5 by XmnI/SspI digestion was inserted into plasmid pTVR 279-8 (see FIG. 29). Plasmid pTVR 279-8 produces met-leu-leu-leu-met-ApoE under the control of the λ $P_L$ and the cII ribosomal binding site (see FIG. 29); it was opened with ClaI, filled-in with Klenow DNA polymerase and the deo P1-cI 857 fragment was inserted. This produced plasmid pTVR 714 which was introduced to Escherichia coli 1061; this independent plasmid has the coding sequence for met-leu-leu-leu-met-ApoE under the control of the λ $P_L$ and the cII ribosomal binding site, and also contains the deo P1 controlling the λ cI 857 repressor protein. Plasmid pTVR 714 was subsequently transferred to Escherichia coli 12435 and designated pTVR 721-4.

Example 12

Construction of Independent Porcine Growth Hormone (pGH) Expression Plasmids Containing the λ cI 857 Repressor Gene Under the Con-trol of the deo P1 Promoter (a) Plasmid pEFF-902
(i) Construction of Plasmid pEFF-902

The starting point for the porcine growth hormone (pGH) expression plasmids which are described in this application is plasmid pRec-pig24. This plasmid, shown in FIG. 36 and described in copending, coassigned U.S. application Ser. No. 821,830, has been deposited with the ATCC under Accession No. 53433. Plasmid pRec-pig24 thermoinducibly expresses a pGH analog under the control of the λ promoter $P_L$ and the thermolabile repressor cI 857 (which resides on the chromosome); the pGH analog has as N-terminal sequence met-asp-gln attached to the phenylalanyl residue which is the first amino acid of authentic pGH. In the above mentioned U.S. application plasmid pRec-pig24 was described as being an especially preferred expressor of pGH analog protein.

In order to construct an independent pGH expressing plasmid, the DNA encoding the pGH analog was removed from pRec-pig 24 and inserted into the independent bGH expression plasmid pFSAL-130-B27 from which the bGH analog coding sequence had been excised (FIG. 36). This produced plasmid pEFF-902.

(ii) Bench-scale growth and expression of *E.coli* strain ATCC No. 12435 containing plasmid pEFF-902

Plasmid pEFF-902 was introduced into *Escherichia coli* ATCC Accession No. 12435 (a prototroph wild-type strain) and grown in minimal medium (see Example 2) containing 0.2% glucose in a total volume of 25–30 ml at 30° C. When the $OD_{660}$ reached 0.9–1.0 the temperature was elevated to 42° C. and the flask was shaken for 4–6 hours; prior to the temperature shift methionine was added to a final concentration of 100 mg/liter. At 1 hour time intervals 1.00D unit samples were removed and analyzed by SDS polyacrylamide gel electrophoresis. The Coomassie blue stained gels revealed that the pGH analog protein is progressively accumulated up to 4 hours after the beginning of induction, and is maintained at this level for at least 6 hours after the beginning of induction.

Pulse-labeled and pulse-chase experiments with $^{35}$S-methionine confirmed that de novo synthesis of the pGH analog protein proceeds as long as 6 hours after the beginning of induction and that the pGH analog produced is very stable.

Western blots of the protein products from pEFF-902 and pRec-pig24 cultures grown simultaneously, which were treated with $^{125}$I-labeled anti-pGH antibody, revealed that the pGH analog produced by the two plasmids comigrated. Based on $^{125}$I signal intensity we concluded that pEFF-902 produced far more pGH analog than pRec-pig24.

(iii) Batch fermentation of E.coli strain ATCC Accession No. 12435 containing plasmid pEFF-902

*Escherichia coli* ATCC Accession No. 12435 containing plasmid pEFF-902 was grown in 1 liter minimal medium (Example 2) in a 2 liter vessel at 30°, under conditions of glucose feeding and pH control by 15% $NH_4OH$. Samples were removed at 1 hour intervals for 5 hours and 1.0 $OD_{660}$ unit samples were run on SDS polyacylamide gels. Densitometric analysis of the Coomassie blue stained bands revealed that 4 hours after beginning the induction pGH analog accounts for 23–25% of the total protein. In addition, total dry cell weight was measured and also the amount of pGH protein produced in the same fermentation was determined by comparison to known amounts run in parallel on the same gel; this gives the specific productivity (gram protein product per gram dry cell weight) which in three different determinations ranged between 0.12 and 0.15.

Table II shows a comparison of the expression levels of plasmids pEFF-902 and pRec-pig24 based on both the bench-scale experiments and the batch fermentations.

(b) Plasmids pEFF-9021 and pEFF-9022

We have previously found that SOD expression driven by the $\lambda\,P_L$ promoter system may be improved by replacing the ampicillin resistance gene on the plasmid by the tetracycline resistance gene. This approach was used in an attempt to further elevate the expression of the pGH analog expressed under the control of the $\lambda\,P_L$ promoter in the thermoinducible independent plasmid. We therefore replaced the ampicillin resistance gene in plasmid pEFF-902 with a tetracycline gene from plasmid pBR322, as shown in FIG. 37. The products of this ligation were transformed into *Escherichia coli* strain ATCC Accession No. 12435; two constructs possessing tetracycline resistance were produced, pEFF-9021 and pEFF-9022. They are both independent plasmids which express pGH analog under the control of the $\lambda\,P_L$ promoter, thermoinducibly controlled by the cI 857 repressor; the plasmids differ only in the orientation of the tetracycline resistance gene (FIG. 37).

Induction experiments in minimal medium (Example 2) revealed that both tetracycline resistant plasmids express the pGH analog at high levels. Comparison of the expression levels of various pGH analog-expressing plasmids is shown in Table II.

It is clear from the above results that the independent thermoinducible plasmids pEFF-902, pEFF-9021 and pEFF-9022 express pGH analog at a much higher level than plasmid pRec-pig24. The construction of another independent plasmid expressing pGH analog is described in Example 20.

TABLE II

Hosts and Expression Plasmids of pGH and bGH Analogs

| Host* | Plasmid | Antibiotic Resistance | Promoters | Rbs | Cloned Gene & Relative Expression*** |
|---|---|---|---|---|---|
| A4255 | pRec-pig24 | AMP | $\lambda\,P_L$ | cII | pGH+ |
| ATCC 12435 | pEFF-902 | AMP | $\lambda\,P_L$, deo P1 | cII | pGH+++ |
| ATCC 12435 | pEFF-9021 | TET | $\lambda\,P_L$, deo P1 | cII | pGH+++ |
| ATCC 12435 | pEFF-9022 | TET | $\lambda\,P_L$, deo P1 | cII | pGH+++ |
| Sϕ732 | pEFF-905 | AMP | deo P1–P2 | deo, cII | pGH++++ |
| Sϕ732 | pEFF-920** | AMP | deo P1–P2 | deo, cII | pGH++++ |
| Sϕ732 | pMFS-5603 | AMP | deo P1–P2 | deo, cII | bGH+ |
| Sϕ732 | pMFS-5605** | AMP | deo P1–P2 | deo, cII | bGH+++ |

*The *E. coli* hosts are described in Table I.
**PAR+.
***Expression levels are expressed on a relative range between low level expressors (+) and high level expressors (++++).
NOTE: See also Tables III and IV in Examples 18 and 19, respectively.

Example 13

Construction of deo P1-P2 Vectors Expressing Porcine Growth Hormone (pGH) Analog Protein The following paragraphs detail the construction of a series of deo P1-P2 expression plasmids directing the production of the pGH analog.

(a) Plasmid pEFF-905

As shown in FIG. 38, the fragment containing in 5' to 3' order the cII ribosomal binding site, the pGH sequence and the $T_1T_2$ terminator sequence was removed from plasmid pEFF-902 and inserted into plasmid pMF 5531 from which the hSOD sequence had been partially removed. (Plasmid pMF 5531 expresses hSOD analog protein under the control of the deo P1-P2 promoter—see FIG. 4).

The resulting plasmid pEFF-905 was transformed into *Escherichia coli* S$\phi$732 (described in Table I). Plasmid pEFF-905 expresses the pGH analog protein under the control of the deo P1-P2 promoter and cII ribosomal binding site. The level of the pGH analog produced is very high and exceeds the level produced by the $\lambda P_L$ expression vector, pRec-pig24, and that produced by the $\lambda P_L$ independent expression vectors pEFF-902, pEFF-9021 and pEFF-9022 (see Example 12). A comparison of the expression levels of pGH analog protein directed by these plasmids is shown in Table II (Example 12).

However, the expression of cells harboring plasmids pEFF-905 decreased dramatically after several transfers indicating that this construct is unstable. Growth of *Escherichia coli* S$\phi$732 cells harboring pEFF-905 in rich medium (LB+0.3% glycerol+ampicillin) shows a progressive decrease in production of pGH analog after only 15 generations. (1 liter of LB medium contains 10 g Tryptone, 5 g Yeast Extract, 10 g NaCl and pH adjusted to 7.5 with NaOH; as described by T. Maniatis, E. F. Fritsch and J. Sombrook, in *Molecular Cloning: A Laboratory Manual*, Cold Spring Harbor Laboratory, New York (1982)). This instability may possibly be due to improper partitioning, improper replication or other reasons, all caused by the very high expression levels.

(b) Plasmid pEFF-920
(i) Construction of plasmid pEFF-920

In order to increase plasmid stability, a 350 bp fragment containing the PAR (partition) sequence from plasmid pSC101 was introduced into pEFF-905, as shown in FIG. 39. (Plasmid pSC101 is available from the ATCC under Accession No. 37032 and it has been described by S. Cohen in J. Bact. 132: 734–737 (1977) and in J. Bact. 134: 1141–1156 (1978)). The resulting plasmid, designated pEFF-920, produces the pGH analog protein under the control of the deo P1-P2 promoter and cII ribosomal binding site and additionally includes the PAR sequence. Plasmid pEFF 920 has been deposited in *Escherichia coli* strain S$\phi$930 in the ATCC under Accession No. 67706.

(ii) Growth and Expression of *Escherichia coli* S$\phi$732 harboring plasmid pEFF-920

Plasmid pEFF-920 was introduced to *Escherichia coli* S$\phi$732 (described in Table I) and grown in separate experiments in rich medium (LB+0.3% glycerol+ampicillin) and in minimal medium (MM+ampicillin+0.2% glucose). The composition of LB medium is as described in (a) above; the composition of minimal medium (MM) is given in Example 2. Plasmid stability and expression levels were monitored. In rich medium the plasmids were stably maintained for about 60 generations after which there was a sharp drop in expression; this is a great improvement on the expression of plasmid pEFF-905 which shows a drop in expression levels after only 15 generations (see (a) above).

In minimal medium (to which glucose is added) the plasmids were maintained for more than 80 generations although yielding low expression levels. However, when glucose was depleted and glycerol was added as carbon source pGH accumulated in the cells and could be observed under the microscope as large refractive bodies. These observations suggest that the PAR sequence on the plasmid increases the probability of proper replication of the entire plasmid. The low level of deo P1-P2 driven expression described above in the presence of glucose is probably due to the "glucose effect" described in the "Background of the Invention". When glucose is present, expression of the gene product driven by the deo P2 promoter is very low; since the deo P1 promoter is weak, there is little gene product produced by the deo P1-P2 promoters in the presence of glucose. However, in the presence of glycerol as an energy source expression from the deo P2 promoter is high (see Example 2). Thus, when glucose became depleted and we added glycerol as energy source, deo P1-P2 driven transcription levels became elevated and large amounts of the pGH analog were produced.

(iii) Batch fermentation of *E. coli* strain S$\phi$732 harboring plasmid pEFF-920

Batch fermentation of strain S$\phi$732/pEFF-920 was performed in 2 liter fermentors at 37° C. in minimal medium solution (see Example 2) and 1% glucose. Under these conditions the doubling time is 60 minutes. When the glucose was exhausted, the culture was grown with glycerol to permit deo P1-P2 driven transcription of pGH analog to take place (see (ii) above). Glycerol fermentation was allowed to proceed for 4–8 hours. The $OD_{660}$ at time of harvest ranged from 30–80 OD units/ml depending on the amount of glucose added at the start of growth. SDS-PAGE electrophoresis of samples at point of harvest indicated that the expression of the pGH analog exceeded the level observed with other $\lambda P_L$ expression systems (see Table II in Example 12) and that the amount of pGH analog produced was greater than 25% of total cell protein. For further studies on the optimization of expression of pGH analog protein from these vectors, see Example 16.

Example 14

Further deo P1-P2 Plasmids Expressing Bovine Growth Hormone (bGH) Analog

The following paragraphs detail the construction of plasmids expressing a bGH analog under the control of the deo P1-P2 promoters. These plasmids differ from that described in Example 6 (pMFS-5600) primarily by the presence of the $T_1T_2$ transcription termination sequences. We expected this to increase the stability of the plasmids; plasmid pMFS-5600 appeared to be unstable under usual growth conditions.

(a) Construction of plasmids expressing bGH analog
(i) Plasmid pMFS-5627

The 1750 bp fragment from pFSAL-130-B27 (ATCC Accession No. 67071) containing the bGH and $T_1T_2$ sequences was removed and inserted into the deo P1-P2 containing plasmid pMF-558-26 (see FIG. 6). The resulting plasmid pMFS-5627, shown in FIG. 40 was transformed into *Escherichia coli* S$\phi$732 (see Table I). Plasmid pMFS-5627 directs the expression of the met-asp-gln-bGH analog under the control of the deo P1-P2 promoter and the deo ribosomal binding site. Plasmid pMFS-5627 is a low level expressor of the bGH analog.

(ii) Plasmid pMFS-5603

Plasmid pMFS-5603 was produced from plasmid pMFS-5627 by replacing the deo ribosomal binding site with the cII ribosomal binding site as shown in FIG. 41. Plasmid pMFS-5603 was transferred into *Escherichia coli* S$\phi$732 and yielded an intermediate level expression of bGH analog protein (see Table II).

(iii) Plasmid pMFS-5605

To produce a better deo P1-P2 expressor of the bGH analog, the PAR fragment from plasmid pEFF-920 was ligated into plasmid pMFS-5603. The resulting plasmid pMFS-5605 (FIG. 42) directs surprisingly high level expression of the bGH analog (20–25% of the total cell protein) under the control of the deo P1-P2 promoter and the cII ribosomal binding site. The results of bGH analog expression are shown in Table II. Plasmid pMFS-5607 (FIG. 46) was constructed from plasmid pMFS-5605 by replacing the ampicillin resistance gene by one for tetracycline resistance. Plasmid pMFS-5607 was deposited in *Escherichia coli* strain Sϕ930(F⁻) in the ATCC under Accession No. 67704. Note that the *Escherichia coli* F⁻ strains are described in Example 21.

(b) Growth of Escherichia coli Sϕ732 harboring plasmids expressing bGH analog

The growth of bGH analog expressing plasmids pMFS-5627, pMFS-5603 and pMFS-5605 in *Escherichia coli* Sϕ732 was studied at bench scale level. The plasmids were all grown initially in LB medium (Example 13b)+ampicillin+0.2%–0.3% glycerol. Subsequently they were all grown in minimal medium (Example 2)+0.2% glucose; when the glucose was depleted 0.2%–0.3% glycerol was added (see Example 13b).

Example 15

Standard Techniques Used Throughout the Examples

*Escherichia coli* transformation and isolation and purification of plasmid DNA were performed according to Maniatis et al. in "Molecular Cloning: A Laboratory Manual", Cold Spring Harbor (1982). DNA fragments were isolated from gels prepared with low melt agar (FMC) and purified with phenol. DNA sequencing was achieved according to the dideoxy method of Sanger et al., Proc. Natl. Acad. Sci. U.S.A. 74: 5463–5467 (1977).

Protein was determined by the method of Lowry et al., J. Biol. Chem. 193: 265–275 (1954). SDS-polyacrylamide gels for electrophoresis were prepared as described by Laemmli, U. K., Nature 227: 680–685 (1970) and stained with Coomassie blue R. 15 µl of total cell extract was applied per slot unless otherwise specified.

Enzyme activity of superoxide dismutase was measured in crude extracts according to the method of McCord et al., J. Biol. Chem. 244: 6049–6055 (1969). Highly purified SOD that renders about 4000 units/mg protein was used as standard.

Colony hybridization with synthetic probes was essentially as described by Grunstein et al., Proc. Nat. Acad. Sci. U.S.A. 72: 3961–3965 (1975). Hybridization was performed at 8×SSC at 42° C. for 18 h and the washes were carried out with 5×SSC/0.1% SDS at the same temperature. To alter stringency, both SSC concentration and temperature were changed according to need. Nick translation on purified DNA fragments was as described in Maniatis et al. (supra). Hybridization was performed using 5×SSC at 60° C. for 18 h then washed with 1×SSC/0.1% SDS. Agfa X-ray films were usually exposed to nitrocellulose filters for 4–6 h before development.

Restriction endonuclease, $T_4$ ligase, $T_4$ DNA polymerase and *Escherichia coli* DNA polymerase (Klenow fragment) were obtained from New England Biolabs and used as recommended by manufacturers. $\gamma^{32}P$-ATP, $\alpha^{32}P$ deoxy-CTP and $\alpha^{32}P$ deoxy-ATP was purchased from Amersham.

Bacterial Growth and Extraction

The *Escherichia coli* strains used in this study are listed in Table I. Unless otherwise indicated, cultures were grown in LB or minimal salt solutions (Vogel & Bonner 1956) supplemented with ampicillin (100 µg/ml) or tetracycline (12.5 µg/ml), including 0.2–0.3% glycerol as sole carbon source.

*Escherichia coli* cells harboring a plasmid expressing hSOD analog were grown in medium to which $Cu^{++}$ and $Zn^{++}$ were routinely added (usually at 75 and 10 µg/ml respectively, unless otherwise indicated). The addition of Cu is to allow production of enzymatically active hSOD analog as is described in U.S. Pat. No. 4,742,004. Cells were grown overnight at 37° C. and an equivalent of 1.0 $OD_{660}$ harvested. The bacterial pellet was resuspended in 100 µl of 50 mM Tris-HCl pH 8 and lysed in 3× sample buffer containing 30% (v/v) glycerol, 9% SDS, 2.1M mercaptoethanol, 187.5 mM Tris-HCl pH 6.8 and 0.5% bromophenol blue and heated in boiling water for 5 min. Extracts for SOD enzyme activity determination were prepared by disrupting cells by sonication.

Oligonucleotide Synthesis

Oligodeoxynucleotides were prepared by solid phase synthesis using phosphoramidite chemistry. The synthetic procedure employed was essentially that described by Adams et al., J. Am. Chem. Soc. 105: 661–663 (1983) and Beaucage et al., Tetrahedron Letts 22: 1859–1862 (1981).

The synthetic oligomers were purified by gel electrophoresis followed by $C_{18}$ chromatography. One-fifth of each deblocked lyophilized product was dissolved in 20 ml of gel buffer containing 80% (v/v) formamide, loaded onto a 40 cm 20% acrylamide/7M urea gel and electrophoresed at 300 v for 15 hr. Full length products were located by transferring the gel with saran wrap onto a fluorescent TLC plate with a 254 nm fluorescent indicator (Merck) and analyzed by detecting UV shadows. Excised gel fragments were crushed and transferred to siliconized tubes containing 3 ml of 0.5M ammonium acetate and heated at 60° C. for 60 min. The DNA solution was recovered by filtration. Sep-Pak $C_{18}$ cartridges (Waters Associates) were wetted with 10 ml of 50% (v/v) acetonitrile and rinsed with 10 ml of distilled water prior to application of the gel eluates. After rinsing with 5 ml of distilled water the oligonucleotides were recovered from columns with three separate applications of 1 ml of 60% methanol and then lyophilized.

Example 16

Optimization of Chemical Induction of Porcine Growth Hormone (pGH) and Bovine Growth Hormone (bGH) Expression Under the Control of deo P1-P2

We describe below the optimization of production of growth hormones in *Escherichia coli* cells harboring a plasmid which expresses the growth hormone under the control of the deo P1-P2 promoters. The rationale was to achieve the desired biomass of the *Escherichia coli* cells by initial growth on glucose, so that expression controlled by the strong deo P2 promoter is subject to catabolite repression. Subsequently, after depletion of glucose, a non-glucose carbon source was added allowing chemical induction of the deo P2 promoter and production of the growth hormone.

The chemical induction methodology turned out to yield consistent results for growth hormone production and led to the decision to develop a similar methodology for growth and expression in fermentation vessels. Note that constitutive production of the insoluble growth hormones yielded poor results. However, high level constitutive expression of soluble polypeptides such as hSOD analog can be achieved (see Example 2).

Bench Scale Optimization

Experiments were undertaken to optimize expression of the pGH analog and the bGH analog using the plasmids containing the deo P1-P2 promoters described in the above examples. In particular, the plasmid used for pGH expression was plasmid pEFF-920 (FIG. 39 and Example 13b), which expresses met-asp-gln-pGH analog. The plasmids used for bGH expression were plasmid pMFS 5607 (FIG. 46) and plasmid pMFS 5605 (Example 14b and FIG. 42) which are tetracycline resistant and ampicillin resistant respectively, and which both express met-asp-gln-bGH analog. All these plasmids contain the PAR fragment. We compared expression in two different hosts, S$\phi$732 which is cyt R⁻ deo R⁻ (no functional deo repressor but contains deo enzymes) and S$\phi$930 which is cytR⁻ and is deleted for the deo enzymes. (See Table Ia for full description of these cell lines.) Cultures were grown overnight in 50 ml minimal medium (see below) to which glucose was added (final concentration 0.2–0.4%). Upon depletion of glucose, a carbon source such as sodium lactate, fructose, succinate, or sodium malate was added to a final concentration of 0.2–0.4%, and the culture was grown for another 3–4 h at 37° C. Samples were removed at 2 h time intervals (1 O.D.$_{660}$ equivalent) and applied to SDS polyacrylamide gels. The results show that fructose and sodium lactate were the best of all carbon sources tested. The expression of pGH analog was consistently somewhat higher than that of bGH analog in the same host. Host S$\phi$930 was found to be superior to host S$\phi$732, therefore all scale up experiments carried out in the 2 liter fermentors were with host S$\phi$930.

Optimization of deo System in 2 Liter Fermentor Vessels

Composition of Medium

Components of this medium are in g/liter unless otherwise specified. The minimal medium described below is similar to that described in Example 2. Note that the media are modified or altered according to the requirements of the different bacterial strains.

$K_2HPO_4$—8
$KH_2PO_4$—2
Na-citrate—2
$NH_4Cl$—3
Na-Acetate—3
$K_2SO_4$—0.6
$FeNH_4$ Citrate—0.02
CaCl—0.04
Trace elements—3 ml/liter
Trace Elements Stock
$MnSO_4.H_2O$—1 g
$ZnSO_4.7H_2O$—2.78 g
$COCl_2.6H_2O$—2 g
$NaMoO_4.2H_2O$—2 g
$CaCl_2.2H_2O$—3 g
$CuSO_4.5H_2O$—1.85 g
$H_3BO_3$—0.5g
Conc. HCl—100 ml
Deionized $H_2O$—900 ml
*Added in certain experiments.

$MgSO_4.7H_2O$ is added after sterilization to final concentration of 400 mg/liter. Glucose is added at time of seeding the fermentor to final concentration of 10 g/l (20 ml of 50% stock). Ampicillin is added to a final concentration of 100 µg/ml.

Preparation of Seed Culture

Two hundred ml of minimal medium containing glucose (0.8 ml from 50% stock), ampicillin and $MgSO_4.7H_2O$ is seeded with *Escherichia coli* S$\phi$930/pMFS 5605 or S$\phi$930/pMFS 5607 (bGH analog) or S$\phi$930/pEFF 920 (pGH analog) from a freshly growth LB agar plate containing glucose, to yield an OD$_{660}$ of 0.05. The culture is grown overnight at 37° C. at 200–250 rpm (New Brunswick shaker) to reach an OD$_{660}$ of 2–3.

Fermentor

The working volume of the 2 liter fermentor used was 1 liter and the temperature was maintained at 36°–37° C. The fermentor was seeded with 200 ml overnight culture plus 20 ml 50% glucose. This concentration of glucose is sufficient to reach an OD$_{660}$ of 10–12. Alternatively, the priming may be achieved with 10 ml glucose and glucose feeding simultaneously with pH control. The pH is maintained at 7.2 from start to end and is controlled by feeding 10% $NH_4OH$. Usually, a predetermined volume of glucose of 20 or 40 ml was used to reach 10 or 20 OD units respectively. During the growth phase with glucose, dissolved oxygen should be maintained not lower than 20%, which is a non-limiting level of aeration for biomass production. Antifoam is added as needed. A sudden rise in dissolved oxygen (D.O.) to about 70% marks the point at which the glucose is fully exhausted. At this stage 20 ml of 50% fructose is added and the pump is connected to feed 50% fructose from a 100 ml reservoir. After several minutes the dissolved oxygen starts to drop and is maintained between 5–15%, and no higher; this is a low level of aeration for growth hormone analog production. Induction with fructose is carried out for 3–4 h. Fructose consumption is difficult to determine since there is no fast way to estimate its concentration. We assume that the rate of consumption of fructose is similar to that of glucose.

Table III shows specific productivity of growth hormone obtained by fermentation of the host vector systems S$\phi$930/pEFF 920, S$\phi$930/pMFS 5605 and S$\phi$930/pMFS 5607. The system S$\phi$930/pEFF920 yields a specific productivity of 0.1 for pGH which is as good as that obtained with the $\lambda$ P$_L$ system. The specific productivity of bGH from ampicillin or tetracycline resistant plasmids appears to be very similar (plasmids pMFS 5605 and pMFS 5607, respectively).

Note that specific productivity is defined as gram protein produced per gram dry cell weight.

TABLE III

Specific Productivity of Growth Hormones Produced by Host/Plasmid Systems in Various Fermentations

| Strain | OD$_{660}$ t$_o$ | OD$_{660}$ t$_e$ | D.W. t$_e$ | S.P. | Carbon Source Added After Glucose |
|---|---|---|---|---|---|
| S$\phi$732/pMF 5607 tet$^r$ (bGH) | 8.5 | 15.25 | 8.5 | 0.050 | Sodium Lactate |
| S$\phi$732/pMF 5607 tet$^r$ (bGH) | 10.2 | 20.00 | 6.5 | 0.080 | |
| S$\phi$930/pMF 5605 Amp$^r$ (bGH) | 12.2 | 45.00 | 14.1 | 0.124 | Fructose (43 g) |
| S$\phi$930/pMF 5605 Amp$^r$ (bGH) | 12.8 | 48.00 | 14.8 | 0.093 | Fructose (43 g) |
| S$\phi$930/pMF | 11.9 | 40.75 | 15.1 | 0.140 | Fructose |

TABLE III-continued

Specific Productivity of Growth Hormones Produced by Host/Plasmid Systems in Various Fermentations

| Strain | $OD_{660}$ $t_o$ | $OD_{660}$ $t_e$ | D.W. $t_e$ | S.P. | Carbon Source Added After Glucose |
|---|---|---|---|---|---|
| 5607 S$\phi$930/pEFF 920 Amp$^r$ (pGH) | — | 50.00 | 11.8 | 0.143 | Fructose from start to end (75 g) |
| S$\phi$930/pEFF 920 Amp$^r$ (pGH) | 8.0 | 50.00 | 15.9 | 0.127 | Fructose (30 g) |
| S$\phi$930/pEFF 920 Amp$^r$ (pGH) | 8.1 | 38.50 | 13.8 | 0.099 | Fructose (33 g) |
| S$\phi$930/pEFF 920 Amp$^r$ (pGH) | 12.2 | 56.00 | 17.4 | 0.125 | Fructose (45 g) |
| S$\phi$930/pEFF 920 Amp$^r$ (pGH) | 8.3 | 56.00 | 17.2 | 0.096 | Fructose (45 g) |
| S$\phi$930/pEFF 920 (pGH) | 12.7 | 52.00 | 17.0 | 0.101 | Fructose (40 g) |
| ATCC 12435/ pEFF 902 (pGH) ($\lambda$ $P_L$ system) | 13.0 | 36.00 | 12.5 | 0.108 | |

Abbreviations:
$t_o$ - $OD_{660}$ at start of fructose or sodium lactate feeding
$t_e$ - $OD_{660}$ at end of fermentation
D.W. $t_e$ - Dry weight in mg at end of fermentation
S.P. - Specific productivity defined as gram protein produced per gram dry cell weight

Example 17

Construction of High Copy Number Plasmid Expressing bGH

It was decided to construct a high copy number bGH expressing plasmid and to ferment *Escherichia coli* harboring this plasmid using the optimized conditions described in Example 16.

The construction of the high copy number expressing bGH is as shown in FIG. 48. The hSOD gene in pMFS 2005 (FIG. 9 and ATCC Accession No. 67362) was replaced with that of bGH originating from pMFS 5605 (FIG. 42). The resulting plasmid, designated pMFS 2006, is tetracycline resistant, and this plasmid was introduced to *Escherichia coli* S$\phi$930.

Growth and Expression in Fermentor

The conditions of fermentation of this culture were essentially the same as described in Example 16. Since cells containing pMFS 2006 are tetracycline resistant (and therefore grow poorly in minimal medium) the seed culture was supplemented with 1 ml LB medium to facilitate a good growth. $OD_{660}$ of the overnight culture was about 2–3. The fermentor contained 800 ml of medium and the entire 200 ml of seed culture (or nearly all of it) was added to the fermentor to obtain an O.D.$_{.660}$ of 0.2–0.4. The amount of glucose added depends on the OD desired prior to fructose feeding. For OD of 10–12, 10 g was added, whereas for OD of 30, 30 g was added (in general the relationship is 1 g glucose to 1 OD unit).

A sudden increase in dissolved oxygen (D.O.) marked the point of glucose depletion. At this stage 20 ml fructose was added and the pump was connected to a 100 ml reservoir containing 50% fructose. The D.O. dropped after a few minutes of fructose feeding and reached approximately 20%–30%; at this point stirring was reduced to obtain a D.O. not higher than 15%. This chemical induction was carried out for 3 hours.

Table IV shows the specific productivity of bGH obtained in various fermentations. The results demonstrate that addition of acetate to the medium contributes to an increase in specific productivity to about 0.2; the acetate concentration used is listed in the composition of the medium in Example 16.

TABLE IV

Specific Productivity (S.P.) of bGH Produced in Fermentor Using *Escherichia coli* S$\phi$920/pMFS 2006 in Various Fermentations

| $OD_{660}$ $t_o$ | D.W. $t_o$ | $OD_{660}$ $t_e$ | D.W. $t_e$ | S.P. | Addition to Medium | Fructose Added at Start (g) |
|---|---|---|---|---|---|---|
| 8.8 | 25.0 | 20.5 | 5.5 | 0.143 | No Acetate | 25 |
| N.D. | N.D. | 18.6 | 5.5 | 0.220 | Acetate | 30 |
| 11.0 | 4.3 | 34.7 | 10.7 | 0.153 | No Acetate | 35 |
| 11.4 | 3.8 | 30.0 | 9.9 | 0.164 | No Acetate | 30 |
| N.D. | N.D. | 36.5 | 12.1 | 0.160 | No Acetate | 25 |
| N.D. | N.D. | 16.5 | 5.9 | 0.160 | No Acetate | 25 |
| N.D. | N.D. | 39.5 | 11.7 | 0.230 | Acetate | 25 |
| N.D. | N.D. | 25.0 | 7.2 | 0.220 | Acetate | 27 |
| N.D. | N.D. | 33.0 | 10.7 | 0.200 | Acetate | 33 |
| N.D. | N.D. | 14.0 | 4.7 | 0.190 | Acetate | 20 |

Abbreviations:
$t_o$ - $OD_{660}$ at start of fructose feeding
$t_e$ - $OD_{660}$ at end of fermentation
D.W. $t_o$ - Dry weight in mg at start of fructose feeding
D.W. $t_e$ - Dry weight in mg at end of fermentation
S.P. - Specific productivity defined as gram protein produced per gram dry cell weight

Example 18

Construction of Deo Expression Vectors Containing Translational Enhancer

Plasmid pMF 5531 (Example 1 and FIG. 4) harboring deo P1-P2 promoters and the slightly modified deo ribosomal binding site directs low-level expression of hSOD analog protein. It was reported by P. O. Olins and S. H. Rangwala at the 1987 meeting on Molecular Genetics of Bacteria and Phages, Cold Spring Harbor Laboratory, New York, that AT rich sequences upstream of the ribosomal binding site may enhance the expression of prokaryotic genes in certain circumstances. It was decided to investigate if AT rich sequences enhanced eucaryotic gene expression directed by prokaryotic promoters such as the deo promoter.

To achieve this end, plasmid pMF 5534 was prepared from pMF 5531 as shown in FIG. 43 and in the Description of the Figures. This plasmid contains in 5' to 3' sequence the complete deo P1-P2 promoter sequence including an additional AT rich sequence, an NdeI restriction site and the hSOD gene. Plasmid pMF 5534 was introduced into *Escherichia coli* strain MC 1061 by transformation. Several individual colonies were picked and tested for expression by growth in LB medium containing 0.3% glucose and 100 units/ml ampicillin, buffered with M9 minimal salt solution (LB medium is described in Example 13a; M9 minimal salt solution is described by J. M. Miller in "Experiments in Molecular Genetics", Cold Spring Harbor Laboratory, 1972, page 431). These cells containing pMF 5534 surprisingly expressed hSOD at very high levels whereas the parental plasmid pMF 5531 is a poor expressor of hSOD analog.

Note that the only difference between these two plasmids is that pMF 5534 contains the AT-rich sequence and this demonstrates that the AT-rich sequence greatly enhances expression. Plasmid pMF 5534 has been deposited in *Escherichia coli* strain Sφ930(F⁻) in the ATCC under Accession No. 67703. More details of hSOD analog production using plasmid pMF 5534 are given in Example 19; we surprisingly found that production levels of hSOD analog are 2–5 times higher at 30° C. than at 37° C.

To test if the enhanced expression is associated with high levels of mRNA synthesis or enhanced translation, mRNA was isolated from late log phase growing cells from a variety of host/plasmid systems such as ATCC 12435/pMF-5531, ATCC 12435/pMF 5534, and controls such as ATCC 12435 and Sφ930 (Δ deo, deo R⁻). The purified mRNA from all samples were brought first to the same concentration and then passed through a dot-Blot apparatus containing a nitrocellulose filter. The nitrocellulose filter was hybridized to synthetic DNA probe #2913 (shown in the Description to FIG. 4) which contains the 5' end untranslated sequence of the deo P2 transcribed message. The dots observed on x-ray film were matched to the nitrocellulose filter, and the nitrocellulose filter segments were excised and counted in a scintillation counter. The counts produced using *Escherichia coli* Sφ930 mRNA were used as the zero control since Sφ930 contains no deo sequences; the counts produced by ATCC Accession No. 12435 mRNA were considered as the amount of deo mRNA present in host cells containing no plasmid and were subtracted from the counts obtained with mRNA obtained from host containing pMF 5531 and pMF 5534. The comparison of results between hosts containing pMF 5531 and pMF 5534 show that mRNA levels in hosts containing pMF 5534 is 1.5 to 2.5 times higher than that in pMF 5531. However, the same comparison made on the basis of protein band intensity reveals a 15–20 fold increase in the extract of Sφ930/pMF 5534. These results indicate that enhancement of hSOD expression occurs at the level of translation.

Deo P1 Driven Expression of hSOD

As discussed in the Background of the Invention, deo P1 is considered to be a poor promoter. In addition, we knew deo P1 is a poor promoter of hSOD analog protein since plasmid pMF 5516 (FIG. 3), containing deo P1 (but no deo P2 due to a deletion of 48 base pairs) does not express measurable hSOD analog protein. To test the possibility that the AT rich sequence may enhance expression driven by deo P1, the deo P2 promoter on plasmid pMF 5534 was removed. This was achieved by cleavage of pMF 5534 with AvrII and BglII which removes about 500 bp between deo P1 and the deo RBS. Following a fill-in reaction of the cohesive ends with Klenow enzyme, the large fragment was isolated from agarose gel, purified and ligated with T₄ ligase. The new plasmid designated pMF 5540 (FIG. 44) was introduced by transformation to a variety of hosts and grown in LB medium containing ampicillin and 0.3% glucose. SDS electrophoresis revealed an unexpectedly heavy band comigrating with purified hSOD. Comparison of total cell protein band intensities on SDS gels of hosts containing pMF 5540 or pMF 5534 surprisingly revealed that pMF 5540 containing deo P1 alone produces about 50%–75% of the hSOD observed with pMF 5534.

The conclusion reached was that the negligible hSOD expression driven by deo P1 is so increased by the AT rich enhancer sequence that cells harboring a plasmid containing such a construct are very good expressors of hSOD analog protein.

*Escherichia coli* host cells containing pMF 5540 are not subject to catabolite repression, because the promoter is the deo P1. Such cells can therefore be grown for expression of hSOD analog in the presence of glucose and there is no need to switch to fructose. (See discussion of catabolite repression in Example 13.)

The AT Rich Region Lacks Inherent Promoter Activity

To ensure that the AT rich fragment (the enhancer) present in plasmid pMF 5534 has no inherent promoter activity, plasmid pMF 5534 was cleaved to eliminate the entire deo P1-P2 promoter except the modified AT rich region and ribosomal binding site, as described in FIG. 44. The resulting plasmid, pMF 5541, was introduced into *Escherichia coli* Sφ930 and individual clones were tested for expression of hSOD. SDS gel electrophoresis of clones harboring plasmids with no deo P1-P2 revealed a very faint band with comigrated with hSOD. This low level expression is possibly attributed to "readthrough" activity which produced extremely low mRNA that could be enhanced by the high translation activity of the AT rich enhancer sequence. Thus, the experiment indicates that the AT rich region probably lacks inherent promoter activity.

Enhancer activity was also shown in hosts containing plasmid pMF-945 which yielded high pGH analog levels (FIG. 45). A similar construct (FIG. 46) harboring the bGH gene on plasmid pMF 5608 yielded low bGH analog levels.

Example 19

Secretion of Human Superoxide Dismutase (hSOD) and Bovine Growth Hormone (bGH) Into the Medium in the Presence of Copper and Zinc Ions We showed in Examples 1 and 2 that high level production of hSOD analog by *Escherichia coli* host cells harboring plasmids which contain the hSOD gene under the control of the deo P1-P2 promoters can be achieved. We subseqently found that such *Escherichia coli* cells grown in fermentors in minimal salt medium containing a carbon source and $Cu^{+2}/Zn^{+2}$ ions surprisingly release hSOD analog preferentially into the medium. This was observed for cultures grown in fermentors for periods longer than 16 hours. SDS gel electrophoresis of samples of cell free medium revealed after Coomasie staining, a band comigrating with purified hSOD analog protein. The intensity of this band increased with time up to 48–60 h from start of fermentation.

In one experiment a culture of *Escherichia coli* Sφ930 harboring plasmid pMF2005, a high copy number SOD expressor (FIG. 9) was grown initially on glucose as carbon source and when the glucose was depleted at $OD_{660}=24$, fructose was added. The culture conditions for hSOD analog production comprised low aeration conditions (1 vvm) at pH=7.4 and at 37° C.

As described above, a band comigrating with purified hSOD analog was found on SDS gels of cell-free medium. To demonstrate that this band is indeed the hSOD analog, a Western blot was made and the nitrocellulose filter was reacted with radiolabelled anti-hSOD antibody. The observed band reacted with the antibody confirming that the protein is the hSOD analog. To test if the hSOD analog is active enzymatically, hSOD was assayed in vitro according to the method of McCord et al. (Example 15). Quantitation of the protein band seen on SDS gel and the enzymatic activity were in close agreement. At $OD_{660}=30$, the hSOD enzyme activity in the medium was 0.45 g/liter.

In control experiments where no $Cu^{+2}/Zn^{+2}$ was added no hSOD analog protein was released into the medium.

A more dramatic observation was made with *Escherichia coli* Sφ930 harboring plasmid pMF 5534 grown at 30° C. in minimal medium containing glucose and $Cu^{+2}/Zn^{+2}$ ions. This host-vector system constitutively expressing hSOD analog can be grown on glucose throughout; apparently expression is achieved from the deo P1 plus enhancer and possibly partly from the deo P2 plus enhancer. The hSOD accumulated in the cell up to 24 h from start of fermentation to yield about 3 g/l of hSOD analog at $OD_{660}$=25. At this stage, hSOD started to spill into the medium. After an additional 12–15 h, gel electrophoresis revealed that hSOD analog protein was at a concentration of approximately 1.1 g/l in the medium, while in the cell the level was about 2.0 g/l. Little non-hSOD protein was found in the medium.

Note that the temperature used for fermentation of the *Escherichia coli* harboring plasmid pMF 5534 was 30° C. We surprisingly found that plasmids containing the enhancer sequence yielded 2–5 times more hSOD analog when grown at 30° C. than at 37° C.

We subsequently discovered that the release of protein into the medium in the presence of $Cu^{+2}/Zn^{+2}$ ions appears not to be unique to cells overproducing hSOD. *Escherichia coli* hosts containing pMF 5608 (FIG. 46), a plasmid harboring bovine growth hormone (bGH) gene under control of deo promoters, grown under identical conditions to those described above (including addition of $Cu^{+2}/Zn^{+2}$) released a number of proteins into the medium. However, since bovine growth hormone aggregates readily in vivo, the proportion of bGH in this secreted protein was low. In control experiments where no $Cu^{+2}/Zn^{+2}$ was added very little protein was released.

These observations show that secretion of protein into the medium depends on the presence of $Cu^{+2}/Zn^{+2}$ ions. The mechanism of this release is not clear. While not wishing to be bound by theory, we suspect that these ions change the pores in the membrane of the cell such that soluble proteins can leak from the cell. It is possible that copper ions alone or zinc ions alone or other divalent ions may produce the same effect.

Example 20

Construction of pGH "Independent" Expression Plasmids Without Use of Synthetic Linkers The construction of independent pGH expression plasmids has been described in Example 12. It was decided to construct a similar plasmid without the use of synthetic linkers.

The schematic outline for construction of such a plasmid is shown in FIGS. 49–51. The keys to the cloning was the use of the restriction enzyme NlaIII and the fact that the N-terminal and C-terminal portions of pGH are identical to those of bGH. Fragments were prepared as shown in FIG. 49, and the ligated plasmid containing the fragments (FIG. 50) was transformed into *Escherichia coli* MC 1061 and plated onto LB+tet agar plates. To identify colonies harboring the SmaI-NlaIII fragment, the PstI-PstI fragment of plasmid p107 (FIG. 49A) was isolated and cleaved with XmaI, which cleaves at the SmaI site (see FIG. 49). The resulting 340 bp fragment was purified from gel, nick translated and labelled with $32^P$ dCPT; it was then used for hybridization to identify clones. Hybridization was in 5 SSC at 55° C. and the wash was with 0.1 SDS/1 SSC. Several positive clones were picked and plasmid DNA was prepared by the method of Birenboim et al., J. Nucl. Acid Res. 1: 1513 (1979). These minipreps were then cleaved with different restriction endonucleases such as EcoRI, ScaI, PstI to verify that the 70 bp sequence harboring EcoRI and ScaI restriction sites is present. Two clones were picked, their plasmids purified by CsCl density centrifugation and designated pGH 30-2 and pGH 30-19 (FIG. 50). To generate the final construct, plasmids pFSAL B27 and pGH 30-2 were cleaved, fragments purified and then ligated as shown in FIG. 51.

The ligated mixture was used to transform *Escherichia coli* MC 1061. Several clones of this transformation were picked and tested for expression. Expression was monitored by growing the cells at 30° C. in 1 ml LB medium followed by "heat shock" at 42° C. for 2 h and then analysis on SDS gels. Two clones were picked for further analysis, plasmid DNA was prepared by CsCi gradient centrifugation and one plasmid was used for transformation of *Escherichia coli* strain ATCC 12435. Several clones were screened for expression and one, designated pMFS 928, was picked as a representative of the new independent pGH expression vectors. Sequencing of the EcoRI-HindIII fragment (containing the cII RBS and pGH analog sequence) confirmed the published sequence.

Expression of pGH analog from this plasmid is high and specific productivity is about 0.12.

It was subsequently discovered that the met-asp-gln-pGH analog expressed by this plasmid may possibly have an internal deletion of 1 glycyl residue (see Description of FIG. 51). Therefore, plasmid pMFS 929 was constructed as shown in FIG. 52 to generate a plasmid similar to pMFS 928 but containing the complete pGH analog sequence. Plasmid pMFS 929, an independent plasmid which expresses met-asp-gln-pGH analog protein at a high level, has been deposited in *Escherichia coli* strain (F⁻) W3110 in the ATCC under Accession No. 67705.

(For a description of *Escherichia coli* F⁻ strains, see Example 21.)

Example 21

*Escherichia coli* F⁻ Strains Used as Hosts for Plasmids

The following *Escherichia coli* F⁻ strains were constructed as described below and can be used as hosts for the plasmids described elsewhere in the specification: A4275, A5277, A4278, A4280, A4255 (F⁻) and Sφ930 (F⁻). Strain Sφ930 (F⁻) has been deposited harboring plasmid pMF 5534 as ATCC Accession No. 67703 and harboring plasmid pMFS 5607 as ATCC Accession No. 67704.

(a) Preparation of strains A4275, A5277, A4278 and A4280

The six *Escherichia coli* F⁻ strains listed below were obtained from the *Escherichia coli* Genetic Stock Center (C.G.S.C.), Dept. of Biology, Yale University, P.O.B. 6664, New Haven, Conn. These were transformed to carry the cryptic prophage λ cI 857N⁺ ΔBamHIΔHI and were cured of the Tn10 transposon. They were checked for the presence of the temperature-sensitive repressor (loss of immunity at 42° C.) and for the presence of the N⁺ gene (complementation of an N defective phage).

| C.G.S.C. Strain No. | Strain Designation | BTG Strain Produced |
|---|---|---|
| 6300 | F⁻ MG 1655 → | A 4275 |
| 4474 | F⁻ W 3110 → | A 5277 |
| 5290 | F⁻ W 2637 → | A 4278 |
| 6315 | F⁻ MM 294 → | Not yet available |
| 4452 | F⁻ 1000 → | A 4280 |
| 4448 | F⁻ 1100 → | Not yet available |

Note that C.G.S.C. strain no. 4474 designated strain (F⁻) W3110 has been deposited harboring plasmid pMFS 929 in the ATCC under Accession No. 67705.

(b) Preparation of strains A4255 (F⁻) and Sϕ930(F⁻)

*Escherichia coli* strains A4255 and Sϕ930, described in the specification (Table I), were "cured" to produce *Escherichia coli* strains 4255 (F⁻) and Sϕ930 (F⁻), respectively. The "curing" method used is described by J. H. Miller in "Experiments in Molecular Genetics", Cold Spring Harbor Laboratory, pp. 104–106 (1972).

Example 22

Construction of an Independent Human Growth Hormone (hGH) Expression Plasmid Containing the λ cI 857 Repressor Gene Under the Control of deo P1

Plasmid pTV 104(2), ATCC Accession No. 39384, is shown in FIG. 34. It contains the full length sequence of human growth hormone and is a high level expressor of hGH analog protein under the control of the λ $P_L$ promoter. Plasmid pTV 104(2) was cleaved at the SmaI site immediately downstream from the 3' end of the hGH sequence and just upstream from the NdeI site; the resulting full-length linear form of the plasmid was ligated to the small fragment containing the truncated deo P1 and the cI 857 repressor sequence, obtained by cleaving plasmid pFSAL-B27 (ATCC Accession No. 67071 and FIG. 24) with SspI.

The resulting plasmid, designated pTVR 723-6, is independent of λ genes on the host chromosome. It contains in 5' to 3' order and in clockwise orientation the λ $P_L$, the hGH coding sequence, the truncated deo P1 and the cI 857 repressor sequences. Plasmid pTVR 723-6 was transformed into *Escherichia coli* host ATCC Accession No. 12435 and showed high level expression of hGH analog protein, when thermoinducibly induced at 42° C.

Example 23

Comparison of Expression of Bovine Growth Hormone (bGH) from Independent Plasmids Containing Full-Length or Truncated deo P1

Plasmid pFSAL-B27 (FIG. 24 and ATCC Accession No. 67071) is an "independent" plasmid (independent of λ genes on the host chromosome). It expresses bGH under the control of the λ promoter, thermoinducibly controlled by the cI 857 repressor under the control of the truncated deo P1 promoter sequence (as described in Example 9).

We constructed a new plasmid identical to pFSAL-B27 except that it harbors the full-length deo P1 sequence.

(a) Construction of plasmid pMF-B27

Plasmid pMF 54DC (FIG. 24) containing the full-length deo P1 sequence and plasmid pFSAL-B27 were both cleaved with the restriction enzymes AatII and NsiI. The unique AatII site of each plasmid is located in the ampicillin-resistance sequence and the unique NsiI site is in the cI 857 sequence, i.e., downstream of the deo P1 sequence. The large fragment obtained from pFSALB27 was ligated with T4 ligase to the small AatII-NsiI fragment harboring the deo P1 sequence obtained from pMF 54DC. Following transformation of the resulting plasmid into the *Escherichia coli* F⁻ strain W2637 (Example 21), a clone was purified and the presence of full length deo P1 promoter in the plasmid, designated pMF-B27, was verified.

(b) Comparison of bGH Expression from Plasmids pMF-B27 and pFSAL-B27

Cultures of W2637 containing either plasmid pFSAL-B27 or the new plasmid pMF-B27 were compared. They were grown at 30° C. to $OD_{660}$ of 0.8 and then the temperature was raised at 42° C. to induce bGH synthesis. At 1 h time intervals one OD equivalent of cells was removed from each culture, pelleted, processed and analyzed by SDS polyacrylamide gel electrophoresis. The result shows that cultures harboring the new plasmid pMF-B27 expressed bGH at a level 5–8 times lower than cultures harboring pFSAL-B27.

To verify these findings, these two cultures were grown in 2 liter fermentors in minimal medium. Again, expression levels, as judged by densitometric scanning of SDS polyacrylamide gels stained with Coomassie blue and compared to 1 µg standard bGH protein revealed that bGH levels produced by pMF-B27 were 5–7 fold lower than those obtained with pFSAL-B27.

Hence, the fact that the deo P1 construct is truncated confers a surprising advantage, in level of growth hormone expressed, to the plasmid harboring it.

Similarly, any truncated deo P1 which includes part of the deo P1 sequence, but excluding the known operator-promoter region in the EcoRI site (see Example 9), is expected to control the production of the λ cI 857 repressor.

What is claimed is:

1. A double-stranded DNA plasmid which upon introduction into an *Escherichia coli* host cell renders the host cell capable of effecting expression of DNA encoding human copper/zinc superoxide dismutase or an analog having the biological activity of, and an amino acid sequence which is the same as that of the naturally-occurring human copper/zinc superoxide dismutase, and thereby effecting production of the human copper/zinc superoxide dismutase or analog comprising in 5' to 3' order the following:

a) DNA which includes in 5' to 3' order the tandem promoters deo P1 and deo P2;

b) DNA which includes a ribosomal binding site for rendering mRNA transcribed from the DNA encoding the human copper/zinc superoxide dismutase or analog capable of binding to ribosomes within the host cell;

c) an ATG initiation codon; and d) DNA encoding the human copper/zinc superoxide dismutase or analog in phase with the ATG initiation codon;

and which additionally includes a DNA sequence comprising an origin of replication from a bacterial plasmid capable of autonomous replication in the host cell and a DNA sequence which encodes a selectable or identifiable phenotypic trait which is manifested when the plasmid is present in the host cell.

2. A plasmid of claim 1, wherein the *Escherichia coli* host cell comprises Sϕ732, Sϕ744, MC1061, Sϕ540, Sϕ930, or ATCC Accession No. 12435.

3. A circular, closed plasmid of claim 1.

4. A plasmid of claim 1, wherein the ribosomal binding site is the deo ribosomal binding site.

5. A plasmid of claim 1, wherein the ribosomal binding site is a mutant of the deo ribosomal binding site comprising the BIG sequence #2015.

6. A plasmid of claim 1, wherein the ribosomal binding site is cII from a λ bacteriophage consisting of the sequence:

TAAGGAAATACTTACAT
ATTCCTTTATGAATGTA.

7. A plasmid of claim 1, wherein the ribosomal binding site is a mutant cII from a λ bacteriophage consisting of the sequence:

TAAGGAAGTACTTACAT
ATTCCTTCATGAATGTA.

8. A plasmid of claim 1, wherein the ribosomal binding site is the *E. coli* β-lactamase ribosomal binding site.

9. A plasmid of claim 1, wherein the ribosomal binding site consists of the sequence:

AATTCGAGCGCAAGGAAACAGGCTCA
GCTCGCGTTCCTTTGTCCGAGTAT.

10. A plasmid of claim 1, wherein the ribosomal binding site consists of the sequence:

AATTCAATAATATTGAAAAAGGAAGAG
GTTATTATAACTTTTTCCTTCTCAT.

11. A plasmid of claim 1, wherein the ribosomal binding site consists of the sequence:

GACAAGCCTAGGTTTGTTTAACTTTAAGGAGAAATCATA
CTGTTCGGATCCAAACAAATTGAAATTCCTCTTTAGTAT.

12. A plasmid of claim 1, wherein the origin of replication is from pBR322.

13. A plasmid of claim 1, wherein the phenotypic trait is drug resistance.

14. A plasmid of claim 1, wherein the drug resistance is resistance to ampicillin or tetracycline.

15. A plasmid of claim 1, which additionally comprises a sequence translation enhancer.

16. A plasmid of claim 1 for producing an analog of human copper/zinc superoxide dismutase selected from the group consisting of pMF 5531 having the restriction map shown in FIG. 4, pMF 5519 having the restriction map shown in FIG. 5, pMF-558-26 having the restriction map shown in FIG. 6, pMF-5536, pMF-5520 having the restriction map shown in FIG. 7, pMF-2005 having the restriction map shown in FIG. 9 and deposited under ATCC Accession No. 67362 pMFS-5533A having the restriction map shown in FIG. 17 and pMFS-5538 having the restriction map shown in FIG. 18.

17. A host plasmid system for producing an analog of human copper/zinc superoxide dismutase comprising any of the plasmids of claim 16 in an *Escherichia coli* host.

18. A method for producing an analog of human copper/zinc superoxide dismutase which comprises growing the hose plasmid system of claim 17 under conditions permitting production of the analog of human copper/zinc superoxide dismutase and recovering the resulting analog.

19. A host plasmid system for producing human copper/zinc superoxide dismutase or analog comprising a plasmid of claim 1 in an *Escherichia coli* host.

20. A host plasmid system of claim 19, wherein the host strain is an F⁻ strain.

21. A host plasmid system of claim 19, wherein the *Escherichia coli* host is selected from the group consisting of Sϕ732, ATCC Accession No. 12435, Sϕ540, MC1061, and Sϕ930.

22. A method for producing human copper/zinc superoxide dismutase or analog which comprises growing the host plasmid system of claim 19 under conditions permitting production of the human copper zinc superoxide dismutase or analog and recovering the resulting human copper/zinc superoxide dismutase or analog.

23. The method of claim 22, wherein the conditions comprise low aeration.

24. The method of claim 22, wherein the conditions comprise growth on a medium containing a non-glucose carbon source.

25. The method of claim 24, wherein the non-glucose carbon source is selected from the group consisting of glycerol, fructose, succinate, sodium lactate and sodium malate.

26. The method of claim 22, wherein the conditions comprise initially growing the *Escherichia coli* cells in glucose and adding a non-glucose carbon source after depletion of the glucose.

27. The method of claim 26, wherein the non-glucose carbon source is selected from the group consisting of glycerol, succinate, sodium lactate, fructose and sodium malate.

28. The method of claim 22, wherein the human copper/zinc superoxide dismutase or analog is secreted into the medium in which the host plasmid system is grown upon addition of a divalent metal ion to the growth medium.

29. The method of claim 28, wherein the divalent metal ion is $Cu^{+2}$.

30. The method of claim 28, wherein the divalent metal ion is $Zn^{+2}$.

31. The method of claim 28, wherein the divalent metal ion is a mixture of $Cu^{+2}$ and $Zn^{+2}$.

32. The method of claim 28 further comprising growing the host plasmid system at about 30° C.

33. A double-stranded DNA plasmid which upon introduction into an *Escherichia coli* host cell renders the host cell capable of effecting expression of DNA encoding human copper/zinc superoxide dismutase or analog having the biological activity of, and an amino acid sequence which is the same as that of the naturally occurring polypeptide thereby effecting production of the human copper/zinc superoxide dismutase or analog, comprising in 5' to 3' order the following:

a) DNA which includes 5' to 3' order the tandem promoters deo P1 and deo P2;

b) a translation enhancer;

c) an NdeI restriction enzyme site;

d) an ATG initiation codon; and e) DNA encoding the human copper/zinc superoxide dismutase or analog in phase with the ATG initiation codon;

and which additionally includes a DNA sequence comprising an origin of replication from a bacterial plasmid capable of autonomous replication in the host cell and a DNA sequence which encodes a selectable or identifiable phenotypic trait which is manifested when the plasmid is present in the host cell.

34. A plasmid of claim 33 designated pMF 5534 deposited in *Escherichia coli* strain Sϕ930 (F⁻) under ATCC Accession No. 67703.

35. A host plasmid system for production of an analog of human copper zinc superoxide dismutase comprising the plasmid of claim 33 in an *Escherichia coli* host.

36. A host plasmid system of claim 35 wherein the host is selected from the group consisting of, Sφ732, ATCC Accession No. 12435, Sφ540, MC1061, and Sφ930.

37. A host plasmid system of claim 35, wherein the host is an F$^-$ strain.

38. A method of producing an analog of human copper/zinc superoxide dismutase which comprises growing the host plasmid of claim 35 under suitable conditions permitting production of the analog and recovering the resulting analog.

39. The method of claim 38 further comprising growing the host plasmid system at about 30° C.

* * * * *